United States Patent
Ivanusic

(10) Patent No.: US 10,472,408 B2
(45) Date of Patent: Nov. 12, 2019

(54) FUSION PROTEINS COMPRISING PARTIAL TETRASPANIN SEQUENCES AND A SYSTEM THEREOF FOR PRESENTING PEPTIDES ON THE CELL SURFACE

(71) Applicant: PETER UND TRAUDL ENGELHORN-STIFTUNG ZUR FÖRDERUNG DER LEBENSWISSENSCHAFTEN, Weilheim i.Obb (DE)

(72) Inventor: Daniel Ivanusic, Berlin (DE)

(73) Assignee: Peter und Traudl Engelhorn-Stiftung Zur Förderung der Lebenswissenschaften, Weilheim i. Obb (DE)

(*) Notice: Subject to any disclaimer, the term of this patent is extended or adjusted under 35 U.S.C. 154(b) by 0 days.

(21) Appl. No.: 15/555,313

(22) PCT Filed: Mar. 4, 2016

(86) PCT No.: PCT/EP2016/054682
§ 371 (c)(1),
(2) Date: Sep. 1, 2017

(87) PCT Pub. No.: WO2016/139354
PCT Pub. Date: Sep. 9, 2016

(65) Prior Publication Data
US 2019/0010211 A1 Jan. 10, 2019

(30) Foreign Application Priority Data
Mar. 5, 2015 (DE) .......................... 10 2015 002 851

(51) Int. Cl.
*C07K 14/705* (2006.01)
*A61K 39/00* (2006.01)
*G01N 33/68* (2006.01)

(52) U.S. Cl.
CPC .... *C07K 14/70596* (2013.01); *A61K 39/0005* (2013.01); *G01N 33/6803* (2013.01); *G01N 33/6872* (2013.01); *C07K 2319/03* (2013.01); *C07K 2319/035* (2013.01); *C07K 2319/40* (2013.01); *G01N 2333/70596* (2013.01)

(58) Field of Classification Search
CPC .......... C07K 14/70596; C07K 2319/03; C07K 2319/40; G01N 33/6803; G01N 33/6872; G01N 2333/70596; A61K 39/0005
See application file for complete search history.

(56) References Cited

FOREIGN PATENT DOCUMENTS

WO 2014/186649 A2 11/2014

OTHER PUBLICATIONS

Stratagene Catalog. p. 39, 1988.*
Fuminori Ryu et al: "Domain Analysis of the Tetraspanins. Studies of CD9/CD63 Chimeric Molecules on Subcellular Localization and Upregulation Activity for Diphtheria Toxin Binding.", Cell Structure and Function., vol. 25, No. 5, Jan. 1, 2000 (Jan. 1, 2000), pp. 317-327, XP055271431.
Stipp CS et al: "Funct

(56) References Cited

OTHER PUBLICATIONS

Ivanusic et al., "Investigation of membrane protein-protein interactions using correlativeFRET-PLA", Bio Techniques, vol. 57, No. 4, Oct. 2014, pp. 188-198.
Jin et al., "Targeting Protein-Protein Interaction by Small Molecules", Annu. Rev. Pharmacol Toxicol, 2014, 54, pp. 435-456.
Jones et al., "Protein-Protein Interactions: A Review of Protein Dimer Structures", Prog. Biophys. Molec. Biol., vol. 63, 1995, pp. 31-65.
Jones et al., "Principles of protein-protein interactions", Proc. Natl. Acad. Sci., vol. 93, Jan. 1996, pp. 13-20.
Kim et al., "A cell surface display system using novel GPI-anchored proteins in Hansenula polymorpha", Yeast, 2002, 19, pp. 1153-1163.
Kovalenko et al., "Structural organization and interactions of transmembrane domains in tetraspanin proteins", BMC Structural Biology, 2005, 5: Jun. 11, 2005, 20 pages.
Kremers et al., "Cyan and Yellow Super Fluorescent Proteins with Improved Brightness, Protein Folding, and FRET Forster Radius", Biochemistry 2006, 45, pp. 6570-6580.
Levy et al., "The Tetraspanin Web Modulates Immune-Signalling Complexes", NATURE, vol. 5, Feb. 2005, pp. 136-148.
Mao et al., "Construction of eukaryotic surface display based on the baculoviral F protein", Biotechniques, vol. 41, No. 3, 2006, pp. 266-270.
Mullard, "Protein-protein interatction inhibitors get into the grove", Nature Reviews, vol. 11, Mar. 2012, pp. 173-175.
Nicolay et al., "Autotransporter-based cell surface display in Gram-negative bacteria", Critical Revews in Microbiology, early online, 1-15, 2013.
Rahman et al, "Bombyx mori nucleopolyhedrovirus-based surface display system for recombinant proteins", Journal of General Virology, 2003, 84, pp. 2023-2031.
Green et al.: Molecular cloning : a laboratory manual. 1. (Cold Spring Harbor Laboratory Press, 2012), pp. 835-845.
Rao et al., Protein-Protein Interaction Detection: Methods and Analysis, International Journal of Proteomics, vol. 2014, Article ID 147648, 12 pages.
Raty et al., "Enhanced Gene Delivery by Avidin-Displaying Baculovirus", Molecule Therapy, vol. 9, No. 2, Feb. 2004, pp. 282-291.
Rogman, "Rational design of protein-protein interaction inhibitors", MedChemComm, 2013, 00, pp. 1-3.
Rubinstein et al., "CD9, CD63, CD81 and CD82 are components of a surface tetraspan network connected to HLA-DR and VLA integrins", Eur. J. Immunol, 1996, 26, pp. 2657-2665.
Stevers et al., "Modulators of 14-3-3 Protein-Protein Interactions", J. Med. Chem., 2018, 61, pp. 3755-3778.
Stipp et al., "Functional domains in tetraspanin proteins", TRENDS in Biochemcial Sciences, vol. 28, No. 2, Feb. 2003, pp. 106-112.
Sudhof, "The Synaptic Vesicle Cycle", Annu. Rev. Neurosci., 27, 2004, pp. 509-547.
Tomimatsu et al., "A rapid screening and production method using a novel mammalian cell display to isolate human monoclonal antibodies", Biochemical and Biophysical Research Communications, 441 (2013), pp. 59-64.
Van Bloois, "Decorating microbes: surface display of proteins on Escherichia coli", Trends in Biotechnology, vol. 29, No. 2, Feb. 2011, pp. 79-86.
Voller et al., "Enzyme immunoassays with special reference to ELISA techniques", Jouirnal of Clinical Pathology, 31, 1978, pp. 507-520.
Wang et al., "Construction of a novel system for cell surface display of heterologous proteins on Pichia pastoris", Biotechnol Lett, 29, 2007, pp. 1561-1566.
Weerapana et al., "Asparagine-linked protein glycosylation: from eukaryotic to prokaryotic system", Glycobiology, vol. 16, No. 6, pp. 2006, 91R-101R.
Yang et al., "Novel Bacterial Surface Display Systems Based on Outer Membrane Anchoring Elements from the Marine Bacterium Vibrio anguillarum", Applied and Eviromental Microbiology, vol. 74, No. 14, Jun. 2008, pp. 4359-4365.
Zhou et al., "Development of a novel mammalian cell surface antibody display platform", mAbs, vol. 2, issue 5, 2010, pp. 508-518.
Nicolson, "The Fluid-Mosaic Model of Membrane Structure: Still relevant to understanding the structure, function and dynamics of biological membranes after more than 40 years", Biochimica ET Biophsica Acta, 1838 (2014), pp. 1451-1466.
Whitelegge, "Integral Membrane Proteins and Bilayer Proteomics", Anal Chem. 2013, 85(5), pp. 2558-2568.
Berggard et al., "Methods for the detection and analysis of protein-protein interactions", Proteomics, 2007, 7, pp. 2833-2842.
Glick et al., "The Curious Status of the Golgi Apparatus", CELL, vol. 95, Dec. 1998, pp. 883-889.
Call et al., "The T Cell Receptor: Critical Role of the Membrane Environment in Receptor Assembly and Function", Annu. Rev. Immunol. 2005, 23, 101-125.
Sachs et al., "Introduction to the Membrane Protein Reviews: The Interplay of Structure, Dynamics, and Environment in Membrane Protein Function", Annu. Rev. Biochem., 2006, 75, pp. 707-712.
Macher, "Proteins at membrane surfaces—A review of appoaches", Molecular Biosystems, Nov. 2007, 3, pp. 705-713.
Smith , "Filamentous Fusion Phage: Novel Expression Vectors That Display Clonned Anitgens on the Virion Surface", Science, Jun. 1985, vol. 228, pp. 1315-1316.
Crameri et al., "Display of expression products of cDNA libraries on phage surfaces, A versatile screening system for selective isolation of genes by specific gene-product/ligand interaction", Eur. J. Bichem. 226, 1994, pp. 53-58.
Gu et al., "A phage display system for studying the sequence determinants of protein folding", Protein Science, 1995, 4, pp. 1108-1117.
Kehoe et al., "Filamentous Phage Display in the New Millennium", Chem. Rev. 2005, 105, pp. 4056-4072.
Chen et al., "Cell-Surface Display of Heterologous Proteins: From High-Throughput Screening to Environmental Applications", Biotechnol Bioeng 79; 2002, pp. 496-503.
Hoischen et al., "Novel Bacterial Membrane Surface Display System Using Cell Wall-Less L-Forms of Proteus mirabilis and *Escherichia coli*", Applied and Environmental Microbiology, Feb. 2002, vol. 68, No. 2, pp. 525-531.
Tafakori et al., "Microbial cell surface display: its medical and environmental applications", Iranian Jounal of Biotechnology, Oct. 2012, vol. 10, No. 4, pp. 231-239.
Rutherford et al., "Surface display of proteins by Gram-negative bacterial autotransporters", Microbial Cell Factories, 2006, 5:22, 15 pages.
Molecular Cell Biology, Transport of Ions and Small Molecules Across Cell Membranes, Chapter 7, 2013, p. 246.

\* cited by examiner

Fig. 9A-E
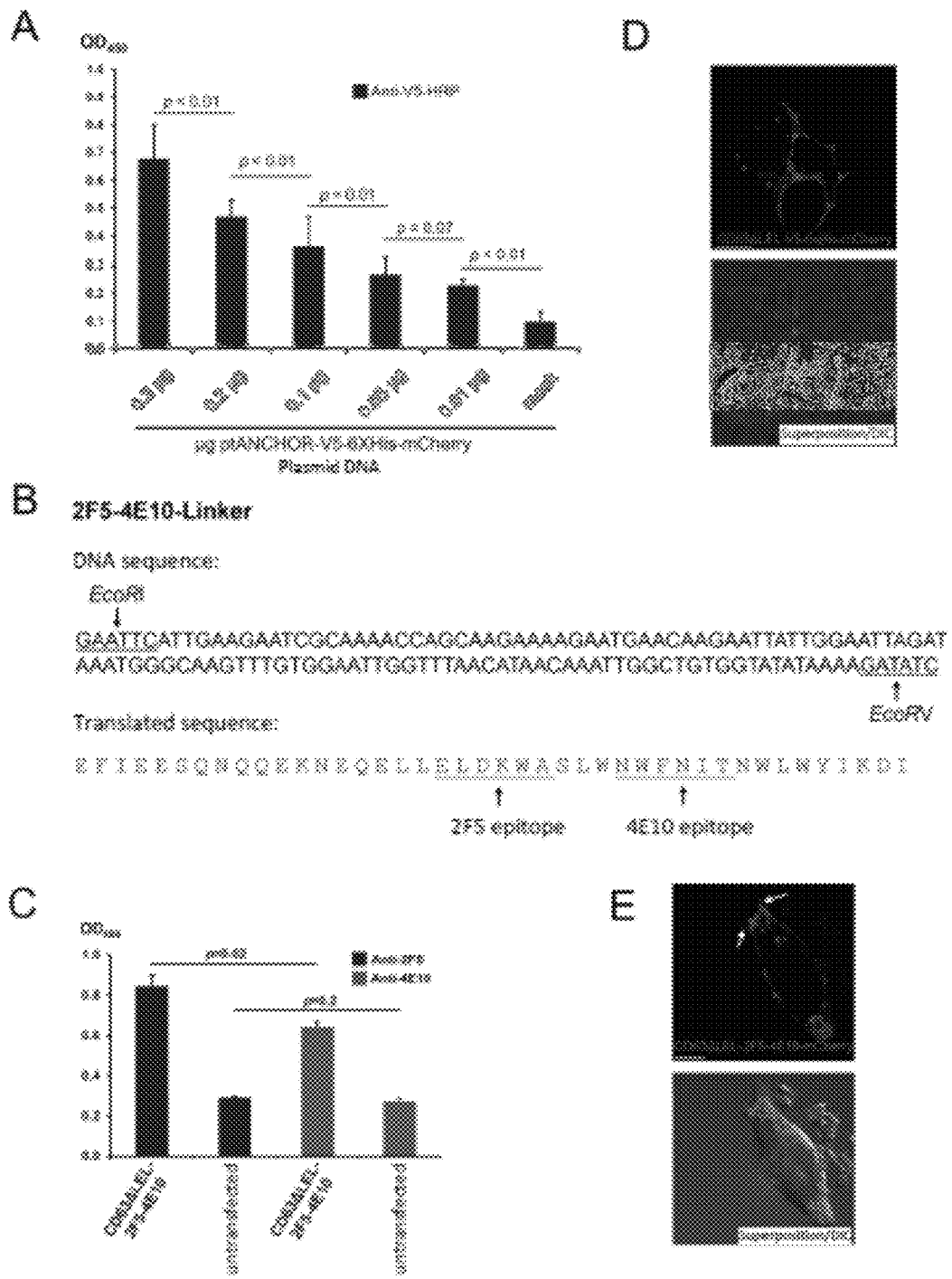

Fig. 10A-B
A  Linker in the vector pCMV-CD63ΔLEL-mCherry
DNA sequence:
CTGCAGGAATTCGATATCGGAGGAGGA
 PstI    EcoRI  EcoRV
Translated sequence:
L Q E F D I G G G
Linker in the vector pCMV-CD63ΔLEL-V2-mCherry
DNA sequence:
TTGGATCCAGCGGCCGCAGATCTCTGCAGGGAGGCGGAGGC
  BamHI              BglII    PstI
Translated sequence:
G S S G R R S L Q G G G
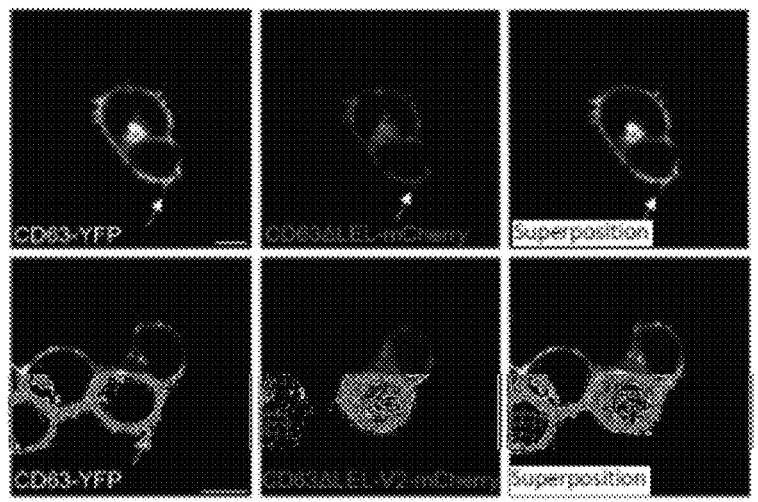

FUSION PROTEINS COMPRISING PARTIAL TETRASPANIN SEQUENCES AND A SYSTEM THEREOF FOR PRESENTING PEPTIDES ON THE CELL SURFACE

CROSS REFERENCE TO RELATED APPLICATION

This application is a 35 U.S.C. 371 National Phase Entry Application from PCT/EP2016/054682, filed Mar. 4, 2016, which claims the benefit of German Patent Application No. 10 2015 002 851.0 filed on Mar. 5, 2015, the disclosures of which are incorporated by reference in their entirety.

The subject-matter of the present application concerns fusion proteins based on tetraspanin proteins, in which the extracellular loop is replaced in whole or in part by peptide sequences of a different composition and also their production and use as transport vehicle. The disclosed fusion proteins are anchored in the membrane of cells and can be used to present foreign peptides fused with them on the cell surface.

The structural plan of cells and their physiology is coded by genes. The genes consist of DNA and are found either in the genome, or on extra-chromosomal elements. They express primary and secondary gene products, such as RNA and proteins. These can occur further modified enzymatically in a variety of ways.

The gene products are found primarily in the cytosol. The proteins are found in part also in the intracellular membranes of the compartments and in the outer cell membrane and also possibly the cell wall. In the case of eukaryotes, proteins and precursor RNAs are found in the cell nucleus. Proteins are sorted in intracellular membranes in the cytosol and distributed to cell compartments, but can also be exported from the cell by secretion. Export proteins from the endoplasmic reticulum (ER) can additionally be glycosylated in the Golgi apparatus during transport.

A particular protein species, the membrane-anchored proteins are actively directed to the cell membrane and anchor themselves there vertically to the membrane. Horizontally, however, in contrast, they are flexibly able to migrate within membrane owing to the membrane fluidity. Some membrane proteins are complexed with other heterologous membrane proteins in the cluster. Thus 80% of humane proteins act in associated protein complexes[1]. Some species interact with each other cooperatively in the membrane and form stable structures there.

A plurality of signal processes that allow the cell to interact with its environment are controlled by way of membrane proteins. Membrane transports of proteins by way of the cell membrane in connection with outward secretion processes are likewise possible.

For the presentation of epitopes the immune system uses MHC membrane proteins on cells, in order to identify potential invading pathogens in the cell. These physiological processes are mostly very well established in the cell and the proteins involved have evolved very specifically for this function, i.e. mostly very specifically directed at a certain function. Therefore one can expect additional, artificial amino-acid sequences to interfere with these functions.

Tetraspanins belong to a protein super-family with 33 members in mammals. The main characteristic of the tetraspanins are their 4 transmembrane domains TM1-4, which have also led to the naming. Tetraspanins contain additionally a small and a large extracellular protein loop (small and large extracellular loop), known also as SEL and LEL. The LEL contains a highly conserved CCG amino-acid motif. Furthermore an intracellular protein loop (small intracellular loop, SIL) is contained therein. N- and C-termini are localised intracellularly[34-36]. Using lateral protein-protein interactions (PPIs), tetraspanins organise themselves in tetraspanin-enriched microdomains (TEMs)[37,38].

To transport foreign proteins and epitopes of heterologous composition in an intentional way, for example to the surface of mammalian cells, e.g. human cells, and to present them there, particularly suitable carrier proteins (carriers) are required. These should have sufficient electromotive force and be able to use the membrane potentials, to guarantee a protein transport with a high translocation efficiency by way of the membrane to the cell surface[2-8]. In the past "display" systems became known, generally membrane-anchored proteins that can be used as carrier proteins for the presentation of foreign proteins by being genetically modified. One of the most well-known protein display systems is the phage display. It is used in the presentation of protein constituents on the surface of filamentous bacteriophages in the bacterial system[9-12]. However, in the past, heterologous proteins have also been presented successfully on the outermost membrane without the use of the phage display in the case of Gram-positive and Gram-negative bacteria. For this, different transport mechanisms within the bacterial cell were exploited, to direct proteins to the outermost membrane of the bacterial cell[13-20]. Further developments in display systems focussed on eukaryotic systems such as yeasts and insect cells, in order to ensure protein folding and modifications in recombinant proteins, such as e.g. N-glycosylations[21-29]. Initial display systems have also been developed already for use in the mammalian system[30-33].

The object of the present invention was the provision of a new possibility, starting out from this prior art, for anchoring any desired heterologous peptides in a plasma membrane and presenting them on the cell surface. Surprisingly it has now been found that tetraspanins are excellently suited as vehicles and have a highly efficient transport capability for foreign peptides fused with them for anchoring and presentation on the surface of cells. They are able to guide foreign peptides very efficiently to the plasma membrane of mammalian cells via the endoplasmic reticulum and the Golgi apparatus.

Proteins of the tetraspanin family have a protein loop (large extracellular loop, LEL) between the transmembrane domains TM3 and TM4 in the wild type. Surprisingly it was discovered within the framework of the present invention that this extracellular loop can be replaced in whole or in part by peptide sequences of a different composition and thus it is possible to transport the inserted heterologous peptide over a membrane by way of the tetraspanin carrier protein and anchor it in the membrane.

The invention is based on the simplicity of a uniform, molecular structure for flexible and variable sequence modulation in a modular protein expression system in conjunction with the function of a specific transport vehicle by way of cellular membranes and their anchoring there.

The vector systems provided make it possible to replace or add protein constituents flexibly by means of simple cloning strategies (e.g. to add individual epitopes and also create entire protein libraries).

After the expression of the tetraspanin fusion constructions according to the invention (integrated transiently or stably into the genome) the localisation of the fusion proteins in the membrane is almost quantitative. The tetraspanin proteins are translocated very efficiently onto the membrane. The already known systems do not come anywhere close to achieving this in this form (e.g. EGFR receptor).

The expression of the tetraspanin fusion proteins according to the invention takes place relatively quickly, normally overnight, whereas the expression of other transport systems usually take place over two days.

Apart from that, the stability of the fusion constructs and their longevity is better in comparison with the known proteins with the seven transmembrane domains, because no accumulation of cytosolic degradation products is found (recombinant GPCR receptors are known to be unstable).

With the system according to the invention, which has only four transmembrane domains, it is possible to transport one or more proteins on cellular surfaces stably and without any problem and fix and immobilise them there for example as stationary partner in interaction experiments with small molecules, further proteins such as antibodies, and also other proteins (e.g. catalytic enzymes), DNAs, RNAs and sugars etc.

The reactants of the fusion proteins on the membrane can now enter flexibly from the surrounding solution into specific reactions with the proteins and the glycosyl residues on the membrane.

The prerequisite for these reactions is functional conformation of the proteins. This is guaranteed in full in respect of the fusion proteins according to the invention.

A first subject-matter of the present invention is therefore a fusion protein, comprising a first domain (i), a second domain (ii) and a third domain (iii), wherein the second domain is disposed between the first and the third domain, wherein (i) a partial sequence of a tetraspanin, which includes the transmembrane domain 1 (TM1), the small extracellular loop (SEL), the transmembrane domain 2 (TM2), the small intracellular loop (SIL) and the transmembrane domain 3 (TM3), or comprises a sequence homologous thereto with a sequence identity of at least 70% over the entire length, (ii) comprises a peptide with a predetermined amino-acid sequence, having a sequence identity of less than 70% over the entire length in respect of the large extracellular loop (LEL) of a tetraspanin, and (iii) comprises a partial sequence of a tetraspanin, comprising the transmembrane domain 4 (TM4) or a sequence homologous thereto with a sequence identity of at least 70% over the entire length.

In the present invention it was found that the sequences TM1-3 and TM4 are responsible for the anchorage of the fusion protein on the membrane. Therefore a fusion protein according to the invention comprises firstly a first domain (i), comprising a partial sequence of a tetraspanin with the transmembrane domains TM1-TM3, and secondly a domain (iii), comprising a partial sequence of a tetraspanin with the transmembrane domain TM4, or sequences homologous thereto.

Within the meaning of the invention the term "tetraspanin" describes any desired proteins of the tetraspanin family, more particularly the 33 human tetraspanins. Tetraspanins can enter into specific interactions with each other in a membrane. This behaviour is favourable for transport over the membrane and anchoring there. This effect can be used in the fusion proteins according to the invention, in order also to transport the foreign peptide of the domain (ii) effectively over the membrane and to anchor it. Preferred examples of tetraspanins within the meaning of the invention are CD63, CD9, CD82, CD81, CD151 and CD53 (see sequence record for DNA sequences and protein sequences). Particularly preferably the partial sequences contained within a fusion protein according to the invention come from the tetraspanin CD63 (see sequence record for DNA and protein sequences).

As a basic principle it is possible to select a partial sequence of a first tetraspanin for domain (i) and to select a partial sequence of another tetraspanin for domain (iii). Preferably, however, all partial sequences are from the same tetraspanin, for example CD63, CD9, CD82, CD81, CD151 or CD53, preferably CD63 (see sequence record for DNA and protein sequences).

The domain (i) comprises preferably the transmembrane domain TM1, the small extracellular loop (SEL), the transmembrane domain TM2, the small intracellular loop (SIL) and the transmembrane domain TM3 of a tetraspanin, wherein the various transmembrane domains and loops follow each other directly, without any additional heterologous sequence segments being inserted between them. Particularly preferably the partial sequence corresponds to the wild type of a tetraspanin without any deviations in the form of, for example, substitutions, insertions or deletions of single or multiple amino-acids. It is however possible in principle to use modified partial sequences of a tetraspanin for the domain (i), provided these have a sequence identity of at least 70% over the entire length of the sequence, in relation to the wild type tetraspanin. More preferably the sequence identity is at least 80%, 85%, 90%, 95% or 99% over the entire length of the partial sequence of a tetraspanin contained in the domain (i).

In a particularly preferred embodiment of the invention the first domain (i) consists of the aforementioned partial sequence of a tetraspanin or of a sequence homologous thereto with a sequence identity of at least 70% (more preferably at least 80%, 85%, 90%, 95% or 99%) over the entire length.

The domain (iii) comprises a partial sequence of a tetraspanin, comprising the transmembrane domain TM4 of a tetraspanin or a sequence homologous thereto with a sequence identity of at least 70% over the entire length. More preferably the sequence identity to the partial sequence of a wild-type tetraspanin is at least 80%, preferably at least 85%, 90%, 95% or 99% over the entire length. In a particularly preferred embodiment the domain (iii) consists of the aforementioned partial sequence of a tetraspanin or of a sequence homologous thereto.

The domain (ii) comprises a peptide with a predetermined amino-acid sequence. Herein this is also called "foreign peptide" or "foreign protein". The amino-acid sequence of the foreign peptide differs from the sequence of the large extracellular loop (LEL) of a wild-type tetraspanin, more particularly of the tetraspanin(s) of the domains (i) and (iii). In comparison with the LEL of a wild-type tetraspanin the sequence identity over the entire length is less than 70%, preferably less than 50%, more preferably less than 40% or less than 30%.

The amino-acid sequence in the domain (ii) can basically be selected at random. Irrespective of the sequence of the foreign peptide or of the domain (ii) a fusion protein according to the invention can be anchored and presented on the surface of cells, more particularly of mammalian cells (e.g. HEK293T-*Homo sapiens*).

Within the meaning of the present invention "peptide" denotes a combination of at least two amino-acids, which are linked together by way of peptide bonds. The length of the peptide is basically unlimited. Oligopeptides with up to 10 amino-acids, polypeptides with over 10 amino-acids and macropeptides with more than 100 amino-acids are all comprised. In a preferred embodiment the size of the peptide is less than 100 kDa, preferably less than 50 kDa or less than 30 kDa, for example 10-30 kDa.

Within the meaning of the invention the term "amino-acid" denotes preferably the amino-acids found in twenty naturally-occurring peptides, polypeptides and proteins that are in each case L-isomers. According to the invention, however, the term also includes analogues of the amino-acids and D-isomers of the amino-acids and their analogues.

Within the meaning of the invention the terms "peptide", "polypeptide" and "protein" are each used interchangeably. In a preferred embodiment the peptide is a protein with at least 50 amino-acids. For this it is preferable that the protein adopts a predetermined fold, which is required, for example, for a desired function of the protein.

In the domain (ii) the peptide with predetermined amino-acid sequence can comprise, for example, an antigen or an epitope of an antigen. Here "epitope" denotes a region of an antigen, to which an antibody or T-cell receptor binds specifically. A single antigen can comprise one or more epitopes. In one embodiment of the invention the peptide with predetermined amino-acid sequence comprises multiple epitopes, which are linked together by means of linkers. For example, they could be multiple epitopes of an antigen. Examples of epitopes are cancer epitopes, HIV epitopes (e.g. gp41 of HIV-1). Examples of these are V5-6×His (SEQ ID NOs: 35, 36) or 2F5-4E10 (SEQ ID NOs: 37, 38).

In a further embodiment of the invention the peptide with predetermined amino-acid sequence of the domain (ii) comprises a protein having a desired function, for example an enzyme, such as e.g. a protease.

In addition to the peptide with predetermined amino-acid sequence, the second domain (ii) can comprise one or more partial sequences of the LEL of a tetraspanin or sequences homologous thereto with a sequence identity of at least 70% over the entire length. Preferably the sequence identity is at least 80%, at least 85%, at least 90%, at least 95% or at least 99%. The partial sequences of the LEL of a tetraspanin can be disposed C- and/or N-terminally to the peptide with the predetermined amino-acid sequence. Preferably partial sequences of the LEL in the domain (ii) come from the same tetraspanin as the sequence segments of the domains (i) and (iii).

"Homologous", as used herein, describes the sequence similarity between two polypeptides, molecules or between two nucleic acids. If a position in both of the two compared sequences is occupied by the same base or amino-acid monomer subunit, the corresponding molecules in this position are homologous. The percentage homology between two sequences is the function of the number of matches or homologous positions shared by the two sequences divided by the number of positions compared multiplied by one hundred. For example, if 6 out of 10 positions in two sequences match or are homologous, then the two sequences are 60% homologous. Generally a comparison is made when two sequences are so aligned that the largest possible homology is obtained. Such alignment can be provided using, for instance, the method of Niedelman et al., J. Mol. Biol. 48: 443-453, 1970, implemented conveniently by computer programs.

Homologous sequences share identical or similar amino acid residues, where similar residues are conservative substitutions for, or allowed point mutations of, corresponding amino acid residues in an aligned reference sequence. In this regard, a "conservative substitution" of a residue in a reference sequence are those substitutions that are physically or functionally similar to the corresponding reference residues, e.g. that have a similar size, shape, electric charge, chemical properties, including the ability to form covalent or hydrogen bonds, or the like. Particularly preferred conservative substitutions are those fulfilling the criteria defined for an accepted point mutation in Dayhoff et al., "Atlas of Protein Sequence and Structure", 5: Suppl. 3, chap. 22: 354-352, Nat. Biomed. Res. Foundation, Washington, D.C., 1978.

The domains of a fusion protein according to the invention are disposed in each case in the order (i)-(ii)-(iii). Here the term "fusion" refers to a colinear coupling of the domains by way of their individual peptide backbones.

The domains (i), (ii) and (iii) can be bound optionally directly or by way of flexible linkers. In a first embodiment the domain (ii) adjoins the domain (i) directly. Alternatively or additionally the domain (iii) adjoins the domain (ii) directly.

In a further embodiment flexible linkers are disposed between the first and the second domain and/or between the second and the third domain. The linkers present can be the same or different. Exemplary linkers for use in the fusion proteins according to the invention comprise e.g. glycine polymers $(G)_n$, where n is a whole number of at least 1, glycine-alanine polymers and other flexible linkers that are known to the person skilled in the art. Essentially serine- and arginine-free linkers are preferred; serine- and arginine-free linkers are particularly preferred. Very particularly preferred is the linker LQEFDIGGGG (corresponding to SEQ ID NOs: 41, 42). Further linkers are described in FIG. 2C (see also SEQ ID NOs: 39, 40).

The domain (ii) can further comprise one or more recognition sequences, which can be split from an enzyme. Examples are recognition sites for specific proteases, nucleases or endoglycosidases. Alternatively the recognition site can comprise a substrate recognition site for a specific hydrolase enzyme, e.g. phosphatase, glycosidase, amidase or esterase. The term "protease recognition sequence" is used herein summarily for any recognition sequences that can be split enzymatically. These can be disposed C- and/or N-terminally to the peptide with the predetermined amino-acid sequence. In a particularly preferred embodiment the protease recognition sequences flank the peptide with the predetermined amino-acid sequence directly. As a basic principle any desired protease recognition sequences are suitable for this. If, apart from the peptide with predetermined amino-acid sequence, the second domain (ii) also comprises one or more partial sequences of the LEL of a tetraspanin, it is preferable in each case to insert the protease recognition sequences between the LEL partial sequence and the C- or N-terminus of the peptide with predetermined amino-acid sequence.

In a further embodiment a fusion protein according to the invention can additionally comprise a fourth domain (iv) on the N-terminus and/or a fifth domain (v) on the C-terminus of the fusion protein. The domains (iv) and (v) can in each case be bound directly or by way of flexible linkers, as defined above. For example the domain (iv) can be bound directly or by way of a flexible linker on the N-terminus of the domain (i). The domain (v) can be bound directly or by way of a flexible linker on the C-terminus of the domain (iii). Moreover it is possible to dispose protease recognition sequences, as defined above, between the domains (iv) and (i) and/or between the domains (iii) and (v) and, if present, between linker and one or more of the domains (i), (iii), (iv) and (v).

With regard to an anchoring of a tetraspanin in the plasma membrane of a cell, the C- and N-termini of the tetraspanin lie on the cytoplasmic side. The same applies analogously to a membrane anchoring of a fusion protein according to the invention.

The fourth and the fifth domain (iv) and (v) of a fusion protein according to the invention can be selected, for example, such that they comprise a marker group or what is known as a tag. Here "tag" denotes a short peptide sequence, for example a protein tag for marking and identification, e.g. a flash tag or the fluorescent reporter protein mCherry.

It was found that a fusion protein according to the invention differing from a wild-type tetraspanin at least owing to the domain (ii) nonetheless folds correctly, analogously to a wild-type tetraspanin. This was demonstrated using the example of the fluorescent proteins CFP and YFP in the domain (ii) (see FIG. 3B). Epitopes between the transmembrane domain TM3 and TM4 can be detected on the cell surface with an extracellular orientation with the help of scanning electron microscopy (FIG. 4). The introduction of epitopes between the TM3 and the TM4 of a tetraspanin and the transport to the cell surface with an extracellular orientation and epitopes on the N- and C-termini was demonstrated for the example CD63 by means of scanning electron microscopy (FIGS. 5A-5D). The successful protein expression of the fluorescent proteins was confirmed additionally by Western blot analysis. Here a specific band could be detected for the respective fusion proteins by way of the FLAG and mCherry epitope (FIG. 6). The localisation for further tetraspanins (CD9, CD81, CD82 and CD151) on the cell surface was shown likewise (FIG. 8). Furthermore it was shown that the use of low-serine and low-arginine linkers increases the efficiency of localisation on the cell surface (FIG. 10).

A further subject-matter of the present invention is a nucleic acid molecule that codes for a fusion protein according to the invention. A nucleic acid molecule according to the invention comprises a coding sequence segment for an aforementioned fusion protein or consists of this. This sequence segment is described herein also as "fusion gene". Particularly preferably a nucleic acid molecule according to the invention is present in isolated form.

A "nucleic acid molecule" within the meaning of the invention relates to a sequence of naturally-occurring nucleic acid bases, base analogues, base derivatives or combined forms of these. The term includes more particularly DNA and RNA and also nucleic acids derived from these such as, e.g., cDNA and mRNA. Within the meaning of the invention nucleic acid analogues such as PNA (peptide nucleic acid), LNA (locked nucleic acid), PSNA (phosphothioate nucleic acid) are also included among the nucleic acids. These nucleic acid analogues can, in principle, have the naturally-occurring nucleic acid bases, which are however linked together in a different way, as for example in DNA or RNA. Included among the nucleic acids are also nucleic acids having nucleic acid derivatives such as e.g. hypoxanthines, 2,5-diaminoporine and/or methylcytosine, and modified, more particularly marked, nucleic acids. Apart from base derivatives, these nucleic acid derivatives can, in principle, also have the naturally-occurring nucleic acid bases. Markings can be introduced on bases and/or backbone. The links can correspond to DNA or RNA or the nucleic acid analogues. The nucleic acids can be double-stranded or single-stranded, linear, branched or circular.

The present invention relates further to a vector comprising a nucleic acid molecule, as described above. Preferably the nucleic acid molecule is operably linked to an expression control sequence.

The term "expression control sequence" within the meaning of the invention comprises both elements that regulate expression at transcription level, like for example enhancers or silencers, and also elements that regulate expression at post-transcriptional level (e.g. splicing, nuclear export or mRNA stability). The term comprises also multiple elements that regulate expression at transcriptional and post-transcriptional level, and also combinations of transcriptional and post-transcriptional regulating elements. Techniques and aids for the identification of expression control sequences that lead to increased expression and to isolation of the same are routine techniques that are probably well-known to the person skilled in the art. The expression control sequence can more particularly be a promoter, preferably a eukaryotic promoter, such as e.g. a CMV or SV40 promoter; a prokaryotic promoter or phage-specific promoter, such as e.g. an SP6 or T7 promoter. Particularly preferably the promoter is a CMV promoter. The vector can additionally comprise a sequence segment for termination and/or polyadenylation of the nucleic acid molecule.

A vector according to the invention contains further preferably a selection marker gene, i.e. a sequence segment that codes for a selection marker. Examples of selection markers are antibiotic resistance or auxotrophy markers. Preferably an amplifiable selection marker gene, such as e.g. dihydrofolate reductase, is used. Optionally the vector according to the invention can comprise further an origin of replication.

Within the meaning of the present application the term "operably linked" describes a link of two or more nucleic acid sequences or partial sequences that are so positioned that they can perform their intended function. For example a promoter/enhancer is functionally linked to a coded gene sequence if it can control or modulate the transcription of the linked gene sequence in cis position. Generally, though not necessarily, functionally linked sequences are situated in close proximity and, if two coding gene sequences are linked or in the case of a secretion signal sequence, in the same reading frame. Although a functionally linked promoter is generally situated upstream of the coding gene sequence, it does not necessarily have to be closely proximate. Enhancers likewise do not have to be present in close proximity, as long as they facilitate the transcription of the gene sequence. For this purpose they could be present both upstream and also downstream of the gene sequence, possibly also some distance away. A polyadenylation site is functionally linked to a gene sequence, if it is positioned at the 3' end of the gene sequence, such that the transcription progresses by way of the coding sequence through to the polyadenylation signal. The link can come about in accordance with usual recombinant methods, e.g. by means of the PCR technique, by ligation at suitable restriction sites or by splicing. If no suitable restriction sites are present, synthetic oligonucleotide linkers or adapters can be used in a per se known manner. Preferably the functional link does not come about by way of intron sequences.

A vector according to the invention is preferably suitable for at least one (host) cell, more particularly for replication of the vector in this cell and/or for expression of a protein or peptide in this cell. Replication can take place in a prokaryotic and/or eukaryotic cell. Expression takes place preferably in a eukaryotic cell. The vector can be a plasmid.

Vector constructions for eukaryotic expression according to the prior art have as a rule a strong eukaryotic promoter that is as far as possible not cell-type-specific (e.g. the CMV or SV40 promoter) and a sequence part responsible for the transcriptional termination and the polyadenylation (e.g.

SV40 termination-polyA). Situated between these two elements is the CDS (coding sequence) to be expressed, headed by a more or less clearly defined Kozak sequence around the start codon. In the case of the vector construction according to the invention the CDS to be expressed is a gene from the tetraspanin super-family. Here all the tetraspanin genes from all organism species that have genes of this gene super-family which provide the desired transport capability over the membrane are in accordance with the invention. However, the fusion genes according to the invention are characterised by being able to possess at least one artificially introduced heterologous DNA sequence as internal and possibly terminal fusion. Terminal CDS fusions are heterologous DNA sequences that code 5'-proximally and/or 3'-distally to the tetraspanin gene for a fusion protein or a peptide. Between the third (TM3) and the fourth (TM4) transmembrane domain, according to the invention, internal, coding heterologous DNA sequences are introduced. The transmembrane domains of the tetraspanins are responsible, amongst other things, for the transport of the heterologous coding sequences to the membrane, the translocation through the membrane and the anchoring there.

An average person skilled in the art, who has been trained in molecular biology, will be able to produce functional DNA fusion constructs, possibly with the help of relevant literature[39].

More advanced vector constructions according to the invention should be emphasised particularly here. Instead of general eukaryotic promoters, these also possess bacterial and phage-specific promoters as well as eukaryotic cell-type-specific and organ-specific promoters that enable expression that is dependent on cell differentiation. Such promoter types can be employed, in order to use the gene constructs according to the invention irrespective of the application. Further vector embodiments according to the invention can also have for example RNA polymerase promoters of phages, in order to generate mRNA molecules very efficiently in vitro or possibly in vivo. Examples are the phage promoters, such as SP6- or T7-specific promoters for the production of mRNA molecules in vitro, so the fusion gene mRNA can possibly be supplied for therapeutic purposes and applications. This variant is welcomed as pharmaceutical form of regulators, because it is supposed to prevent the recombination of nucleic acids into the genome.

The expression of tetraspanin gene derivatives in bacteria or yeasts can be used to isolate the fusion proteins and be employed in man-made membranes. However, the eukaryotic differentiation- and cell-specific expression, for example in mucosa or muscle cells, can also be used to express DNA vaccines cell-specifically (see e.g. EP1390490 B1).

In authorisation procedures for therapeutic agents regulations have been established, which make such highly specific expression properties a mandatory requirement.

Furthermore vector systems according to the invention possess a specific design, which allows the expression of multiple fusion proteins in the same cell by means of a single vector construct (see patent application DE 10 2013 006 487 A9). With this design additional elements can be added in a simplified manner.

The subject-matter of the invention also concerns nucleic acids and vectors having a segment coding for a fusion protein, as defined above, wherein however, instead of a coding sequence for the peptide with predetermined amino-acid sequence, there is only a multiple cloning site present, which enables cloning of a gene coding for any desired peptide with predetermined amino-acid sequence by way of recognition sequences for restriction endonucleases. Additionally multiple cloning sites can be present in 5' and/or 3' position for N- and/or C-terminal domains (iv) and (v).

One aspect of the invention therefore concerns a nucleic acid molecule comprising a first sequence segment (i), a second sequence segment (ii) and a third sequence segment (iii), wherein the second sequence segment is disposed between the first and the third sequence segment, wherein
  (i) for a partial sequence of a tetraspanin, which includes the transmembrane domain 1 (TM1), the small extracellular loop (SEL), the transmembrane domain 2 (TM2), the small intracellular loop (SIL) and the transmembrane domain 3 (TM3), or codes a sequence homologous thereto with a sequence identity of at least 70% over the entire length,
  (ii) comprises a multiple cloning site and
  (iii) codes for a partial sequence of a tetraspanin, comprising the transmembrane domain 4 (TM4) or a sequence homologous thereto with a sequence identity of at least 70% over the entire length.

Here the sequence segments (i) to (iii) are preferably disposed from 5' to 3'. A "multiple cloning site" comprises multiple restriction sites, lying one behind the other, for restriction endonucleases. The multiple cloning site is more particularly suitable for integration of a nucleic acid molecule, wherein the integrated nucleic acid molecule in the reading frame codes with the first sequence segment (i) and the third sequence segment (iii) for a peptide that is to be presented. The peptide comprises preferably a predetermined amino-acid sequence, having a sequence identity of less than 70% over the entire length in relation to the large extracellular loop (LEL) of a tetraspanin.

The present invention concerns further a vector comprising an aforementioned nucleic acid molecule, preferably operably linked to an expression control sequence.

In the prior art numerous recognition sequences are known for the most varied restriction endonucleases and also the restriction endonucleases relevant here. Preferably sequences are used that consist of at least six nucleotides as recognition sequence. A listing of suitable identification sequences can be found for example in Sambrook et al. (1989).

Specific sequence elements of a vector according to the invention with multiple cloning site concern the bringing-in of heterologous DNA sequences onto the corresponding terminal and internal, functionally acceptable positions of the tetraspanin genes (such as e.g. CD63) themselves. Thus time and time again one can insert new epitope CDS into the "unique", i.e. individual, restriction sites or various genes and gene fragments additively in a cyclic reaction into existing vector constructs. An example is provided in FIG. 2A, SEQ ID NO: 1 by the vector pAE211 according to the invention. Restriction sites are positioned at the position between the transmembrane domains TM3 and TM4. For this position it has been shown experimentally that it is particularly suitable for fusion with heterologous DNA sequences that code for a heterologous peptide, because it does not interfere with the function of membrane transport. At this site there is situated a protein loop that stands out over the membrane, the sequence of which can be variable without interfering significantly with the protein transport to the plasma membrane of the tetraspanin protein in cell cultures.

The 5-terminal CDS fusion, to generate an N-terminal fusion protein, can be brought in by means of two NcoI in the 5' region of the CD63 gene, such that the Kozak sequence is regenerated in the start region. This is unique.

The possible 3'-terminal CDS fusion element, which leads to a C-terminal protein fusion, is inserted by means of the type-IIS restriction endonuclease BsaI, which generates specific ends for NdeI and BclI in the construct. These sites also can possibly be used to insert 3'-terminal gene fusion elements.

The above realisations of vector systems are examples and any other method or technology for modifying the vectors, apart from the described restriction-ligation method, is equally according to the invention, such as for example the sequence modulation of the systems by means of suitable recombination systems, in vivo as well as in vitro.

A further subject-matter of the present invention is a cell comprising a nucleic acid molecule according to the invention or a vector according to the invention.

In an embodiment according to the invention the nucleic acid molecule or the vector comprising a sequence coding for a fusion protein and suitable genetic control functions is integrated genomically stably or is present extra-chromosomally in the cells and a fusion protein according to the invention is expressed there constitutively or inducibly or repressibly.

A cell within the meaning of the present invention is preferably a eukaryotic cell, preferably a mammalian cell, such as more particularly a humane cell. Further examples of suitable mammalian cells are cell lines of rodents such as e.g. mouse, rat and hamster cells, or ape cells. A nucleic acid molecule according to the invention or a vector according to the invention can be brought into a cell, more particularly a eukaryotic cell, with the help of per se known techniques. The successful transfection results in transformed, genetically modified, recombinant or transgenic cells.

The transfection of eukaryotic host cells with a nucleic acid molecule according to the invention or a vector according to the invention comes about in accordance with usual methods (Sambrook et al., 1989; Ausubel et al., 1994). Suitable transfection methods are e.g. liposome-mediated transfection, calcium phosphate co-precipitation, electroporation, polycations, (e.g. DEAE-dextran)-mediated transfection, protoplast fusion, microinjection and viral infections. According to the invention the cells are obtained preferably by way of a stable transfection, wherein the constructs are either integrated into the genome of the host cell or an artificial chromosome/mini-chromosome or are contained in a stable manner episomally in the host cell. The transfection method that enables the optimal transfection frequency and expression of the heterologous gene in the respective host cell is preferable for this. By definition each sequence or each gene that is brought into a host cell is described as "heterologous sequence" or "heterologous gene" in relation to the host cell, even if the sequence being brought in or the gene being brought in is identical to an endogenous sequence or an endogenous gene of the host cell.

In an embodiment according to the invention the cells can be cells of transgenic cell unions of various cell types, in which a fusion gene according to the invention is also expressed in different cellular differentiation states. These cells can be generated ex vivo and possibly be used thereafter therapeutically in vivo.

In a further embodiment according to the invention the cells are cells of cell unions of transgenic organisms, the cells of which have passed through the germ line and have developed into multicellular systems, preferably into vital organisms.

In a preferred embodiment a cell according to the invention was furthermore transformed or transfected with at least one further nucleic acid molecule or at least one further expression vector. The further nucleic acid molecule or the further expression vector preferably contains a segment that codes for a further predetermined protein. The further nucleic acid molecule or expression vector can, according to one embodiment, likewise be a nucleic acid molecule according to the invention or an expression vector according to the invention, wherein in this case another peptide with another predetermined amino-acid sequence was selected for the domain (ii). In another embodiment the further nucleic acid molecule or the further expression vector contains a segment that codes for an enzyme, for example for a protease. If in such a cell the nucleic acid molecule according to the invention and the further nucleic acid molecule are expressed, both the peptide of the domain (ii) with predetermined amino-acid sequence and also the further protein are presented on the membrane surface. If for example the peptide of the domain (ii) is flanked by protease recognition sequences, a protease expressed by way of the further nucleic acid molecule could cut on these recognition sites and thus release the peptide.

According to the invention the host cells are preferably established, adapted and cultivated under serum-free conditions, possibly in media that are free of animal proteins/peptides.

A further subject-matter of the present invention is a membrane preparation that was obtained from a cell according to the invention.

A membrane preparation within the meaning of the invention comprises at least an isolated membrane, more preferably an isolated, cellular membrane, even more preferably an isolated, cellular plasma membrane and/or an isolated, cellular membrane of other cell organelles. The term "membrane" within the meaning of the present invention describes a self-contained system comprising at least one lipid and optionally at least one protein. The lipids of a membrane usually form a lipid bilayer. The membrane preparation comprises preferably membrane particles, more preferably membrane vesicles.

The membrane preparation can be obtained from a cell according to the invention by means of methods known to the person skilled in the art, preferably by means of lysis of the cell (cell lysate), more preferably by means of lysis of the cell and subsequent isolation and optionally cleaning of the cellular membrane (isolated and optionally cleaned membrane). Optionally surfactants, such as e.g. Triton X-100, can be used to solubilise the membranes. The method can additionally contain a step for removing cell debris. The diameter of the membrane particles can be in the range 1-1000 nm, preferably 50-500 nm, more preferably 75-200 nm. At least 80%, at least 90%, at least 95% or at least 98% of the membrane particles have a diameter in one of the ranges described herein.

A membrane preparation according to the invention is obtained from a cell according to the invention comprising a nucleic acid molecule according to the invention or a vector according to the invention. In the cell the fusion protein according to the invention is expressed by means of the nucleic acid molecule or the vector. A membrane preparation according to the invention therefore comprises preferably at least an isolated membrane and at least a fusion protein according to the invention. Here the fusion protein according to the invention is preferably anchored in the membrane, more preferably on the surface of the membrane, more particularly on the extracellular side of the membrane. The fusion protein according to the invention is presented on the membrane, preferably on the surface of the membrane, more particularly on the extracellular side of the membrane.

The membrane preparation can optionally additionally comprise one or more wild-type tetraspanins.

In one embodiment the membrane systems according to the invention are the outer membrane of cells, e.g. of in-vitro cell cultures, in which at least a fusion protein according to the invention is expressed transiently.

The present invention concerns further a synthetic membrane system comprising a membrane and a fusion protein, a nucleic acid molecule or a vector as described above.

The membrane can be a cellular (natural) or synthetic (man-made) membrane. A cellular membrane is more particularly a cellular plasma membrane, which is typically situated on the surface (outer layer) of a cell. A cellular membrane within the meaning of the present invention can be part of a cell, or have been isolated from a cell, i.e. be an isolated, cellular membrane. A cellular membrane is typically asymmetrical and has a side facing towards the cytoplasm (plasmic or intracellular side, inner side) and a side facing away from the cytoplasm (extraplasmic or extracellular side, outer side).

A synthetic membrane can comprise synthetic and/or isolated, cellular membranes. More particularly the lipid and/or protein composition of synthetic membranes can differ from the naturally-occurring compositions of cellular membranes. A synthetic membrane is preferably not part of a cell and is present more particularly as isolated, synthetic membrane. The person skilled in the art can influence the properties of a synthetic membrane through the choice of lipids and/or proteins.

In one embodiment a synthetic membrane system comprising a nucleic acid molecule according to the invention or a vector according to the invention contains additionally a system for expression of the nucleic acid molecule or of the vector, by means of which the fusion protein can be expressed. Systems for the expression of proteins are known in the prior art and are preferably cell-free. The system for expression preferably comprises a system for translation of a nucleic acid molecule, more particularly of an RNA or mRNA; and, optionally a system for transcription of a nucleic acid molecule or of a vector, more particularly in order to obtain an RNA or mRNA.

In an alternative embodiment the fusion protein can be added directly to the membrane, in order to obtain a membrane system according to the invention.

In the case of a membrane system the expressed or added fusion protein is anchored in the membrane, preferably on the surface of the membrane, more particularly on the outer side of the membrane. The fusion protein according to the invention is presented on the membrane, preferably on the surface of the membrane, more particularly on the outer side of the membrane.

It was found that also in a synthetic membrane system the fusion proteins according to the invention can be directed and translocated to the surface and anchored there. In this case it is possible to incorporate artificial, non-canonical amino-acids into the fusion proteins according to the invention in vivo or in vitro. Using cell-free protein synthesis it would be possible to obtain fusion proteins that are suitable also for populating synthetic membranes and to be present there anchored.

A further aspect of the present invention is a method for the presentation of a peptide with a predetermined amino-acid sequence on the surface of a cell comprising the steps
(a) provision of a cell according to the invention, as described above, and
(b) cultivation of the cell under conditions where a fusion protein according to the invention is expressed.

The present invention concerns further a method for the anchoring of a peptide with a predetermined amino-acid sequence on a membrane comprising the steps
(a) provision of a membrane, and
(b) bringing into contact of the membrane with a fusion protein, as described above, under conditions where anchoring of the fusion protein takes place in the membrane or bringing into contact of the membrane with a nucleic acid, as described above, or a vector, as described above, under conditions where the fusion protein is expressed and anchored in the membrane.

A further subject-matter of the invention is the use of an aforementioned cell, a membrane preparation or a synthetic membrane system in a method for the screening for interaction partners of the peptide, for the study of interactions of the peptide with interaction partners (e.g. antibodies), in a method for the production of the peptide, as immunisation reagent in a method for antibody production and/or as detection reagent.

The present invention concerns furthermore a cell, membrane preparation or a synthetic membrane system, as described above, for use as vaccine and/or as medication.

In an embodiment according to the invention the fusion proteins are removed from the transfected, transiently or stably expressing cells, transgenic organisms or synthetic membrane systems, in order to be put to use in research and development, and also possibly to be supplied as part of a method or kit for a commercialisable application. Examples are the production of bioanalytical-diagnostic systems and therapeutic agents.

In a further embodiment according to the invention the membranes containing the fusion proteins are removed from the cells, transgenic or synthetic membrane systems, in order to be put to use in research and development, and also possibly to be supplied as part of a method or kit for a commercialisable application. Examples are the production of bioanalytical-diagnostic systems and therapeutic agents.

The expressed fusion proteins of the present invention are shown on the cell surface of transfected cells as stationary reactants and can be used for the analysis of specific interactions with other molecules. Here for one thing protein-protein interactions (e.g. mono- or polyclonal antibody paratope-epitope interactions, coiled-coil interactions and many specific interactions of pharmaceutical-medicinal, more particularly also molecular-mechanistic significance) are interesting. Tetraspanin fusion molecules can also be utilised for the analysis of interactions with other molecules, such as mono- and polysaccharides, RNAs, DNA and more particularly with small chemical molecules such as natural substances and chemical substance libraries.

The expression of multiple tetraspanin fusion molecules or protein variants of a protein species in a cell is just as interesting for certain experimental preparations as the combinatory use of various interacting proteins.

In one embodiment of the invention a cell according to the invention expresses a protein domain (A) that is able to interact very specifically with another protein domain (B). Here the protein domain (A) corresponds to the peptide with predetermined amino-acid sequence of the domain (ii) of a fusion protein according to the invention.

This external protein domain could then be bound with various functional further protein domains. For all these protein domain modules one could ensure that these—if they are of exogenous origin—bind specifically onto the counter-domain (A) of the expressing cell and thus the protein ligands can be replaced, which for their part could bind again and thereby a coexistence of various protein modules mediated by specific interaction could be detected on the cell surface.

Preferred examples of the application of the fusion proteins, vectors, cells and membrane systems according to the invention are to be described in more detail below.

Analysis of Protein-Protein Interactions (PPI)

Fixed proteins accessible on surfaces can establish specific contacts to further proteins by means of particular structures on the surface of the respective proteins. These further proteins can be the protein building blocks of homo- and heteroprotein complexes, which can recognise each other, or also specific proteins, such as antibodies and single chains, which can bind specifically and in a targeted manner to certain protein surface structures. Genomically coded naturally-occurring proteins that enter into specific interactions with other proteins perform many cellular functions—from functions in the cell nucleus through to diverse cytosolic and membrane functions. These specific and functional protein-protein interactions (PPI) emerged over the course of evolution and are responsible to a crucial extent for the integrity of the cellular function. Targeted PPI is mediated by cellular processes and the selection of protein variant, which have a specific interaction with surfaces. The immune system is designed for the sensitive reactions against the change of the surfaces within an organism and specialised in the optimisation of surface interactions of antibodies and cytotoxicity in very short periods of time. In humoral immunity large quantities of epitope-specific, polyclonal antibodies are produced in a short time. The particular single-chain antibodies of camelids (single chains) and other naturally-occurring immunogenic systems that develop highly specific protein interactions have become known.

In medical research these processes for generating monoclonal antibodies have been implemented technically by means of cell culture technologies and in this way the generation of specific PPI in vitro has been made possible.

Antibody engineering uses man-made paratopes produced by means of display technologies (ribosome display, phage display, yeast display) that can recognise epitopes specifically, in order to incorporate these in antibody molecules. The efficient export functions for protein units of the tANCHOR system described here and their anchoring in the membrane are suitable to a high degree for PPI analyses. In addition proteins specifically modified with sugars can be presented on cell surfaces by means of the tANCHOR technology.

Detection systems, with which the averagely qualified person skilled in the art is able to identify a specific PPI, are offered commercially as cell sorting systems (FACS), fluorescence- or bioluminescence-based imaging systems and also as FRET photonic instruments. Mass spectroscopic analysis would also be an excellent possibility as analytical tool.

Just the cellular system used makes the quality of the data being generated and the decisive difference. It is—comparable with resolution in optics—the decisive parameter for all further process steps that defines the quality of the data obtained at the end of the process chain.

The tANCHOR system is suited in a particular way for providing display functions for bioanalytical-diagnostic applications and also for therapeutic agents. With this system the integrity of protein structures can remain structurally intact with the retention of, for example, structural epitopes, as can also that of binding domains in the PPI of cellular regulator proteins between each other.

Analysis of Small Molecules with tANCHOR Constructs

By means of structurally intact protein structures it is possible additionally to carry out interaction studies of the binding of, and also displacement from, a PPI binding by the small molecules with the proteins presented on the cells. Interesting interactions of small molecules are ones which interfere with PPIs and in which certain protein aggregates could be dissolved again under the influence of the small molecules are identified. PPI analyses are particularly well suited for the discovery and development of small molecule active ingredients.

The tANCHOR technology offers an excellent tool for this, making protein expression available with simultaneous anchoring of the proteins on the cell surfaces. In conjunction with suitable protein pairs from a further expression source or possibly also through the co-expression of various tANCHOR molecules it is possible to establish therefrom test systems for the analysis of interactions of small molecules with protein complexes[1,40-48].

Furthermore the segments of the fusion proteins according to the invention localised on the cell surface could be cleaved specifically at a designated site by means of possibly inducible co-expression of highly-specifically cleaving secreted proteases (e.g. the TEV protease) and thus brought into solution. The defective fusion proteins could be replaced constantly in a resynthesis cycle in the membrane and thereby also ensure lasting overexpression.

Small molecules (e.g. from extracts of organisms expressing secondary metabolites) could thus bind onto the proteins according to the invention and identify these as target.

In the resulting complexes of small molecules and presented protein segments according to the invention the small molecules can be bound either specifically to the target peptides fixed on the cell surface or to the already cleaved target peptides present in solution as carrier peptides.

The resulting complexes and thereby the small molecules and their binding partners could then be identified by means of mass spectroscopy. For example in the case of non-peptidic small molecules these could be identified after isolation of the complexes present in solution and destruction of the peptides, e.g. by means of non-specific enzymatic proteolysis etc., by means of mass spectroscopy.

Development and Production of Immunodiagnostic Devices

In accordance with one embodiment of the invention interesting applications are ones in which antibodies are to be tested in a certain format, e.g. the standardised 96-well format, for the binding with epitopes exposed with tANCHOR. By means of the system according to the invention, for example, cells are seeded out in microtitre plates with the 96-well format and the fusion constructs are expressed in transiently transfected state. This is also possible with stable cell lines expressing fusion proteins.

As an example the use of the tANCHOR system is shown for the detection of antibodies in ELISA experiments (FIG. 9).

The fusion proteins are found on the cell surfaces and are presented there. This artificial configuration of the membrane can be implemented directly for the development and production of analytical and therapeutic applications.

In this way analytical systems can be produced, in which e.g. suitable blood sera of patient cohorts appropriate to the particular application being developed can be tested for clinical studies. For the development of immunodiagnostic devices and therapeutic agents, more particularly also for companion diagnostics, it is possible with such systems to examine the patient serum qualitatively and quantitatively for the presence of antibodies and their binding properties.

Furthermore it is possible to fix and dry microtitre plates and other formats, in which transgenic cells have grown, in order to manufacture bioanalytical test systems and diagnostic devices with them on a large scale and to produce these on a large scale.

Moreover it is also possible to use membranes of transgenic organisms that express tetraspanin protein fusion products and to purify these. Likewise man-made membranes containing fusion products according to the invention can also be supplied to such uses, as described above.

The cost saving here is immense, because there is no comparatively expensive coating with peptides or expressed and purified proteins.

Obtaining of Pure Protein

In research and development, and also in larger-scale production, the obtaining of sufficient quantities of target proteins with high specific activity by means of their expression is still a challenge, more particularly if one would like to purify the proteins in a functional fold state and possibly modified form. For this it is advantageous to use the system according to the invention. This can be of great advantage, because the localisation of the desired target protein outside the cell, in the medium, is a very much less complex environment than cytosol within the cells. Accordingly it is easier to enrich and to isolate. Normally the expressed proteins are to be found intracellularly and are purified out of the cytosol.

In one embodiment of this use according to the invention the cleaving of membrane-anchored protein expressed with tANCHOR can be cleaved off from the membrane by means of proteinases specific to the amino-acid sequence motif. The specific proteases can on the one hand be supplied exogenously to the medium or be co-expressed endogenously with the target protein. This procedure would perhaps require the proform of a sequence-specific endoprotease that is activated in the medium. In a prolonged cultivation of the cells with the aim of isolating the protein the enrichment of specific target protein takes place finally in the medium, because the target protein released by tANCHOR continues to be supplied constantly into the membrane owing to the loss of integrity of the protein.

DNA Vaccination as Therapeutic Application

In conjunction with differentiation-specific and/or species-specific promoters (including in the veterinary sector), which find their expression only in very specific target cells, the tANCHOR system is able, owing to the efficient membrane transport, to express heterologous gene fusion elements even in the intact cells of an organism. These can be brought exogenously into cells. For inoculation with DNA or RNA molecules it is possible to fire tetraspanin fusion constructs directly at cells at high speed by means of what are known as "gene guns" or "particle guns" and to induce the transfected cells hit to express fusion protein transiently. These proteins can be antigens or subspecific antigenic determinants, epitopes, which were previously tested for their suitability. The tANCHOR technology can be used both for the provision of diagnostic bioassays suitable for this purpose, and also for therapeutic vaccination.

It is discussed that DNA could integrate into the genomes of cells hit with gene particles and could possibly cause damage there through integration e.g. into a tumour repressor gene. Practice teaches, however, that very extensive homologous gene regions accompanying the gene constructs according to the invention are necessary, in order to really generate a higher and relevant integration rate. Such elements are not envisaged in the constructs according to the invention. However, the mRNA vaccines are on the way up owing to such chains of association relating to the danger of DNA vaccinations on the part of sensitive regulators. Thus according to the invention it is also possible, for example by means of in-vitro transcription, to generate mRNA molecules that are optimised for expression in eukaryotic cells, to stabilise these and fix these on nanobeads or pack them into suitable micro- to nano-compartments (virus-like particles, VLPs) and supply the mRNAs in this form for therapeutic applications.

Because of the specific properties of the tetraspanin fusions the proteins thus expressed are transported onto the cell membranes of the expressing cells and shown there to the outside.

The exposure of specific amino-acid sequences can be recognised by the immune system and there bring about corresponding, desired immune responses humoral or cytotoxic immune responses.

Therapeutic Applications Using Isolated Cells or Cell Membranes

Additionally it is possible—ideally because of the HLA incompatibility groups and possible adverse immune responses associated with them—to transfect even autologous cells in vitro after ex-vivo extraction, possibly after or during an intermediate cultivation phase. The transfection of autologous cells of test subjects (e.g. humans, but also animals) with DNA constructs based on the tANCHOR system will enable these to be brought into use in autologous or autogenous vaccinations. In this connection the use of intact autologous cells that have been tested for quality and also of isolated cell membranes from such cells is possible. These can be obtained for example through density gradient ultracentrifugation. Here the ratio of epitope to total protein can be improved and thereby contribute to increasing the specific activity of an immune response. Non-specific concomitant responses and auto-immune responses are reduced.

The combination of expressed adjuvants, which can possibly be co-expressed in a cell with multiple tANCHOR constructions, is a variant that is also within the range of possibilities for improvement in the application of tANCHOR systems according to the invention.

The co-expression of various proteins that improve the physico-chemical properties, e.g. the solubility of membranes, could improve considerably the membranes isolated from the cells for a vaccination. Natural adjuvants could also help to improve the vaccination response through co-expression with CD63 antigen/epitope fusions.

A further subject-matter of the invention is a kit comprising (i) a nucleic acid molecule or a vector as described above and (ii) a cell or membrane.

Additionally, depending on the intended application, a kit according to the invention can contain various components such as e.g. control plasmids, control proteins or similar items and special plasmids for various applications.

The present invention is to be described in more detail by way of the figures and examples below.

(A) Positions which, according to prior art, can serve various applicative problem-solving approaches with fusions and insertions. The system according to the invention, described also as tANCHOR system, consists of four transmembrane domains (4TM). DNA sequences coding for epitopes or proteins can be cloned in between TM3 and TM4. As an example, the epitope FLAG tag was implemented on the N-terminal end and, for example, the fluorescent protein mCherry was implemented additionally as transfection control on the C-terminal end of CD63 in the tANCHOR system through gene fusion (see also FIG. 2). (B) With the tANCHOR system developed for the STATUS QUO, epitopes or antigens expressed by human cells can be found clearly, localised on the plasma membrane. The tANCHOR system is able with high efficiency to direct the fusion proteins to the plasma membrane and anchor them there.

Figure 2A:
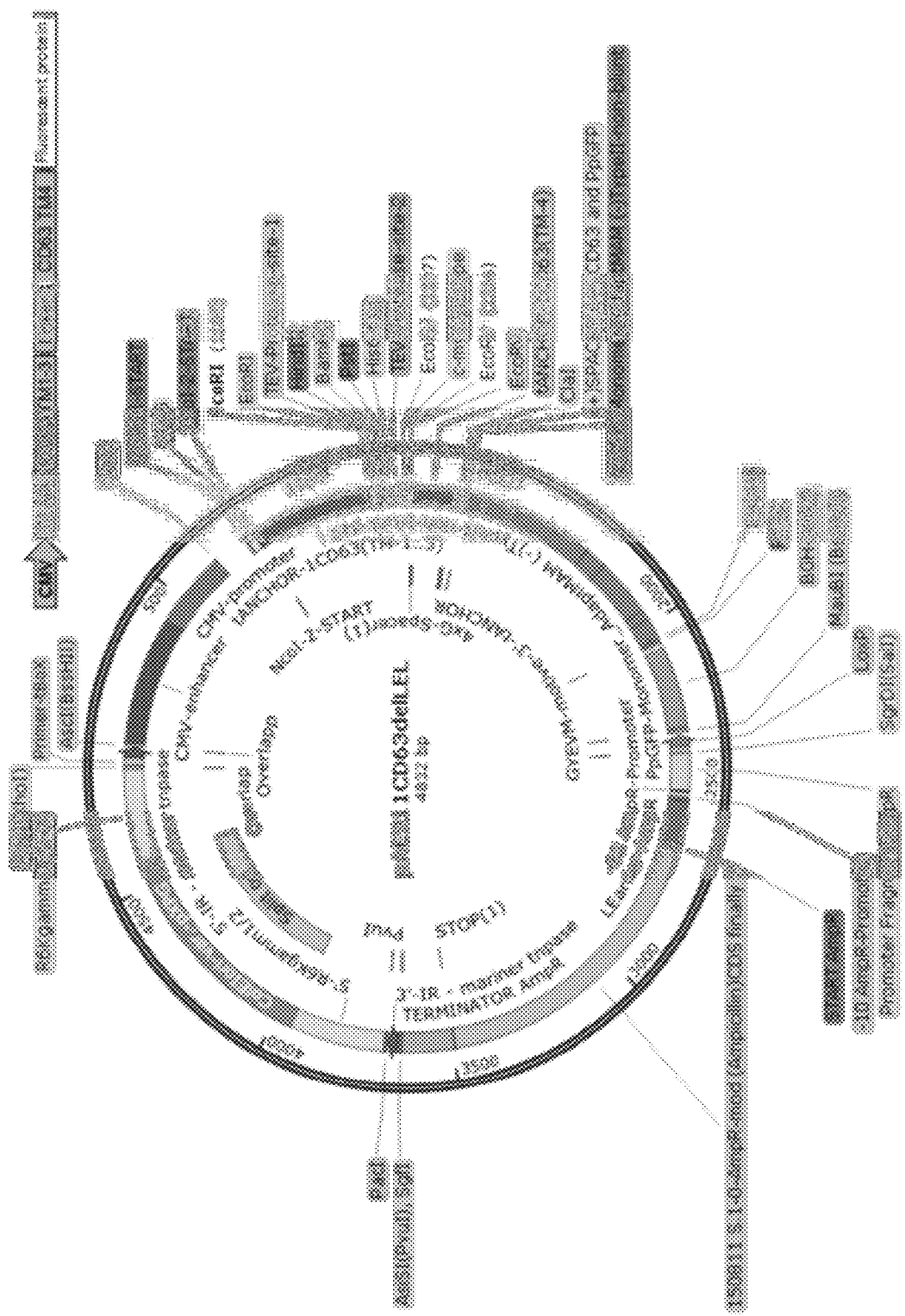

FIG. 2A: Schematic structure of the exemplary tANCHOR vector system.

The first exemplary tANCHOR vector system builds on the modular multi-expression vector pA4E211 (SEQ ID NO: 1) and functional derivatives of this vector. Represented additionally is an overview of the sequence arrangement of the CD63ΔLEL components (FIG. 2B) and also the N-terminal fusion of the FLAG epitope and also C-terminal fusing of the fluorescent reporter protein such as e.g. mCherry or GFP from *Pontellina plumata*.

| Feature/Name | Feature/Type | Position |
| --- | --- | --- |
| AbsI(XhoI) | R sites | 1 . . . 8 |
| Primer-tBoX | PCR-primer sequence | 11 . . . 31 |
| 5'-IR Mariner-tnpase IR-3' | Recombination site | 33 . . . 59 |
| AscI(BssHII) | R sites | 63 . . . 70 |
| CMV enhancer | Eukaryotic transcriptional enhancer | 71 . . . 429 |
| CMV promoter | Eukaryotic transcriptional promoter | 436 . . . 633 |
| SacI | R site | 634 . . . 639 |
| NcoI-1-START | R site | 732 . . . 737 |
| FLAG | Immune marker/proteolytic site | 738 . . . 761 |
| NcoI-2-START | R site | 762 . . . 767 |
| tANCHOR-1CD63(TM-1 . . . 3) | Transmembrane domain 1-3 of CD63 | 767 . . . 1099 |
| EcoRI | R site (integration site of fusion protein) | 1100 . . . 1105 |
| TEV protease-site-1 | Specific proteolytic site | 1106 . . . 1126 |
| HindIII | R site | 1127 . . . 1132 |
| BamHI | R site | 1133 . . . 1138 |
| PstI | R site | 1139 . . . 1144 |
| His6-tag | R site | 1145 . . . 1162 |
| TEV protease-site-2 | Specific proteolytic site | 1163 . . . 1183 |
| c-myc epitope | Immune marker | 1184 . . . 1197 |
| EcoRV | R site (integration site of fusion protein) | 1214 . . . 1219 |
| 4 × G spacer | 4 × glycin spacer improves membrane translocation, insertion and folding | 1220 . . . 1230 |
| tANCHOR-1CD63(TM-4) | Transmembrane domain 4 of CD63 | 1220 . . . 1345 |
| GYEVM-motive-3'-tANCHOR | Putative lysosomal-targeting/internalisation motive of CD63 | 1331 . . . 1345 |
| C/aI | R site | 1352 . . . 1357 |
| (+)SPACER bw. CD63, PpGFP | SPACER sequence | 1361 . . . 1369 |
| PpGFP-Monomer AdaptMAM-CDS START | Translational START codon | 1373 . . . 1375 |
| BcI sensitive methylation | R site | 2045 . . . 2047 |
| PpGFP-Monomer AdaptMAM-CDS | (−)Typell-non-blunt-palindromisc feature | 1376 . . . 2047 |
| PpGFP-Monomer_AdaptMAM_STOP | Translational STOP codon | 2045 . . . 2047 |
| BspHI | R site | 2048 . . . 2053 |
| PmeI | R site | 2056 . . . 2063 |
| BGH-polyA | Polyadenylation site | 2076 . . . 2300 |
| SgfI | R site | 2309 . . . 2312 |
| MauBI(BssHII) | R site | 2307 . . . 2314 |
| LoxP | Lox recombination site | 2323 . . . 2356 |
| SgrDI(SalI) | R sites | 2365 . . . 2372 |
| Promoter Fragment | DNA fragment with promoter | 2373 . . . 2475 |
| AmpR-Promoter-35 | Promoter function | 2476 . . . 2481 |
| AmpR-Promoter-10 | Promoter function | 2494 . . . 2502 |
| Leader-AmpR | Transcriptional leader sequence | 2507 . . . 2634 |
| AmpR-gene | Translational START codon | 2635 . . . 2637 |
| AmpR-CDS_mod | Resistance gene AmpR | 2638 . . . 3492 |
| AmpR-gene STOP | Translational STOP codon | 3493 . . . 3495 |
| AmpR term | Transcriptional terminator | 3495 . . . 3640 |
| AsiSI(PvuI), | R site | 3641 . . . 3648 |
| 3'-IR mariner tnpase | Recombination site | 3652 . . . 3678 |
| PacI | R site | 3681 . . . 3688 |
| 5'-R6Kgamm1/2 | Split Ori (for cloning) | 3689 . . . 3953 |
| Split ori | Ori (composed of two ori) | 3954 . . . 4569 |
| ColElori-var.-pXPG | pXPGderivative ori | 3954 . . . 4569 |
| R6Kgamma1/2-3' | Split Ori (for cloning) | 4570 . . . 4832 |

Figures 2B, 2C:
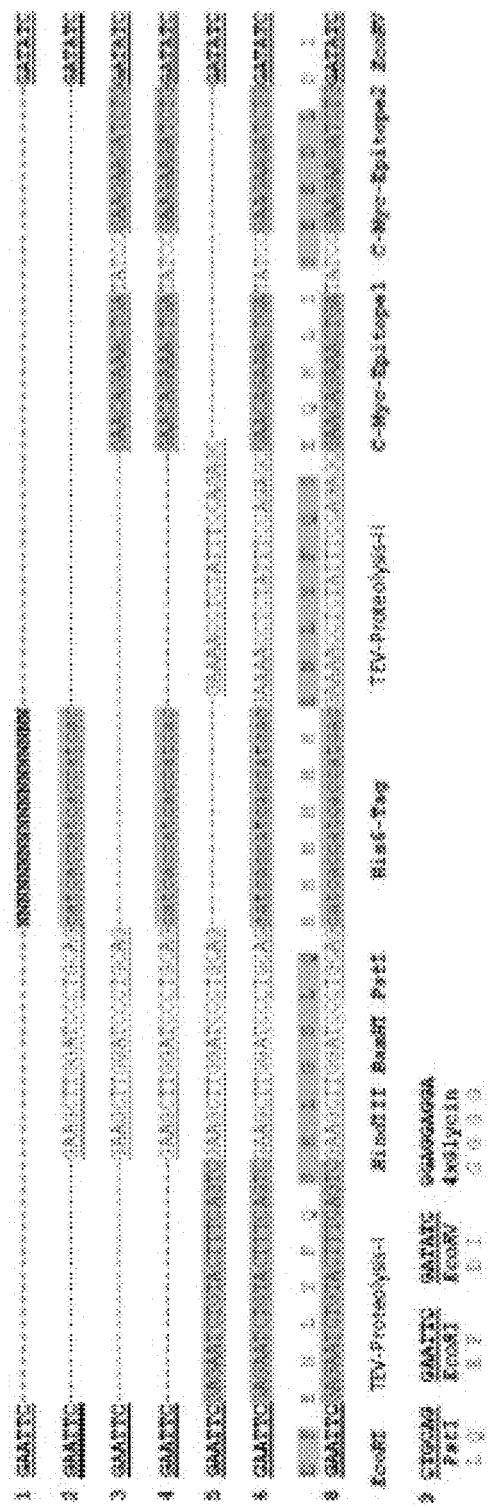

FIG. 2B: Derivation of the CD63ΔLEL sequence (SEQ ID NO: 3) from the coding wild-type (WT) sequence of CD63 (SEQ ID NO: 17).

The wild-type CD63 protein sequence consists of 238 amino-acids. For the generation of CD63ΔLEL the coding DNA sequence of the transmembrane domains 1-3 and 4 (underlined sequence CD63 TM1-3, CD63 TM4) was used. The linker, which does not contain the sequence for the LEL of CD63 (ΔLEL), is placed between the fragment CD63 TM1-3 and CD63 TM4 (SEQ ID NO: 42). Additionally the GGGG structure motif in the linker is inserted. A gene sequence (SEQ ID NO: 45) for a linker with the amino-acid sequence KLIDTVDLEK (SEQ ID NO: 46) can be comprised between the gene sequence CD63ΔLEL and the gene sequence for the fluorescent protein.

Table 2 to FIG. 2A: Linear organisation of the modularly structured tANCHOR Kit vector systems, type-I series: pA4E211

(0) AbsI-AscI-|FLAG|CDXX:Epitope |Reporter |-MauBI-SgrDI-SELECTORS-AsiSI-PacI
(1) AbsI-AscI-|FLAG|—:—|—|-MauBI-SgrDI-Puromycin R-AsiSI-PacI
(2) AbsI-AscI-|FLAG|CD63:— |—|-MauBI-SgrDI-Puromycin R-AsiSI-PacI
(3) AbsI-AscI-|FLAG|CD63: gp41 |—|-MauBI-SgrDI-Puromycin R-AsiSI-PacI
(4) AbsI-AscI-|FLAG|CD63: eYFP |eGFP-gene |-MauBI-SgrDI-Puromycin R-AsiSI-PacI
(5) AbsI-AscI-|FLAG|CD63:bioPepID|eGFP-gene |-MauBI-SgrDI-Puromycin R-AsiSI-PacI
(6) AbsI-AscI-|FLAG|CD63:bioPoiID| YFP-gene |-MauBI-SgrDI-Puromycin R-AsiSI-PacI
(7) AbsI-AscI-|FLAG|CD63:bioPoiID|POI-FusionI-MauBI-SgrOI-Puromycin R-AsiSI-PacI Positive and negative control vectors for the tANCHOR CD63 protein presentation system (display system). (0) Formal representation of the functional elements of the tANCHOR technology: CDXX-(=various tetraspanin protein species) CDS (=coding sequence) (1) tANCHOR vector without CD63 gene, the internal CD63 insertion and the terminal reporter (2) tANCHOR vector with the CD63 gene, without internal CD63 insertion and terminal reporter of the tANCHOR vector with CD63 gene and with e.g. FLAG tag epitope as internal CD63 insertion and no terminal reporter (3) tANCHOR vector with the CD63 gene, and the gp41 epitope as internal CD63 insertion and also the terminal reporter of the tANCHOR vector with CD63 gene (4) tANCHOR vector with e.g. CD63 gene and the YFP epitope as internal CD63 insertion and with the C-terminal reporter GFP (e. green fluorescent protein gene). (5) tANCHOR vector with e.g. POI-bioPepID epitope(s) (protein/peptide of interest), used for analysis, as internal CD63 insertion and with the C-terminal reporter eGFP (e. green fluorescent protein gene), as well as (6) with additional reporter genes, such as YFP (yellow fluorescent protein gene) and with fusions of the protein of the relevant experimental interest (POI fusion). (7) with fusions of the POI fusion etc., depending on the experimental design. bioPepID are biopeptide libraries of the PepID type (EP09000893.9). These can be used in the tANCHOR system. AbsI-SgrDI and AscI-MauBI as well as AsiSI-PacI are interlocked restriction endonucleases, compatible with each other, with eight-mer recognition sequence for the multiplexing of the expression of multiple genes. Any other realisation of the applications according to the invention is equally covered by the patent document.

FIG. 2C: Examples of various linker variants according to the invention in combination with CD63ΔLEL in the exemplary vector pAE211_CMV-P-CD63ΔLEL. The restriction sites EcoRI, EcoRV, HindIII, BamHI and PstI are possible for the insertion of multiple consecutive epitope units according to a standard cloning method or cloning method for seamless cloning. (1) Seq1, only the restriction sites according to the invention and tested with regard to function (R sites) EcoRI and EcoRV and n*N=spacer sequence (2) Seq(1) plus His6-Tag, (3) Seq(1) plus CMyc Epitope, (4) Seq(1) plus His6-Tag plus C-Myc (5) TEV proteolysis sites, including the central cloning sites, in order to harvest the expressed foreign protein selectively. (6) all translated and non-translated molecular functional elements named in (8) combined in a construct (SEQ ID NOs: 39, 40). (9) Minimal linker zur for transport to the cell surface (SEQ ID NOs: 41,42).

Figure 3A:
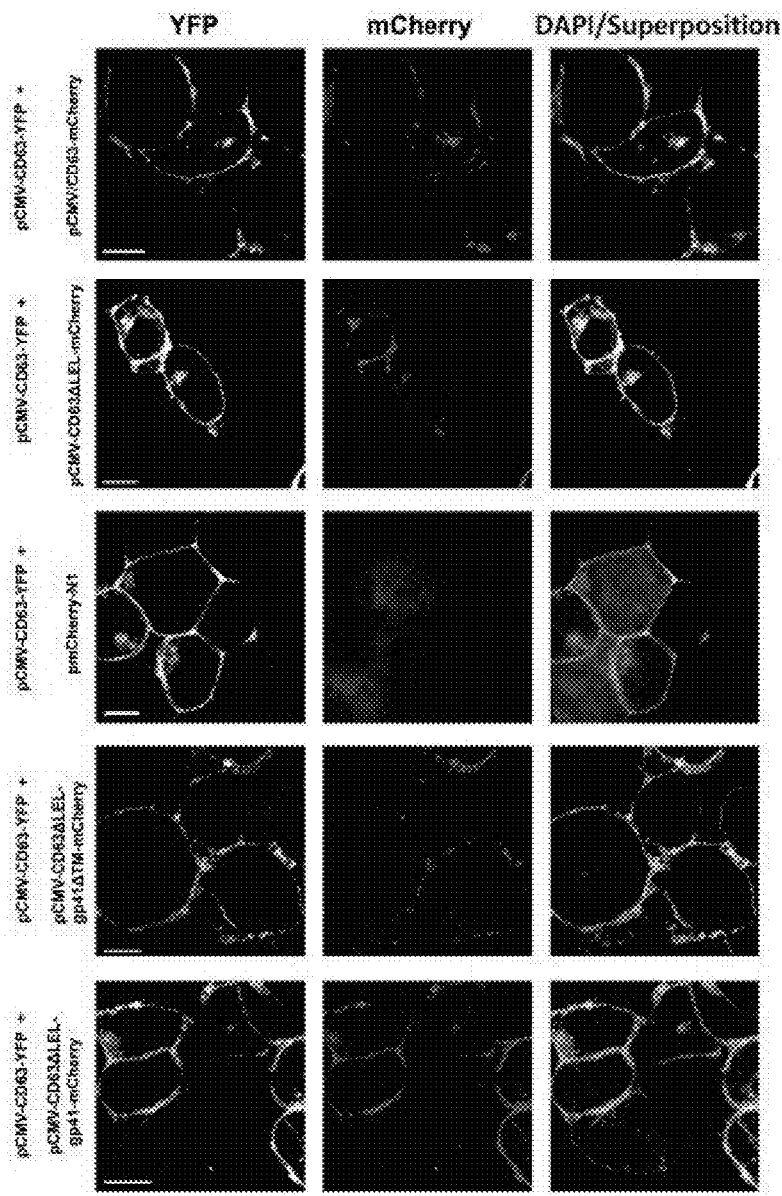
Figure 3B:
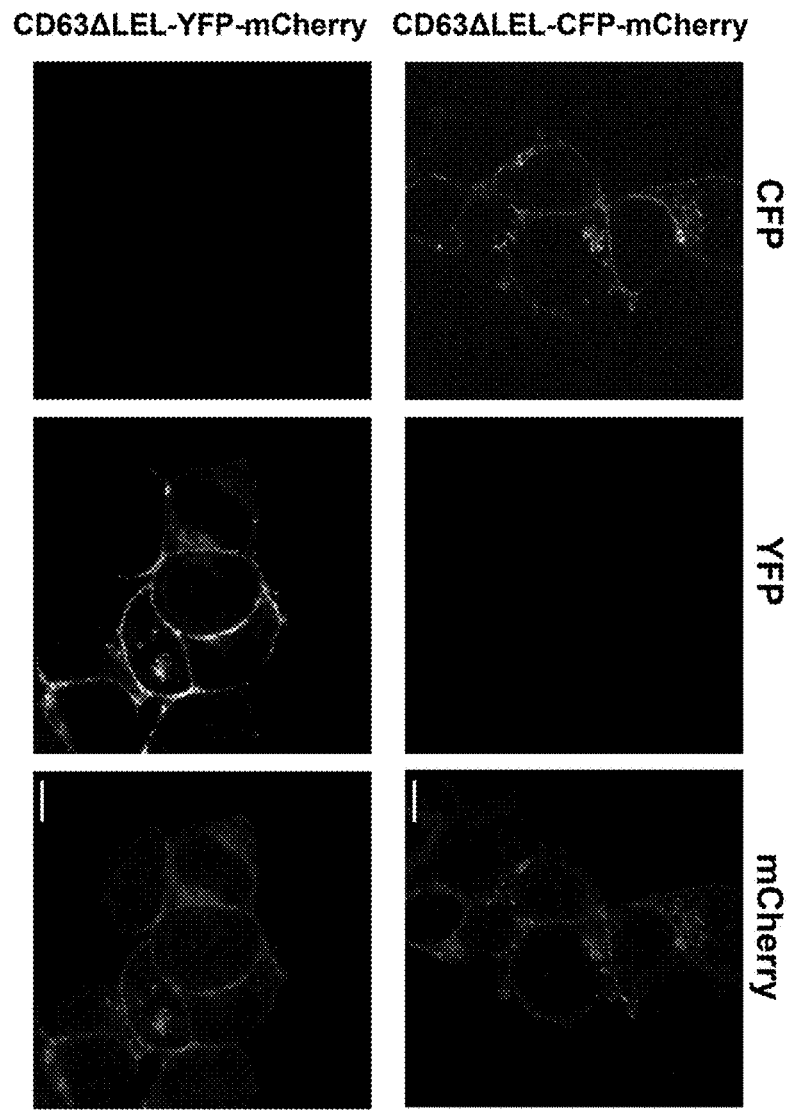
Figure 3C:
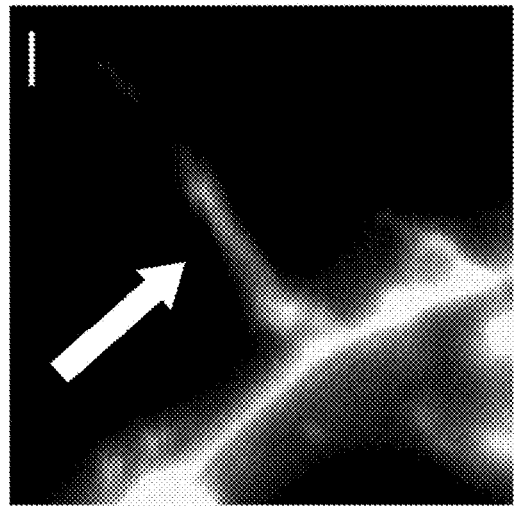
Figure 3C:
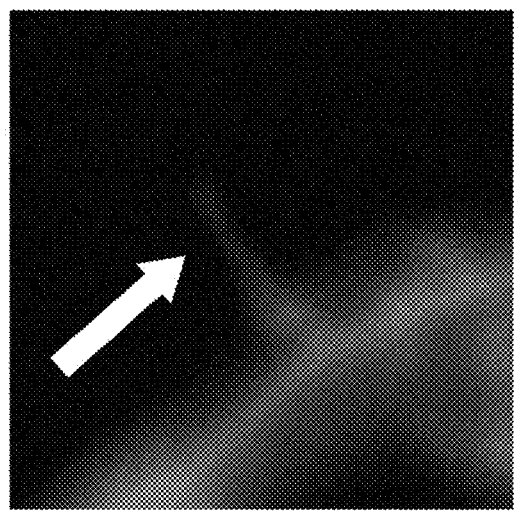

FIGS. 3A-3C: Localisation of fusion proteins on the surface of HEK293T cells by means of cLSM.

Figure 1A:
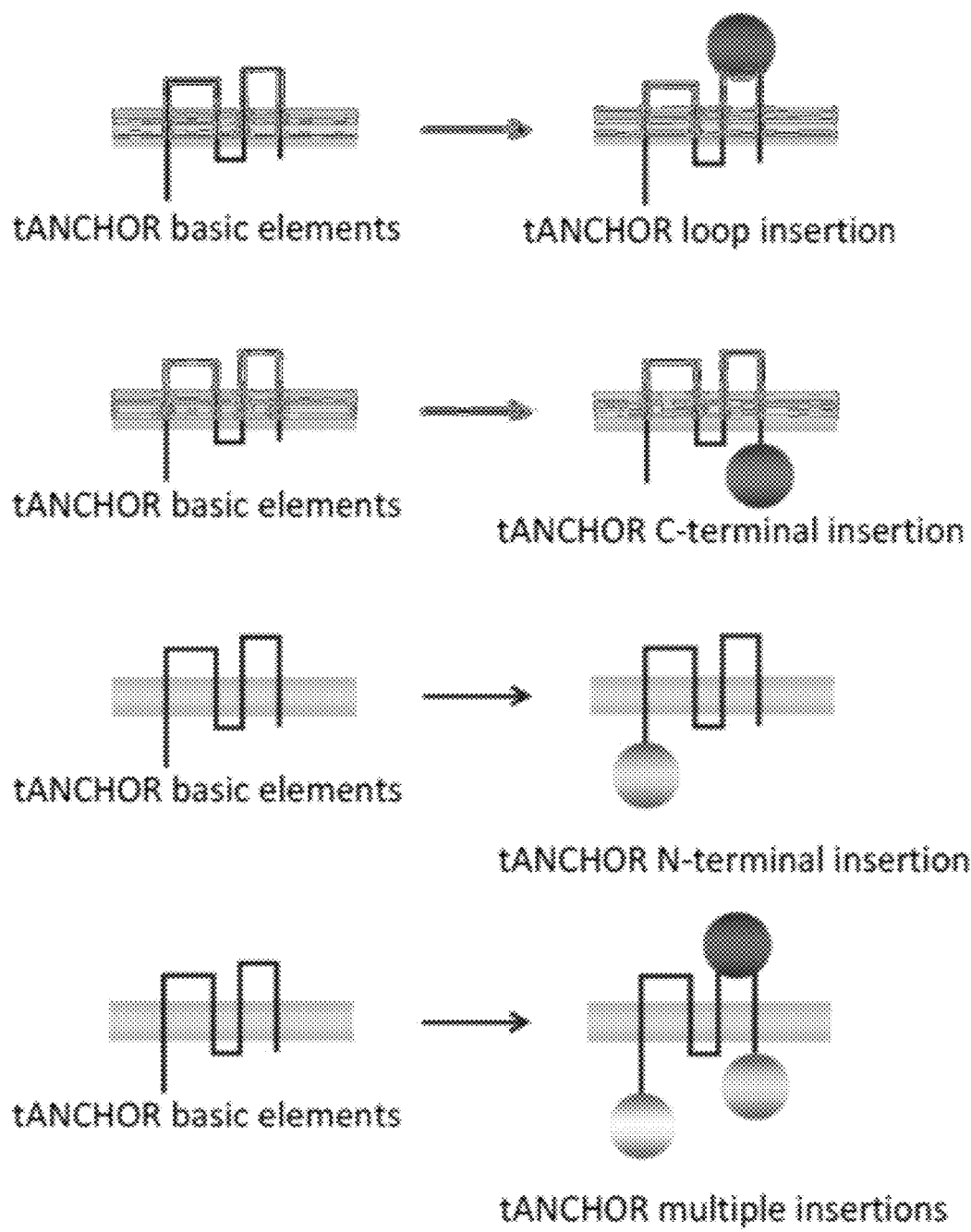
FIGS. 1A and 1B: Schematic representation of the fusions according to the invention and localisation of the fusion proteins.
Figure 1B:
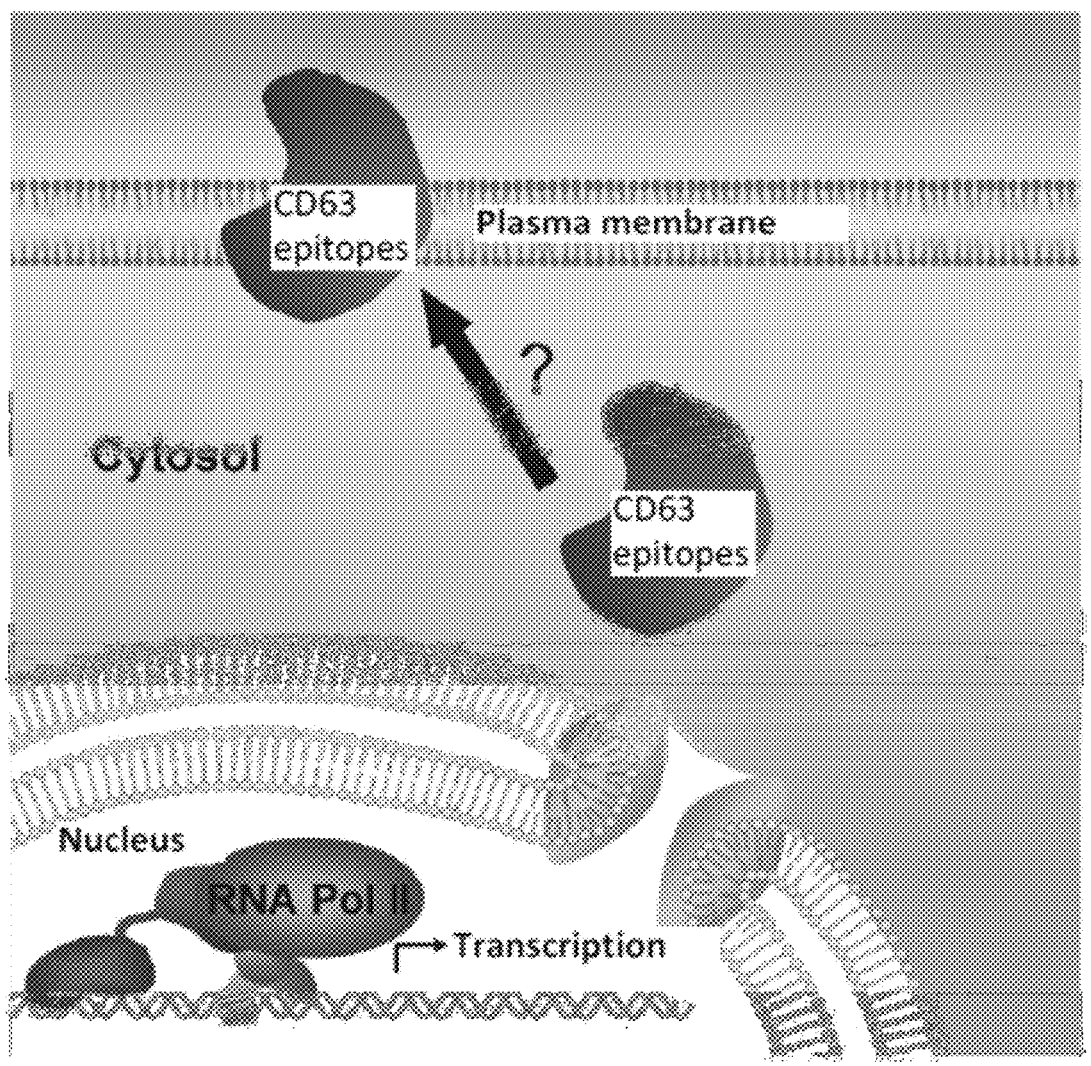

(A) HEK293T cells were cotransferred with the respective vectors. In the localisation studies the vector pCMV-CD63-YFP served as control for the expressed wild-type CD63-YFP protein. For all proteins containing the tANCHOR technology (CD63ΔLEL, FIG. 2B), a predominant localisation on the cell surface was detected by the fused reporter protein mCherry. The mCherry protein without tANCHOR fusion is cytoplasmic, evenly distributed. It shows no predominance on the cell surface. Additionally further proteins such as e.g. the glycoprotein gp41 of HIV-1 with and without transmembrane domain (gp41ΔTM) can be presented on the surface. (B) The protein folding was checked by means of CFP and YFP localisation on the surface. Both fluorescent proteins can be detected after exciting by the diode/argon laser at 405 nm (CFP) or 514 nm (YFP), a specific emission wavelength for the fluorophore. (C) The expressed protein mCherry, which normally occurs distributed in the cytosol, is directed into the plasma membrane with high efficiency by the tANCHOR system. In this way the mCherry with implemented tANCHOR technology is detectable even in the filopodia (white arrow) of the HEK293T cells, as in the case of the wild-type CD63-YFP. Length of the scale bars is 10 μm in FIGS. 3A, 3B and 1 μm in FIG. 3C.

Figure 4:
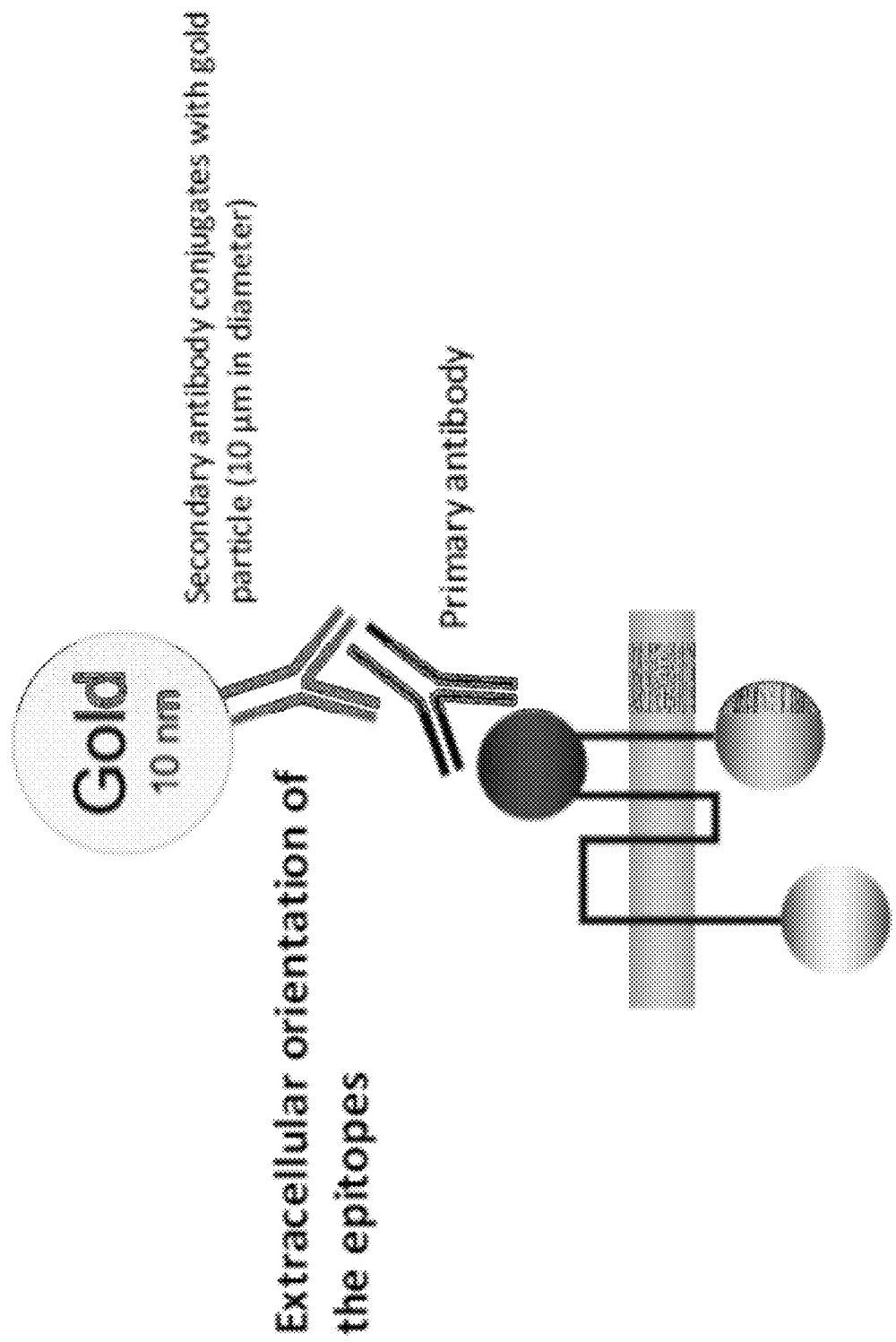
Figure 5A:
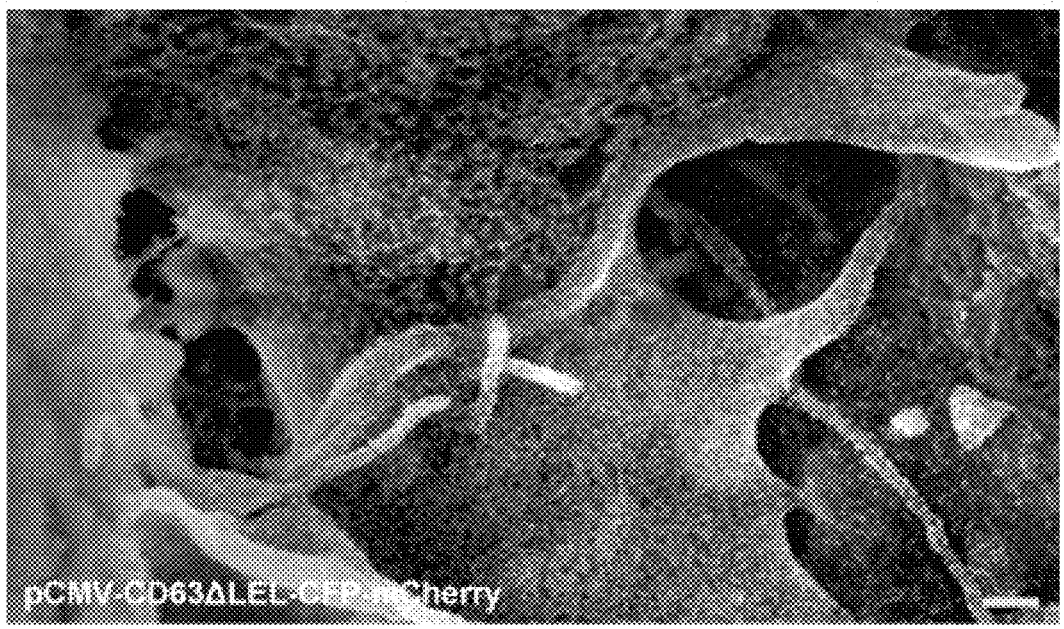
Figure 5A:
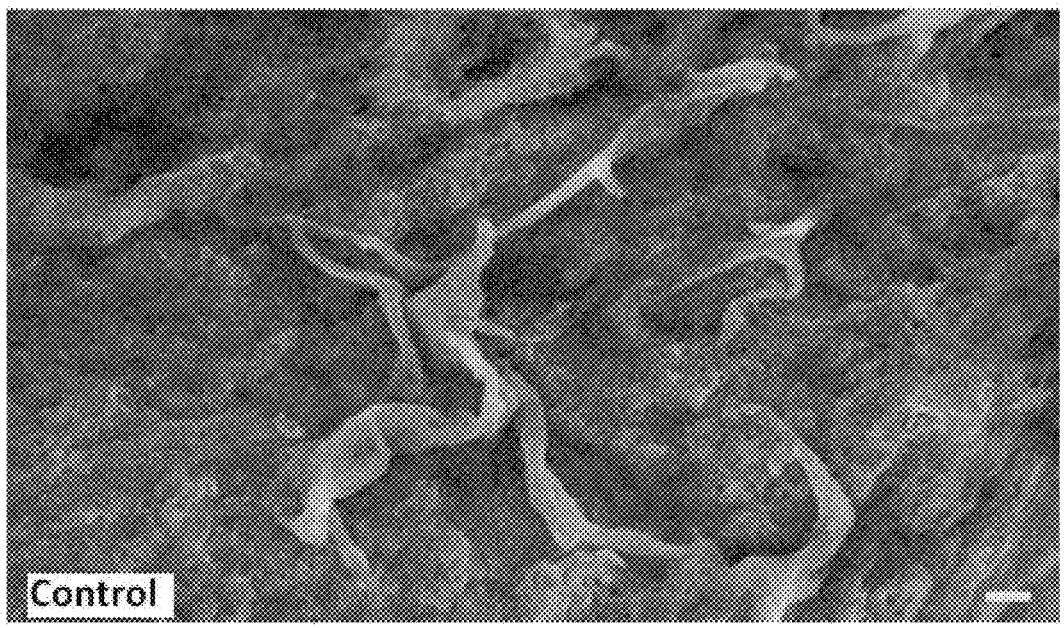
Figure 5B:
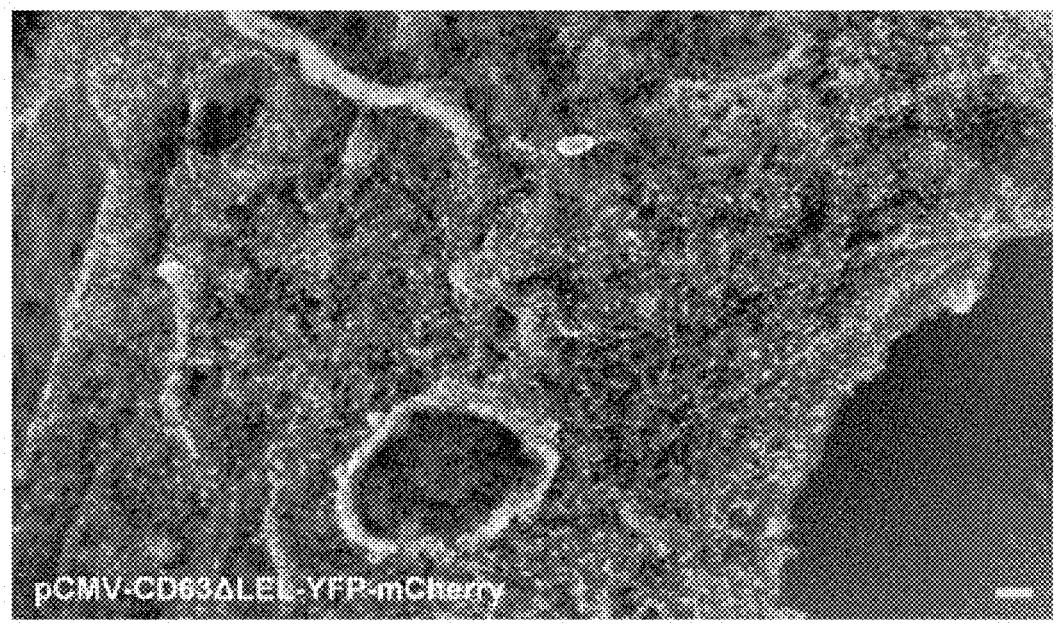
Figure 5B:
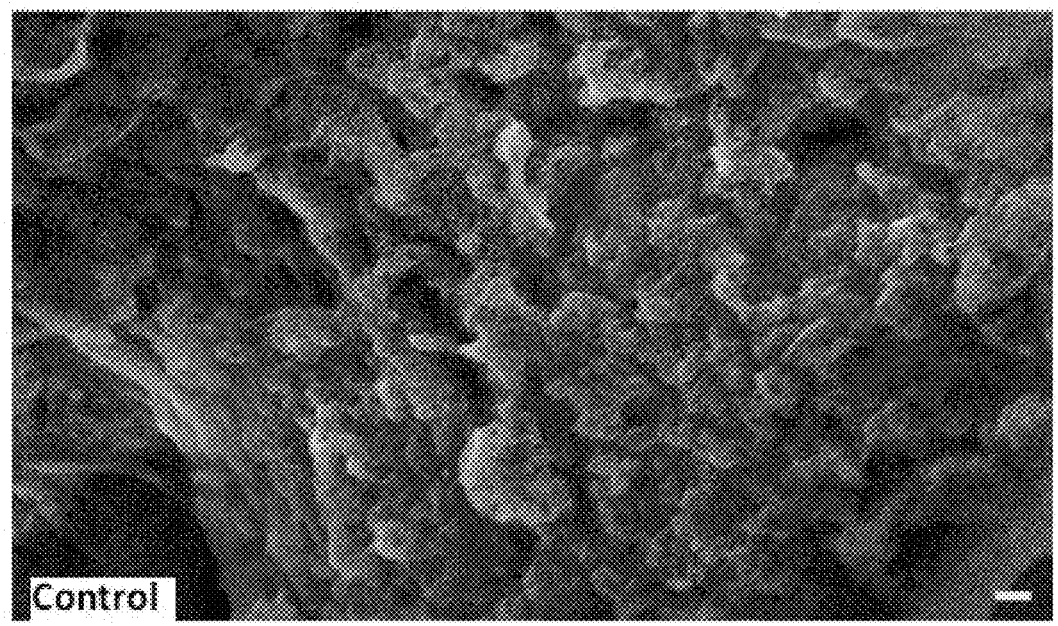
Figure 5C:
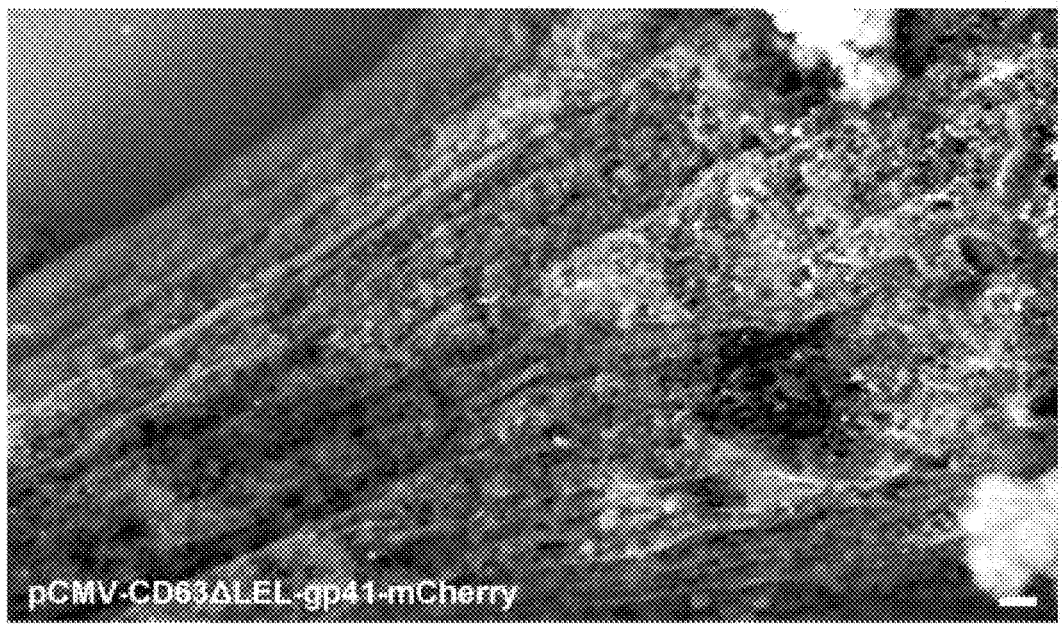
Figure 5C:
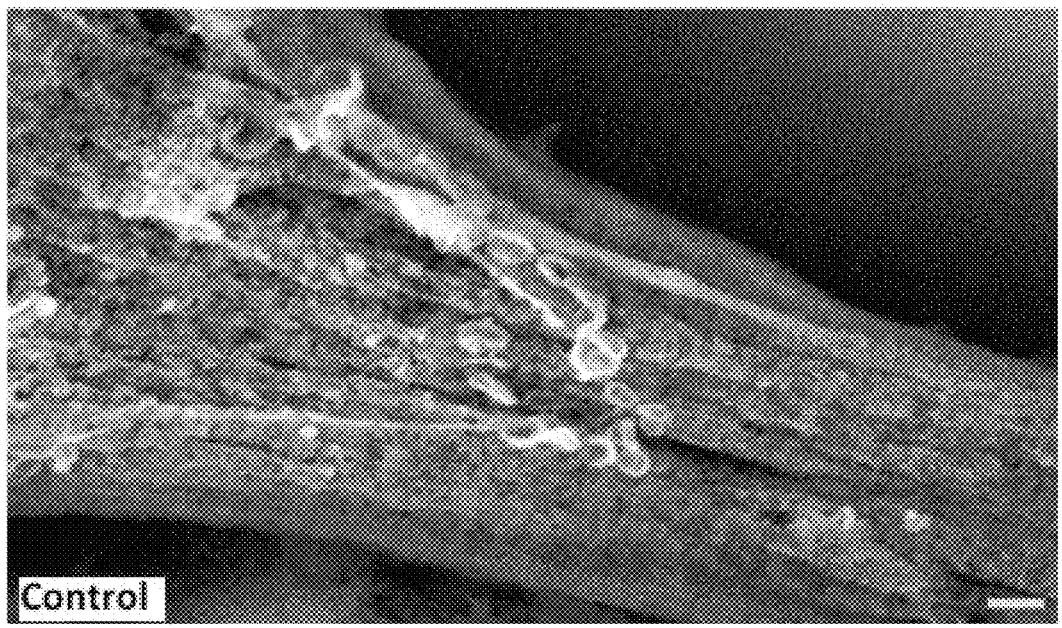
Figure 5D:
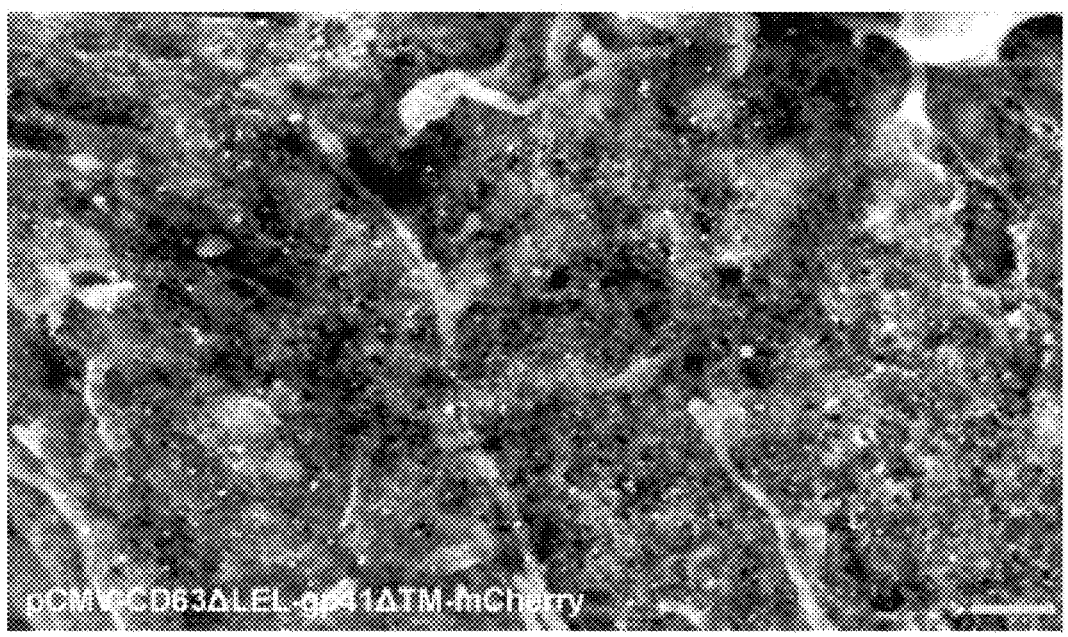
Figure 5D:
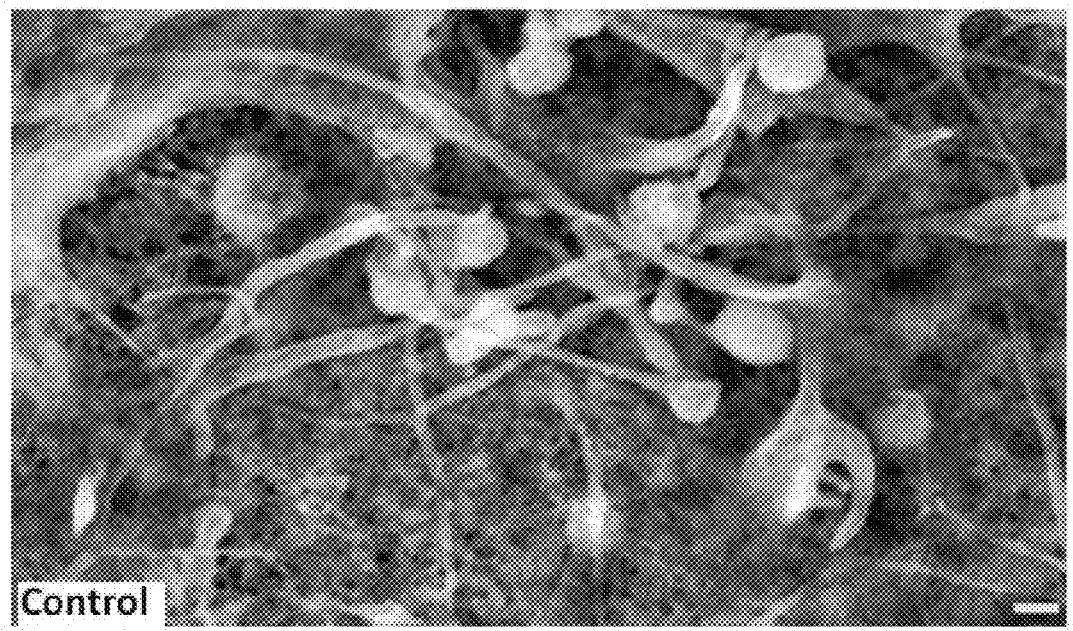

FIG. 4: Schematic representation of extracellular orientation examination of the epitopes The detection of the epitope orientation was carried out by means of scanning electron microscopy (SEM) on the surface of transfected HEK293T. The proteins were bound by means of primary antibodies and visualised by means of conjugated secondary antibodies with gold particles (10 nm). In the case of the model epitopes YFP, CFP, gp41 and gp41ΔTM bound antibodies could be visualised on the surface by means of immunogold particles (FIG. 5).

FIG. 5A-5D: SEM image of gold particles (10 nm) on the surface of HEK293T cells.

The transfected HEK293T cells were examined respectively with regard to epitope orientation. For this the respective epitopes were bound with specific primary antibodies and these were then detected with gold-conjugated secondary antibodies. For all epitopes with the tANCHOR technology it was possible to ascribe an extracellular orientation to the epitopes. Length of the scale bars in all figures is 300 nm.

Figure 6:
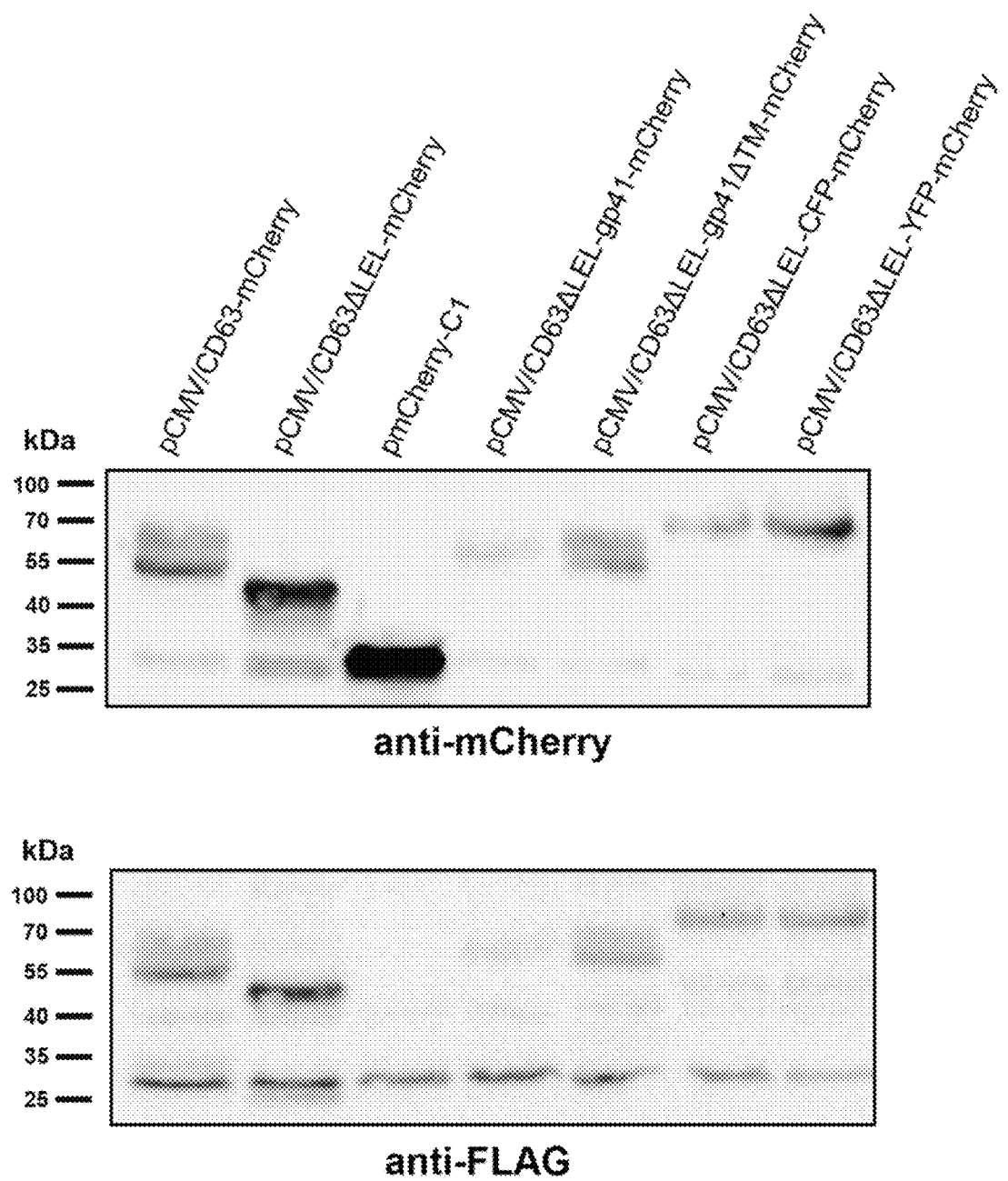

FIG. 6: Western blot analysis of transfected HEK293T cells with generated tANCHOR vectors.

The transfected HEK293T cells were subjected to a Western blot analysis. The expressed proteins in the separated cell lysates were aligned by means of primary antibodies against the C-terminal reporter protein mCherry and detected against the N-terminal epitope FLAG. The transfection with the vector pmCherry-N1 shows no band in respect of the incubation with anti-FLAG antibody, as this vector contains no sequence for the FLAG epitope and serves as a control for the specific detection of the expressed proteins.

Figure 7:
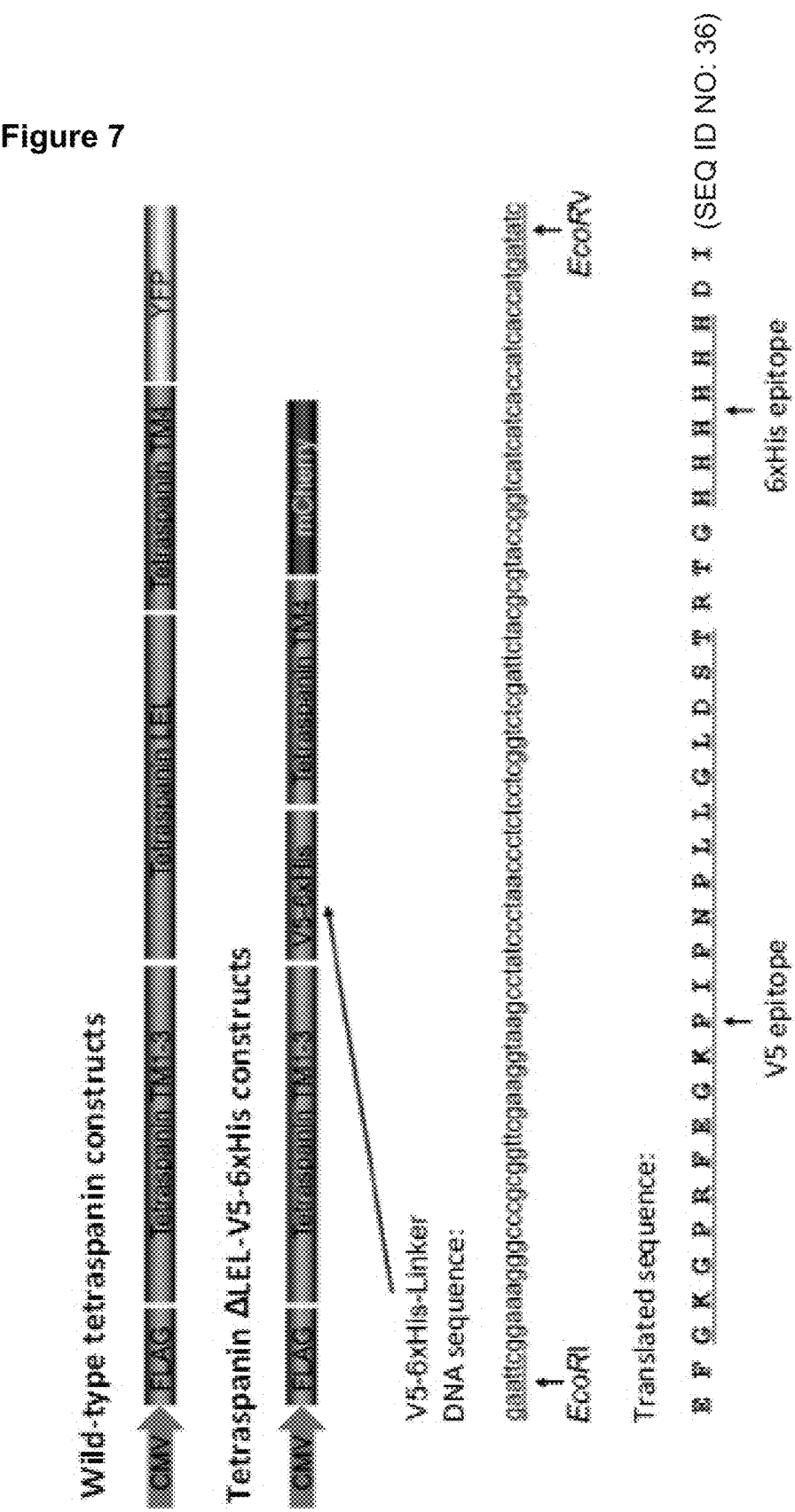

FIG. 7: Schematic representation of the constructs for examining further tetraspanins with regard to protein transport with internal fusion site with V5-6×His linker.

To examine the validity of the protein transport independently of the large extracellular loop within the tetraspanin super-family, expression vectors were generated, containing an internal fusion V5-6×His between the 3rd and 4th transmembrane domain according to the tANCHOR prototype constructs based on CD63ΔLEL. The internal fusion V56× His contains the linker between EcoRI and EcoRV (SEQ ID NOs: 35, 36). A FLAG fusion is integrated N-terminally; C-terminally the fluorescent proteins YFP are fused in the case of wild-type tetraspanin constructs and mCherry is fused in the case of ΔLEL-V5-6×His constructs as reporter proteins.

FIGS. 8A-8D: Localisation of fusion proteins on the surface of HEK293T cells.

HEK293T cells were cotransfected with the generated vectors (A) pCMV-CD9-YFP/pCMV-CD9ΔLEL-V5-6× His-mCherry, (B) pCMV-CD81-YFP/pCMV-CD81ΔLEL-V5-6×His-mCherry, (C) pCMV-CD82-YFP/pCMV-CD82ΔLEL-V5-6×His-mCherry and (D) pCMV-CD151-YFP/pCMV-CD151ΔLEL-V5-6×His-mCherry. All expressed proteins can be detected dominantly by means of fluorescence of the reporter protein mCherry on the cell surface. The construct containing the internal fusion with the linker V5-6×His between the 3rd and 4th transmembrane domain (FIG. 7) of the tetraspanins CD9, CD81, CD82 and CD151 colocalise with the corresponding expressed wild-type tetraspanins with the fusion of the fluorescent protein YFP. Length of the scale bars in all figures is 10 μm.

FIGS. 9A-9E: Application of the tANCHOR system to detect antibodies (A) Results of the ELISA experiments[53] by means of tANCHOR system in the 96-well format. The V5 epitope on the cell surface of HEK293T cells was detected with HRP-conjugated anti-V5 antibodies. The protein expression of the tANCHOR proteins can be detected concentration-dependently and significantly by anti-V5-HRP antibodies. (B) Schematic representation of the linkers 2F5-4E10 between the 3rd and 4th transmembrane domain of CD63 (SEQ ID NOs: 37, 38). The linkers were introduced into the vector pCMV-CD63ΔLEL. (C) The HIV-1 neutralising antibodies anti-2F5 and anti-4E10 were bound to the 2F5 and 4E10 epitope with a constant DNA quantity of 0.6 μg per well of transfected HeLa cell primer. The bound anti-2F5 and anti-4E10 antibodies could be detected significantly, (E) expressed fusion proteins CD63ΔLEL-V5-6×His and also CD63ΔLEL-2F5-4E10 could be localised dominantly on the surface of HEK293T cells for control. The length of the scale bars in all figures is 10 μm.

FIGS. 10A-B: Increase in efficiency through the use of low-serine and low-arginine linkers.

(A) The linkers used are represented at DNA and amino-acid sequence level. The analysis of the subcellular localisation of the fusion proteins with two different linkers (SEQ ID NOs: 41, 42 and SEQ ID NOs: 43, 44) shows clearly, that the use of EcoRI/EcoRV flanking restriction sites leads to a high efficiency of the protein transport to the surface of the HEK293T cells and the fusion protein is detectable on the filopodia (white arrow) that have formed on the cells (B). The length of the scale bars in all figures is 10 μm.

1. GENERATION OF CD63-BASED MODEL VECTORS FOR THE CARRYING-OUT OF LOCALISATION EXPERIMENTS

The generation of CD63-based model vectors was based on the use of the vector pCMV-Tag2B (Stratagene). By means of established cloning techniques the respective DNA sequences were brought into this vector by way of restriction sites[39]. The control vector pCMV-CD63-YFP, described also as pCMV-CD63-YFP-FLAG[49], which contains the full-length sequence of CD63 (amino-acids 1-238, GenBank accession no. KF998086), was used to introduce the DNA sequence of the red fluorescent reporter protein used, mCherry, by means of the primers PA1-01/PA1-02 and the template vector pmCherry-N1 (Clonteeh) by way of the restriction sites XhoI and ApaI. The partial sequence with the transmembrane domains TM1-3 (amino-acids 1-110 GenBank accession no. KF998086) was brought in by way of the restriction sites BamHI and PstI with the help of the primers PA1-03/PA1-04 and thereafter the TM4 (amino-acids 201-238, GenBank accession no. KF998086) was brought into the vector pCMV-Tag2B by way of EcoRV and HindIII with the help of the primers PA1-05/PA1-06 and also the template vector pPR3-N-CD63[49]. The resulting vector contains the CD63 gene sequence without LEL (pCMV-CD63ΔLEL) (FIG. 2B).

For simplified detection of the proteins the restricted mCherry DNA fragment of the vector pCMV-CD63-mCherry was ligated into the restricted vector pCMV-CD63ΔLEL by way of the restriction sites XhoI and ApaI. The vectors pCMV-CD63ΔLEL-CFP and pCMV-CD63ΔLEL-YFP were generated by way of the restriction sites EcoRI and EcoRV with the help of the primers PA1-07/PA1-08 and also the template vector pSCFP3A-C1 or pSYFP2-C1[50]. In the same way the vectors pCMV-gp41ΔTM and pCMV-gp41 were generated with the help of the primers PA1-09/PA1-010 and PA1-09/PA1-11 and of the template vector pNL4-3[51], which contains the gene sequence of the gp41 protein of HIV-1.

2. TRANSFECTION AND CONFOCAL LASER SCANNING MICROSCOPY (CLSM)

To examine the localisation of expressed fusion proteins, the plasmids generated in example 1 were transfected in HEK293T cells by means of transfection reagent. For this HEK293T (human embryonic kidney cells 293T) cells were seeded out in ibiTreat 8-wells and cultivated in Dulbecco's modified Eagle's Medium, complemented with 10% foetal calf serum, L-glutamine and penicillin/streptomycin. At approx. 50% confluence the cells were transfected by means of Metafectene® PRO (Biontex) with the generated plasmids in accordance with the manufacturer's instructions. After 24 h the transfected cells were fixed in 2% paraformaldehyde in PBS, washed twice in PBS and mounted in 90% glycerol in PBS with 0.1% p-phenylenediamine and DAPI (4',6-diamidino-2-phenylindole) to visualise the nucleus. The transfected cells were examined with an inverse, confocal laser microscope LSM 780 (Carl Zeiss) with regard to subcellular localisation (FIG. 3A-3C). The settings of the excitation and emission wavelengths were selected for the fluorescent proteins CFP, YFP and mCherry by means of the Smart Setup option of the LSM 780 software ZEN 2010.

3. ORIENTATION ANALYSIS OF THE EPITOPES ON THE SURFACE OF HEK293T CELLS BY MEANS OF SCANNING ELECTRON MICROSCOPY

The expressed proteins were detected by means of scanning electron microscopy of proteins immune-marked with gold on the plasma membrane of HEK293T cells (FIG. 4). For this the cells, transfected and fixed in 2% paraformaldehyde in PBS, were washed three times in PBS and blocked with 0.5% BSA/0.1% gelatin in PBS. The proteins CD63ΔLEL-CFP and CD63ΔLEL-YFP were incubated with rabbit anti-GFP (ab6556, Abcam), washed and the primary antibodies with goat anti-rabbit were detected with conjugated 10 nm gold particles. The immune marking was followed by postfixation with glutaraldehyde (2.5% in HEPES 0.05M). This was followed by preparation for scanning. For this the samples were desiccated step by step in ethanol stages (30%, 50%, 70%, 90%, 96%), for 15 min in each case, and left for 30 min in absolute ethanol, transferred into HMDS (hexamethyldisilazane), dried out of HMDS and the sample surface was coated with evaporated carbon. The gold particles were visualised with the Leo 1530 Gemini scanning electron microscope by means of backscatter detector (Centaurus). In the same way the gp41 protein was detected by means of human anti-2F5 antibody (National Institutes of Health, NIH) and also with the use of the antibody goat anti-human with conjugated IgG H&L 10 nm gold particles (BBInternational) (FIG. 5A-5D).

4. WESTERN BLOT ANALYSIS OF EXPRESSED FLUORESCENT PROTEINS

To examine the protein expression, cell lysates of transfected HEK293T cells were subjected to a Western blot analysis. For this HEK293T cells with the vectors were transfected in the 6-well format with METAFECTENE® PRO in accordance with the manufacturer's instructions. After 48 h the medium was removed completely and 100 µl Laemmli sample buffer 2× and 25 U of an endonuclease from Serratia marcescens (Benzonase®) were put into each 6-well. The cells were lysed and after about 10 min 5 µl β-mercaptoethanol were added to the samples and denatured at 95° C. for 5 min. These cell lysates were separated by means of SDS-PAGE, transferred to a PVDF membrane and detected with mouse anti-mCherry (ab125096, Abcam) or goat anti-FLAG (NB600-344, NovusBio) antibodies and also HRP-conjugated anti-mouse/anti-goat antibodies (Dako) and the bound HRP-conjugated antibodies were detected by means of Pierce ECL Western blot substrate (Thermo Fisher Scientific). The PVDF membrane was treated with Roti®-Free Stripping Buffer 2.2 plus (Carl Roth), so the same proteins could be detected with a further primary antibody (FIG. 6).

5. EXAMINATION OF THE SUBCELLULAR LOCALISATION OF TETRASPANIN-BASED HYBRID PROTEINS FROM THE TETRASPANIN SUPER-FAMILY

Figure 8:
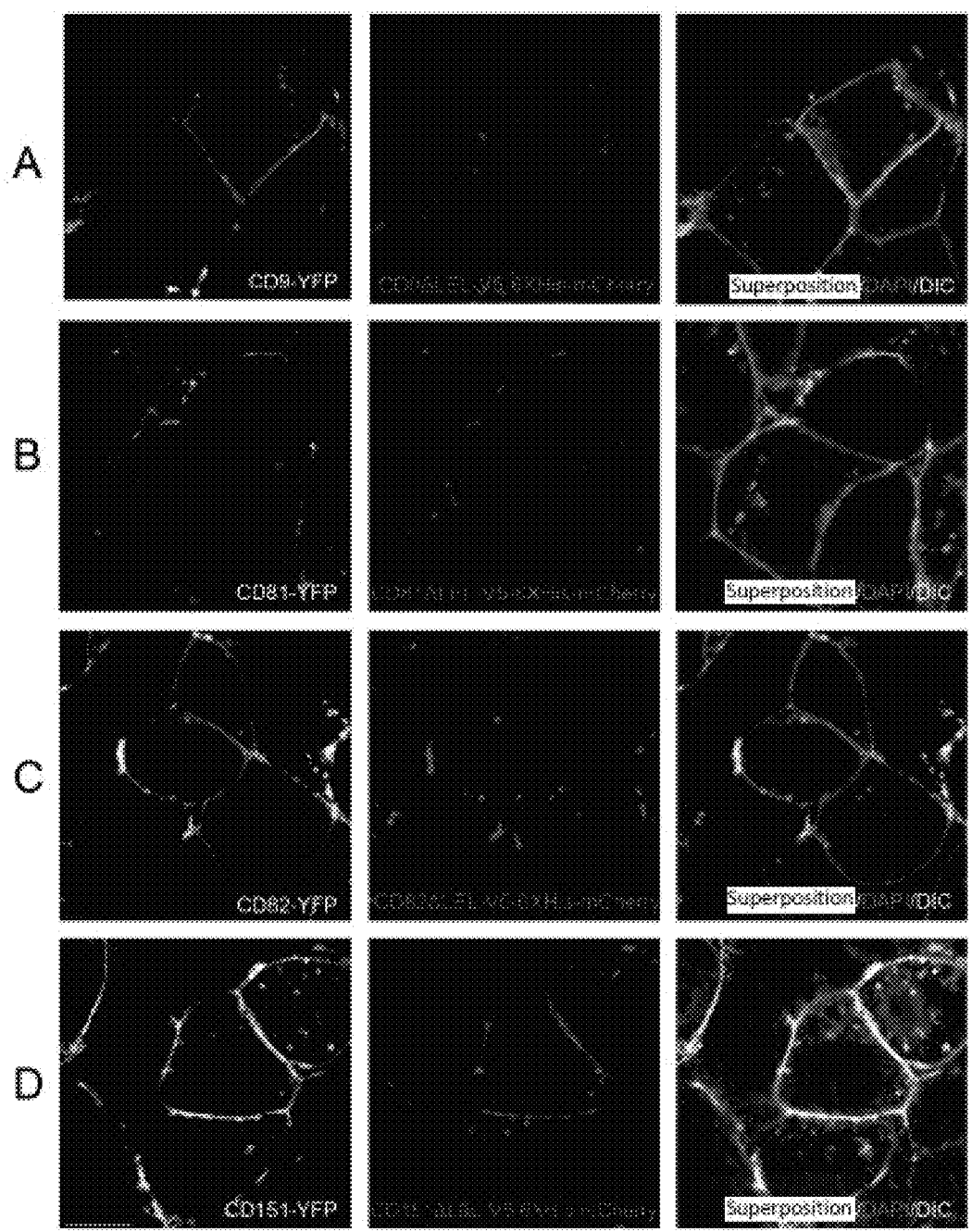

To examine the peptide presentation on the cell surface within the tetraspanin super-family, expression vectors were generated in accordance with the schematic representation (FIG. 7) by means of gene synthese[54] (ATG:Biosynthetics) and also standardised cloning methods. The gene sequences of CD9 (SEQ ID NO: 19), CD81 (SEQ ID NO: 21), CD82 (SEQ ID NO: 23) and CD151 (SEQ ID NO: 25) were replaced in the vector pCMV-CD63-YFP and the gene sequences for CD9ΔLEL-V5-6×His (SEQ ID NO: 27), CD81ΔLEL-V5-6×His (SEQ ID NO: 29), CD82ΔLEL-V5-6×His (SEQ ID NO: 31) and CD151ΔLEL-V5-6×His (SEQ ID NO: 33) were replaced in the vector pCMV-CD63-mCherry (see 1: Generation of CD63-based model vectors for the carrying out of localisation experiments) with the tetraspanin sequence of CD63 by way of the restriction sites NotI/XhoI and the following expression vectors of wild-type gene sequence pCMV-CD9-YFP, pCMV-CD81-YFP, pCMV-CD82-YFP, pCMV-CD151-YFP and also deletion mutants of the large extracellular loop (ΔLEL) were transfected with the internal linker V5-6×His-pCMV-CD9ΔLEL-V5-6×His-mCherry, pCMV-CD81ΔLEL-V5-6×His-mCherry, pCMV-CD82ΔLEL-V5-6×His-mCherry and pCMV-CD151ΔLEL-V5-6×HismCherry, as described in section 2 Transfection and confocal laser scanning microscopy (cLSM), and examined by means of cLSM with regard to subcellular localisation (FIG. 8).

6. APPLICATION OF THE TANCHOR SYSTEM TO THE DETECTION OF ANTIBODIES BY MEANS OF ELISA METHOD[53]

The highly efficient surface expression of fusion proteins by means of tANCHOR system is suitable for the detection of bound antibodies on presented peptides. As model the linker V5-6×His was isolated from the construct pCMV-CD9ΔLEL-V5-6×His-mCherry by way of EcoRI and EcoRV and inserted into the vector pCMV-CD63ΔLEL-mCherry by way of standard cloning methods, as described in section 1 Generation of CD63-based model vectors for the carrying-out of localisation experiments. Likewise the epitopes 2F5 and 4E10 (HIV-1) were inserted into the vector pCMV-CD63ΔLEL-mCherry by means of the primers PA1-12/PA1-13 and the template vector pNL4-3 (FIG. 9B). To detect bound antibodies on the surface of (FIG. 9A) HEK293T, HEK293T cells and (FIG. 9C) HeLa cells were seeded out in the 96-well format and transfected with the plasmids pCMV-CD63ΔLEL-V5-6×His-mCherry (FIG. 9A) and pCMV-CD63ΔLEL-2F5-4E10-mCherry (FIG. 9C) by means of Metafectene® PRO in accordance with the manufacturer's instructions. After 24 h the cells were fixed for 20 min with 4% paraformaldehyde (Carl Roth), washed twice with PBS and blocked overnight with a solution of 3% bovine serum albumin grade V (Carl Roth) and 2% chicken egg albumin (Carl Roth). Thereafter the cells were washed once with PBS and incubated for 1 h with dilute antibody (FIG. 9A) anti-V5-HRP (Invitrogen) and (FIG. 9C) human anti-2F5/human anti-4E10 (NIH) in a dilution of 1:3000. In the case of FIG. 9C the primary antibodies were bound by means of hare anti-human HRP (DAKO) in a dilution of 1:1000 and both ELISA variants with 3,3',5,5'-tetramethylbenzidine as ELISA substrate (TMB Substrate Kit, Thermo Fisher Scientific) were used in accordance with the manufacturer's instructions and the OD values were measured at 450 nm with the MultiscanTMGO spectrophotometer with 96-well plate insert (Thermo Fisher Scientific). The expression of the fusion proteins was detected by means of cLSM, as in section 1 Generation of CD63-based model vectors for the carrying-out of localisation experiments.

7. INCREASE IN EFFICIENCY OF THE PROTEIN TRANSPORT TO THE SURFACE OF HUMAN CELLS THROUGH THE USE OF FLANKING ECORI/ECORV RESTRICTION SITES IN THE TANCHOR SYSTEM

The use of flanking EcoRI/EcoRV restriction sites in the tANCHOR system increases the transport efficiency to the cell surface. The bringing-in of further restriction sites into the minimal linker (L Q E F D I G G G G, SEQ ID NO:42) leads to the translation of serine and arginine in the linker (G S S G R R S L Q G G G G, SEQ ID NO:44) between the 3rd and 4th transmembrane domain of CD63 (FIG. 10A). The vectors with further sites were generated through gene synthesis.sup.54 (ATG:Biosynthetics) and brought to expression in HEK293T cells, as described already in section 2 Transfection and confocal laser scanning microscopy (cLSM), and examined with regard to subcellular localisation (FIG. 10B).

SEQUENCE RECORD

SEQ ID NO: 1: DNA sequence of pA4E211 (CD63ΔLEL)
SEQ ID NO: 2: DNA sequence of CD63ΔLEL
SEQ ID NO: 3: Protein sequence of CD63ΔLEL
SEQ ID NO: 4: Primer PA1-01
SEQ ID NO: 5: Primer PA-02
SEQ ID NO: 6: Primer PA1-03
SEQ ID NO: 7: Primer PA1-04
SEQ ID NO: 8: Primer PA1-05
SEQ ID NO: 9: Primer PA1-06
SEQ ID NO: 10: Primer PA1-07
SEQ ID NO: 11: Primer PA1-08
SEQ ID NO: 12: Primer PA1-09
SEQ ID NO: 13: Primer PA1-10
SEQ ID NO: 14: Primer PA1-11
SEQ ID NO: 15: Primer PA1-12
SEQ ID NO: 16: Primer PA1-13
SEQ ID NO: 17: CD63, GenBank accession No. KF998086
SEQ IN NO: 18: Protein sequence of CD63
SEQ ID NO: 19: DNA sequence of CD9 (GenBank accession No. NM_001769.3)
SEQ ID NO: 20: Protein sequence of CD9
SEQ ID NO: 21: DNA sequence of CD81 (GenBank accession No. NM_004356.3)
SEQ ID NO: 22: Protein sequence of CD81
SEQ ID NO: 23: DNA sequence of CD82 (GenBank accession No. NM_002231.3)
SEQ ID NO: 24: Protein sequence of CD82
SEQ ID NO: 25: DNA sequence of CD151 (GenBank accession No. BT007397.1)
SEQ ID NO: 26: Protein sequence of CD151
SEQ ID NO: 27: DNA sequence of CD9ΔLEL-V5-6xHis
SEQ ID NO: 28: Protein sequence of CD9ΔLEL-V5-6×His
SEQ ID NO: 29: DNA sequence of CD81ΔLEL-V5-6×His
SEQ ID NO: 30: Protein sequence of CD81ΔLEL-V5-6×His
SEQ ID NO: 31: DNA sequence of CD82ΔLEL-V5-6×His
SEQ ID NO: 32: Protein sequence of CD82ΔLEL-V5-6×His
SEQ ID NO: 33: DNA sequence of CD151ΔLEL-V5-6×His
SEQ ID NO: 34: Protein sequence of CD151ΔLEL-V5-6×His
SEQ ID NO: 35: DNA sequence of the V5-6×His linker
SEQ ID NO: 36: Protein sequence of the V5-6×His linker
SEQ ID NO: 37: DNA sequence of the 2F5-4E10 linker
SEQ ID NO: 38: Protein sequence of the 2F5-4E10 linker
SEQ ID NO: 39: DNA sequence of the linker version (8)
SEQ ID NO: 40: Protein sequence of the linker version (8)
SEQ ID NO: 41: DNA sequence of the linker in the vector pCMV-CD63ΔLEL-mCherry (minimal linker (9))
SEQ ID NO: 42: Protein sequence of the linker in the vector pCMV-CD63ΔLEL-mCherry (minimal linker (9))
SEQ ID NO: 43: DNA sequence of the linker in the vector pCMV-CD63ΔLEL-V2-mCherry
SEQ ID NO: 44: Protein sequence of the linker in the vector pCMV-CD63ΔLEL-V2-mCherry
SEQ ID NO: 45: DNA sequence of the linker between CD63ΔLEL and the fluorescent protein
SEQ ID NO: 46: Protein sequence of the linker between CD63ΔLEL and the fluorescent protein Summarised below are preferred aspects of the invention:

1. Method for the use of proteins/peptides with intended artificial amino-acid sequences, which are coded indirectly, at least partially from template molecules, or are completely synthetic, which
   a. can consist at least partially of the sequences of members of the protein classes of the tetraspanins, such as for example the human genes CD63, CD9, CD82, CD81, CD151, CD53
   b. but also at least partially of sequence-homologous tetraspanins of other organisms and
   c. according to a. and b., the fusion products of which generate molecules that are able to direct the natural or artificial peptide and protein units connected with them in suitable systems
      i. to one or more surfaces,
      ii. to transport these over the surfaces, and
      iii. to anchor these firmly in the surfaces
      iv. to present these enduringly on the surfaces
2. Chimeric protein molecules with natural and/or artificial amino-acid composition according to 1., which serve indirectly to generate protein units that
   a. are modified, e.g. glycosylated, on surfaces or/and
   b. can adopt a functional conformation on surfaces.
3. Molecules according to 1. and 2. that are generated indirectly by way of coding templates and that emerge from the fusion of at least partial units of at least one of the coding templates and that, from a combination of various sequences, can be generated and possibly enriched and isolated, and possibly also processed in the meantime
   a. in vivo
   b. in vitro.
4. Molecules according to 1., 2. and 3. that represent coding nucleic acid molecules that express these in vivo and in vitro according to the invention
   i. in vivo recombinantly, intra-genomically, (TN7 system) or
   ii. in vivo by means of extra-chromosomal genetic elements (vectors) or
   iii. in vivo by means of natural or non-naturally-occurring nucleic acid molecules (RNA etc.) by means of circular or linear nucleic acid molecules or
   iv. in vitro in coupled transcription or translation systems
   v. in vivo with the incorporation of artificial amino-acids.
5. Surfaces for the anchoring of molecules according to 1. to 3. that represent naturally-occurring cell membranes of natural cells or artificial membrane systems.
6. Molecules according to 1. to 4. that serve their gene products, transfected cells or parts of cells, to resolve structural, bioanalytical and (veterinary-)diagnostic questions in relation to specific binding of various molecule species (small molecules (active-ingredient libraries, natural substances), RNAs, proteins and DNA) and/or catalysis in bioassays and to build bioanalysis systems (bioassay), diagnostic devices, possibly companion diagnostic devices, and/or therapies on the results.
7. Molecules according to 1. to 4. that serve their gene products, transfected cells or parts of cells, to resolve questions in the field of immunoanalytics and immunodiagnostics, to resolve immunoanalytical and diagnostic questions and possibly build treatments thereon.

8. Molecules according to 1. to 4. that serve their gene products, transfected cells or parts of cells, to develop analytical high-throughput systems or to operate these.
9. Molecules according to 1. to 4. that serve their gene products, transfected cells or parts of cells directly or indirectly, to develop immunotherapeutic agents that are used directly (polyclonal or monoclonal antibodies or artificial molecules with similar possible uses).
10. Molecules according to 1. to 3. that serve their gene products, transfected cells or parts of cells, are provided to third parties in large quantities from fermentation/bioproduction for use and utilisation.

REFERENCES

1. Berggard, T Linse, S. & James, P. Methods for the detection and analysis of protein-protein interactions. *Proteomics* 7, 2833-2842, doi:10.1002/pmic.200700131 (2007).
2. Glick, B. S. & Malhotra, V. The curious status of the Golgi apparatus. *Cell* 95, 883-889 (1998).
3. Call, M. E. & Wucherpfennig, K. W. The T cell receptor: critical role of the membrane environment in receptor assembly and function. *Annu Rev Immunol* 23, 101-125, doi:10.1146/annurev.immunol.23.021704.115625 (2005).
4. Sachs, J. N. & Engelman, D. M. Introduction to the membrane protein reviews: the interplay of structure, dynamics, and environment in membrane protein function. *Annu Rev Biochem* 75, 707-712, doi:10.1146/annurev.biochem.75.110105.142336 (2006).
5. Macher, B. A. & Yen, T.-Y. Proteins at membrane surfaces—a review of approaches. *Molecular BioSystems* 3, 705-713, doi:10.1039/13708581H (2007).
6. Lodish, H. F. *Molecular cell biology*. (W.H. Freeman, 2013).
7. Nicolson, G. L. The Fluid-Mosaic Model of Membrane Structure: still relevant to understanding the structure, function and dynamics of biological membranes after more than 40 years. *Biochim Biophys Acta* 1838, 1451-1466, doi:10.1016/j.bbamem.2013.10.019 (2014).
8. Whitelegge, J. P. Integral membrane proteins and bilayer proteomics. *Anal Chem* 85, 2558-2568, doi:10.1021/ac303064a (2013).
9. Smith, G. P. Filamentous fusion phage: novel expression vectors that display cloned antigens on the virion surface. *Science* 228, 1315-1317 (1985)
10. Crameri, R., Jaussi, R., Menz, G. & Blaser, K. Display of expression products of cDNA libraries on phage surfaces. A versatile screening system for selective isolation of genes by specific gene-product/ligand interaction. *Eur J Biochem* 226, 53-58 (1994).
11. Gu, H. et al. A phage display system for studying the sequence determinants of protein folding. *Protein Sci* 4, 1108-1117, doi:10.1002/pro.5560040609 (1995).
12. Kehoe, J. W. & Kay, B. K. Filamentous phage display in the new millennium. *Chem Rev* 105, 4056-4072, doi:10.1021/cr000261 r (2005).
13. Chen, W. & Georgiou, G. Cell-Surface display of heterologous proteins: From high-throughput screening to environmental applications. *Biotechnol Bioeng* 79, 496-503, doi:10.1002/bit.10407 (2002).
14. Hoischen, C. et al. Novel bacterial membrane surface display system using cell wall-less L-forms of *Proteus mirabilis* and *Escherichia coli*. *App/Environ Microbiol* 68, 525-531 (2002).
15. Lee, S. Y., Choi, J. H. & Xu, Z. Microbial cell-surface display. *Trends Biotechnol* 21, 45-52 (2003).
16. Rutherford, N. & Mourez, M. Surface display of proteins by gram-negative bacterial autotransporters. *Microb Cell Fact* 5, 22, doi: 10.1186/1475-2859-5-22 (2006).
17. Yang, Z., Liu, Q., Wang, Q. & Zhang, Y. Novel bacterial surface display systems based on outer membrane anchoring elements from the marine bacterium *Vibrio anguillarum*. *Appl Environ Microbiol* 74, 4359-4365, doi: 10.1128/AEM.02499-07 (2008).
18. van Bloois, E., Winter, R. T., Kolmar, H. & Fraaije, M. W. Decorating microbes: surface display of proteins on *Escherichia coli*. *Trends Biotechnol* 29, 79-86, doi: 10.1016/j.tibtech.2010.11.003 (2011).
19. Nicolay, T., Vanderleyden, J. & Spaepen, S. Autotransporter-based cell surface display in Gram-negative bacteria. *Crit Rev Microbiol*, doi:10.3109/1040841X.2013.804032 (2013).
20. Han, M.-J. & Lee, S. H. *An efficient bacterial surface display system based on a novel outer membrane anchoring element from the Escherichia coli protein YiaT*. (2014).
21. Boublik, Y., Di Bonito, P. & Jones, I. M. Eukaryotic virus display: engineering the major surface glycoprotein of the *Autographa californica* nuclear polyhedrosis virus (AcNPV) for the presentation of foreign proteins on the virus surface. *Biotechnology* (N Y) 13, 1079-1084 (1995).
22. Grabherr, R., Ernst, W., Doblhoff-Dier, O., Sara, M. & Katinger, H. Expression of foreign proteins on the surface of *Autographa californica* nuclear polyhedrosis virus. *BioTechniques* 22, 730-735 (1997).
23. Kim, S. Y., Sohn, J. H., Pyun, Y. R. & Choi, E. S. A cell surface display system using novel GPI-anchored proteins in *Hansenula polymorpha*. *Yeast* 19, 1153-1163, doi: 10.1002/yea.911 (2002).
24. Rahman, M. M. & Gopinathan, K. P. *Bombyx mori* nucleopolyhedrovirus-based surface display system for recombinant proteins. *J Gen Virol* 84, 2023-2031 (2003).
25. Baneyx, F. & Mujacic, M. Recombinant protein folding and misfolding in *Escherichia coli*. *Nat Biotechnol* 22, 1399-1408, doi:10.1038/nbt1029 (2004).
26. Raty, J. K. et al. Enhanced gene delivery by avidin-displaying baculovirus. *Mol Ther* 9, 282-291, doi: 10.1016/j.ymthe.2003.11.004 (2004).
27. Mao, H., Song, J., Liang, C., Yu, Z. & Chen, X. Construction of eukaryotic surface display based on the baculoviral F protein. *BioTechniques* 41, 266, 268, 270 passim (2006).
28. Weerapana, E. & Imperiali, B. Asparagine-linked protein glycosylation: from eukaryotic to prokaryotic systems. *Glycobiology* 16, 91R-101R, doi:10.1093/glycob/cwj099 (2006).
29. Wang, Q., Li, L., Chen, M., Qi, Q. & Wang, P. G. Construction of a novel system for cell surface display of heterologous proteins on *Pichia pastoris*. *Biotechnol Lett* 29, 1561-1566, doi:10.1007/s10529-007-9430-6 (2007).
30. Chesnut, J. D. et al. Selective isolation of transiently transfected cells from a mammalian cell population with vectors expressing a membrane anchored single-chain antibody. *J Immunol Methods* 193, 17-27 (1996).
31. Ellmark, P., Ohlin, M., Borrebaeck, C. A. & Furebring, C. A novel mammalian display system for the selection of protein-protein interactions by decoy receptor engagement. *J Mol Recognit* 17, 316-322, doi:10.1002/jmr.678 (2004).
32. Zhou, C., Jacobsen, F. W., Cai, L., Chen, Q. & Shen, W. D. Development of a novel mammalian cell surface antibody display platform. *MAbs* 2, 508-518, doi: 10.4161/mabs.2.5.12970 (2010).

33. Tomimatsu, K. et al. A rapid screening and production method using a novel mammalian cell display to isolate human monoclonal antibodies. *Biochem Biophys Res Commun* 441, 59-64, doi: 10.1016/j.bbrc.2013.10.007 (2013).
34. Stipp, C. S., Kolesnikova, T. V. & Hemler, M. E. Functional domains in tetraspanin proteins. *Trends Biochem Sci* 28, 106-112 (2003).
35. Kovalenko, O. V., Metcalf, D. G., DeGrado, W. F. & Hemler, M. E. Structural organization and interactions of transmembrane domains in tetraspanin proteins. *BMC Struct Biol* 5, 11, doi:10.1186/1472-6807-5-11 (2005).
36. Hemler, M. E. Targeting of tetraspanin proteins—potential benefits and strategies. *Nat Rev Drug Discov* 7, 747-758, doi:10.1038/nrd2659 (2008).
37. Levy, S. & Shoham, T. The tetraspanin web modulates immune-signalling complexes. *Nat Rev Immunol* 5, 136-148, doi:10.1038/nri1548 (2005).
38. Rubinstein, E. et al. CD9, CD63, CD81, and CD82 are components of a surface tetraspan network connected to HLA-DR and VLA integrins. *Eur J Immunol* 26, 2657-2665, doi:10.1002/eji.1830261117 (1996).
39. Green, M. R. & Sambrook, J. *Molecular cloning: a laboratory manual*. 1. (Cold Spring Harbor Laboratory Press, 2012).
40. Rognan, D. Rational design of protein-protein interaction inhibitors. *MedChemComm* 6, 51-60, doi:10.1039/C4MD00328D (2015).
41. Jin, L., Wang, W. & Fang, G. Targeting protein-protein interaction by small molecules. *Annu Rev Pharmacol Toxicol* 54, 435-456, doi:10.1146/annurev-pharmtox-011613-140028 (2014).
42. Milroy, L. G., Grossmann, T. N., Hennig, S., Brunsveld, L. & Ottmann, C. Modulators of protein-protein interactions. *Chem Rev* 114, 4695-4748, doi:10.1021/cr400698c (2014).
43. Rao, V. S., Srinivas, K., Sujini, G. N. & Kumar, G. N. Protein-protein interaction detection: methods and analysis. *Int J Proteomics* 2014, 147648, doi:10.1155/2014/147648 (2014).
44. Arkin, M. R. & Wells, J. A. Small-molecule inhibitors of protein-protein interactions: progressing towards the dream. *Nat Rev Drug Discov* 3, 301-317, doi:10.1038/nrd1343 (2004).
45. Jones, S. & Thornton, J. M. Principles of protein-protein interactions. *Proc Natl Acad Sci USA* 93, 13-20 (1996).
46. Jones, S. & Thornton, J. M. Protein-protein interactions: a review of protein dimer structures. *Prog Biophys Mol Biol* 63, 31-65 (1995).
47. Sudhof, T. C. The synaptic vesicle cycle: a cascade of protein-protein interactions. *Nature* 375, 645-653, doi: 10.1038/375645a0 (1995).
48. Mullard, A. Protein-protein interaction inhibitors get into the groove. *Nat Rev Drug Discov* 11, 173-175, doi: 10.1038/nrd3680 (2012).
49. Ivanusic, D., Eschricht, M. & Denner, J. Investigation of membrane protein-protein interactions using correlative FRET-PLA. *BioTechniques* 57, 188-198, doi:10.2144/000114215 (2014).
50. Kremers, G. J., Goedhart, J., van Munster, E. B. & Gadella, T. W., Jr. Cyan and yellow super fluorescent proteins with improved brightness, protein folding, and FRET Forster radius. *Biochemistry* 45, 6570-6580, doi: 10.1021/bi0516273 (2006).
51. Adachi, A. et al. Production of acquired immunodeficiency syndrome-associated retrovirus in human and non-human cells transfected with an infectious molecular clone. *J Virol* 59, 284-291 (1986).
52. Stéphanie Charrin, François le Naour, Olivier Silvie, Pierre-Emmanuel Milhiet, Claude Boucheix, Eric Rubinstein, Lateral organization of membrane proteins: tetraspanins spin their web, *Bioch. J.* (2009), 420 (2) 133-154; doi: 10.1042/BJ20082422.
53. A Voller, A Bartlett, D E Bidwell, Enzyme immunoassays with special reference to ELISA techniques, *J Clin Pathol.*, 1978 June, 31(6): 507-520.
54. Hughes R A, Miklos A E, Ellington A D, Gene synthesis: methods and applications, Methods Enzymol. 2011; 498: 277-309, doi:10.2016/B978-0-12-385120-8.00012-7

The invention claimed is:

1. A fusion protein comprising a first domain (i), a second domain (ii) and a third domain (iii), wherein the second domain is disposed between the first and the third domain, wherein said first (i), second (ii) and third domain (iii) are as follows:
   (i) a partial sequence of a tetraspanin, which includes the transmembrane domain 1 (TM1), the small extracellular loop (SEL), the transmembrane domain 2 (TM2), the small intracellular loop (SIL) and the transmembrane domain 3 (TM3), or comprises a sequence homologous thereto with a sequence identity of at least 95% over the entire length,
   (ii) a peptide with a predetermined amino acid sequence having a sequence identity of less than 70% over the entire length with respect to the large extracellular loop (LEL) of a tetraspanin and
   (iii) a partial sequence of a tetraspanin, comprising the transmembrane domain 4 (TM4) or a sequence homologous thereto with a sequence identity of at least 95% over the entire length,
   wherein the second domain (ii) further comprises one or more protease recognition sequences, which are disposed C- and/or N-terminally to the peptide with the predetermined amino acid sequence.

2. The fusion protein according to claim 1, wherein the second domain (ii) further comprises one or more partial sequences of the LEL of a tetraspanin or sequences homologous thereto with a sequence identity of at least 95% over the entire length, which are disposed C- and/or N-terminally to the peptide with the predetermined amino acid sequence.

3. The fusion protein according to claim 1, wherein the peptide is selected from an epitope, a protein, an antigen, or an enzyme.

4. The fusion protein according to claim 1, further comprising a fourth domain (iv) on the N-terminus of the fusion protein and/or a fifth domain (v) on the C-terminus of the fusion protein.

5. The fusion protein according to claim 4, wherein the fourth and/or fifth domain comprises a tag.

6. The fusion protein according to claim 5, wherein the tag is an affinity tag or fluorescent tag.

7. The fusion protein according to claim 1, wherein flexible linkers are disposed between the first and second domain and/or between the second and the third domain.

8. A nucleic acid molecule that codes for a fusion protein according to claim 1.

9. A nucleic acid molecule comprising a first sequence segment (i), a second sequence segment (ii) and a third sequence segment (iii), wherein the second sequence segment is disposed between the first and the third sequence segment, wherein said first (i), second (ii) and third (iii) sequence segment are as follows:
   (i) nucleic acid molecule codes for a partial sequence of a tetraspanin, which includes the transmembrane domain 1 (TM1), the small extracellular loop (SEL), the transmembrane domain 2 (TM2), the small intracellular loop (SIL) and the transmembrane domain 3 (TM3), or a sequence homologous thereto with a sequence identity of at least 95% over the entire length,
   (ii) nucleic acid molecule comprises a multiple cloning site and
   (iii) nucleic acid molecule codes for a partial sequence of a tetraspanin, comprising the transmembrane domain 4 (TM4) or a sequence homologous thereto with a sequence identity of at least 95% over the entire length,
   wherein the second nucleic acid molecule (ii) further comprises one or more protease recognition sequences, which are disposed C- and/or N-terminally to the multiple cloning site.

10. A vector comprising a nucleic acid molecule according to claim 8.

11. A vector comprising a nucleic acid molecule according to claim 9, preferably operably linked to an expression control sequence.

12. The vector according to claim 10 wherein said nucleic acid molecule is operably linked to an expression control sequence.

13. A cell comprising either (a) a nucleic acid molecule according to claim 8 or (b) a vector comprising said nucleic acid molecule.

14. A cell according to claim 13, wherein the cell is a eukaryotic cell.

15. A cell according to claim 13, which furthermore was transformed or transfected with at least one further nucleic acid molecule or at least one further expression vector.

16. The cell according to claim 14, wherein the cell is a mammalian cell.

17. The cell according to claim 16, wherein the cell is a human cell.

18. A cell according to claim 13 for use as a vaccine or as a medication.

19. A membrane preparation that was obtained from a cell according to claim 13, comprising an isolated cellular membrane.

20. A synthetic membrane system, comprising a fusion protein according to claim 1 and an isolated membrane.

21. A synthetic membrane system comprising a membrane and either (a) a nucleic acid molecule according to claim 8 or (b) a vector comprising said nucleic acid molecule.

22. A kit, comprising
   (i) a nucleic acid molecule according to claim 8 or a vector comprising said nucleic acid molecule, and
   (ii) a cell or cell membrane.

23. A kit, comprising
   (i) a nucleic acid molecule according to claim 9 or a vector comprising said nucleic acid, and
   (ii) a cell or membrane.

24. A vaccine or medication comprising the membrane preparation according to claim 19.

25. A vaccine or medication comprising the synthetic membrane system according to claim 20.

26. A method for the anchoring of a peptide with a predetermined amino-acid sequence on a membrane comprising the steps:
   (a) provision of a membrane, and
   (b) bringing into contact of the membrane with a fusion protein according to claim 1 under conditions where anchoring of the fusion protein takes place in the membrane.

27. A method for anchoring a peptide with a predetermined amino-acid sequence on a membrane, comprising:
   (a) providing a membrane,
   (b) providing a nucleic acid molecule encoding a fusion protein according to claim 1 and a system for expression of said nucleic acid molecule, wherein said nucleic acid is operably linked to an expression control sequence, under conditions wherein a fusion protein is expressed, and
   (c) anchoring said fusion protein in the membrane, wherein the partial sequences of tetraspanin transport and anchor said fusion protein in the membrane.

28. A method for the presentation of a peptide with a predetermined amino-acid sequence on the surface of a cell, comprising the steps:
  (a) provision of a cell according to claim 13,
  (b) cultivation of the cell under conditions wherein a fusion protein is expressed.

* * * * *

SEQUENCE LISTING

```
<160> NUMBER OF SEQ ID NOS: 46

<210> SEQ ID NO 1
<211> LENGTH: 4832
<212> TYPE: DNA
<213> ORGANISM: artificial sequence
<220> FEATURE:
<223> OTHER INFORMATION: DNA sequence of pA4E2l1(CD63delLEL)

<400> SEQUENCE: 1
cctcgaggaa ggctactacg cctaagctac cgacaggttg gctgataagt ccccggtctc      60
aaggcgcgcc tagttattaa tagtaatcaa ttacggggtc attagttcat agcccatata     120
tggagttccg cgttacataa cttacggtaa atggcccgcc tggctgaccg cccaacgacc     180
cccgcccatt gacgtcaata atgacgtatg ttcccatagt aacgccaata gggactttcc     240
attgacgtca atgggtggag tatttacggt aaactgccca cttggcagta catcaagtgt     300
atcatctgcc aagtacgccc cctattgacg tcaatgacgg taaatggccc gcctggcatt     360
atgcccagta catgacctta tgggactttc ctacttggca gtacatctac gtattagtca     420
tcgctattac cacggtgatg cggttttggc agtacatcaa tgggcgtgga tagcggtttg     480
actcacgggg atttccaagt ctccacccca ttgacgtcaa tgggagtttg ttttggcacc     540
```

```
aaaatcaacg ggactttcca aaatgtcgta acaactccgc cccattgacg caaatgggcg    600
gtaggcgtgt acggtgggag gtctatataa gcagagctct ctggctaact agagaaccca    660
ctgcttactg gcttatcgaa attaatacga ctcactatag gaagccgcca cctgctagca    720
atttatagcc accatggatt acaaggatga cgacgataag cccatggcgg tggaaggagg    780
aatgaaatgt gtgaagttct tgctctacgt cctcctgctg gccttttgcg cctgtgcagt    840
gggactgatt gccgtgggtg tcggggcaca gcttgtcctg agtcagacca taatccaggg    900
ggctacccct ggctctctgt tgccagtggt catcatcgca gtgggtgtct tcctcttcct    960
ggtggctttt gtgggctgct gcggggcctg caaggagaac tattgtctta tgattacgtt   1020
tgccatcttt ctgtctctta tcatgttggt ggaggtggcc gcagccattg ctggctatgt   1080
gtttagagat aagctgcaag aattcgagaa tctgtacttt cagtcgaagc ttggatccct   1140
gcagcatcac catcaccatc acgaaaacct ctatttccag agcgaacaga aactgatatc   1200
cgaagaagat ctggatatcg gaggcggagg caaaaatgtg ctggtggtag ctgccgcagc   1260
ccttggaatt gcttttgtcg aggttttggg aattgtcttt gcctgctgcc tcgtgaagag   1320
tatcagaagt ggctacgagg tgatgaaact tatcgatacc gtcgatctcc atatgccagc   1380
catgaagata gaatgcagga ttacaggcac cctgaatggc gtggagttcg agctggtcgg   1440
gggtggagaa ggaacacctg agcagggccg aatgacgaac aagatgaaga gcaccaaagg   1500
agccctgaca tttagcccct atctcctctc tcatgttatg ggctacggct tttatcactt   1560
cgggacttac ccaagcggat atgaaaaccc tttccttcac gccataaaca atgggggtta   1620
caccaacacc cggattgaga aatatgagga cggtggcgtg ttgcatgtct ccttcagcta   1680
cagatatgag gctggtcgcg tgatcggaga ttttaaggtt gtgggcacag gctttccaga   1740
agactccgta atcttcaccg acaagatcat tcggtctaat gccacggtgg agcatcttca   1800
ccctatgggc gataatgtcc tcgtcgggag cttttgccaga acttttttcac tgagggatgg   1860 gggatactat tcattcgtcg tagactccca catgcacttt aaatccgcaa tccacccatc   1920
aatcctgcaa aacggagggc ctatgtttgc gttcagacgt gtagaggagc tgcattctaa   1980
cactgaactc ggaatcgttg aataccagca cgctttcaaa actcccattg cattcgctgg   2040
gccctgatca tgagagttta acataaagc ctcgactgtg ccttctagtt gccagccatc   2100
tgttgtttgc ccctcccccg tgccttcctt gaccctggaa ggtgccactc ccactgtcct   2160
ttcctaataa aatgaggaaa ttgcatcgca ttgtctgagt aggtgtcatt ctattctggg   2220
gggtggggtg gggcaggaca gcaaggggga ggattgggaa gacaatagca ggcatgctgg   2280
ggatgcggtg ggctctatgg aaaaaacgcg cgcggatata atataacttc gtataatgta   2340
tgctatacga agttatatat aatgcgtcga cgcactcaac cctatctcgg tctattcttt   2400
tgatttataa gggattttgc cgatttcggc ctattggtta aaaaatgagc tgatttaaca   2460
aaaatttaac gcgaatttta acaaaatatt aacgcttaca atttaggtgg cacttttcgg   2520
ggaaatgtgc gcggaacccc tatttgttta ttttttctaaa tacattcaaa tatgtatccg   2580
ctcatgagac aataaccctg ataaatgctt caataatatt gaaaaaggaa gagtatgagt   2640
attcaacatt tccgtgtcgc ccttattccc ttttttgcgg catttgcct tcctgttttt   2700 gctcacccag aaacgctggt gaaagtaaaa gatgctgaag atcagttggg tgccgagtg   2760 ggttacatcg aactggatct caacagcggt aagatccttg agagttttcg ccccgaagaa   2820
cgttttccaa tgatgagcac ttttaaagtt ctgctatgtg gcgcggtatt atcccgtatt   2880
```

```
gacgccgggc aagagcaact cggtcgccgc atacactatt ctcagaatga cttggttgag    2940
tattcaccag tcacagaaaa gcatcttacg gatggcatga cagtaagaga attatgcagt    3000
gctgccataa ccatgagtga taacactgcg gccaacttac ttctgacaac gattggagga    3060
ccgaaggagc taaccgcttt tttgcacaac atggggatc atgtaactcg ccttgatcgt     3120
tgggaaccgg agctgaatga agccatacca acgacgagc gtgacaccac gatgcctgta     3180
gcaatggcaa caacgttgcg taaactatta actggcgaac tacttactct agcttcccgg    3240
caacaattga tagactggat ggaggcggat aaagttgcag gaccacttct gcgctcggcc    3300
cttccggctg gctggtttat tgctgataaa tctggagccg gtgagcgtgg ttctcgcggt    3360
atcattgcag cactggggcc agatggtaag ccctcccgta tcgtagttat ctacacgacg    3420
gggagtcagg caactatgga tgaacgaaat agacagatcg ctgagatagg tgcctcactg    3480
attaagcatt ggtaactgtc agaccaagtt tactcatata tactttagat tgatttaaaa    3540
cttcattttt aatttaaaag gatctaggtg aagatccttt ttgataatct tatgaccaaa    3600
atcccttaac gtgagttttc gttccactga gcgtcagacc gcgatcgcag cagaccgggg    3660
acttatcagc caacctgtcg ttaattaacc atgtcagccg ttaagtgttc ctgtgtcact    3720
caaaattgct ttgagaggct ctaagggctt ctcagtgcgt tacatccctg gcttgttgtc    3780
cacaaccgtt aaaccttaaa ggctttaaaa gccttatata ttcttttttt cttataaaa     3840
cttaaaacct tagaggctat ttaagttgct gatttatatt aattgaagag cattataccaa   3900
aaatccctta acgtgagttt tcgttccact gagcgtcaga ccccgtagaa aagatcaaag    3960
gatcttcttg agatcctttt tttctgcgcg taatatgctg cttgcaaaca aaaaaaccac    4020
cgctaccagc ggtggtttgt ttgccggatc aagagctacc aactcttttt ccgaaggtaa    4080
ctggcttcag cagagcgcag ataccaaata ctgtccttct agtgtagccg tagttaggcc    4140
accacttcaa gaactctgta gcaccgccta catacctcgc tctgctaatc ctgttaccag    4200
tggctgctgc cagtggcgat aagtcgtgtc ttaccgggtt ggactcaaga cgatagttac    4260
cggataaggc gcagcggtcg ggctgaacgg ggggttcgtg cacacagccc agcttggagc    4320
gaacgaccta caccgaactg agatacctac agcgtgagct atgagaaagc gccacgcttc    4380
ccgaagggag aaaggcggac aggtatccgg taagcggcag ggtcggaaca ggagagcgca    4440
cgagggagct tccaggggga aacgcctggt atctttatag tcctgtcggg tttcgccacc    4500
tctgacttga gcgtcgattt tgtgatgct cgtcagggg gcggagccta tggaaaaacg     4560
ccagcaacgc ggcctttta cggttcctgg cctttgctg gcttttgct catattagct       4620
cttcaaattt tattgttcaa acatgagagc ttagtacgtg aaacatgaga gcttagtacg    4680
ttagccatga gcttagta cgttagccat gagggttag ttcgttaaac atgagagctt       4740
agtacgttaa acatgagagc ttagtacgtg aaacatgaga gcttagtacg tactatcaac    4800
aggttgaact gctgatcttc agatcatata at                                   4832
```

<210> SEQ ID NO 2
<211> LENGTH: 474
<212> TYPE: DNA
<213> ORGANISM: Artificial Sequence
<220> FEATURE:
<223> OTHER INFORMATION: DNA sequence of CD63delLEL
<220> FEATURE:
<221> NAME/KEY: misc_feature
<222> LOCATION: (1)..(330)
<223> OTHER INFORMATION: TM1-TM3
<220> FEATURE:
<221> NAME/KEY: misc_feature

```
<222> LOCATION: (331)..(360)
<223> OTHER INFORMATION: Minimal linker
<220> FEATURE:
<221> NAME/KEY: misc_feature
<222> LOCATION: (361)..(474)
<223> OTHER INFORMATION: TM4

<400> SEQUENCE: 2
atggcggtgg aaggaggaat gaaatgtgtg aagttcttgc tctacgtcct cctgctggcc    60
ttttgcgcct gtgcagtggg actgattgcc gtgggtgtcg gggcacagct tgtcctgagt   120
cagaccataa tccagggggc tacccctggc tctctgttgc cagtggtcat catcgcagtg   180
ggtgtcttcc tcttcctggt ggcttttgtg ggctgctgcg gggcctgcaa ggagaactat   240
tgtcttatga tcacgtttgc catctttctg tctcttatca tgttggtgga ggtggccgca   300
gccattgctg gctatgtgtt tagagataag ctgcaggaat cgatatcgg aggaggagga   360 aaaaatgtgc tggtggtagc tgcagcagcc cttggaattg cttttgtcga ggttttggga   420
attgtctttg cctgctgcct cgtgaagagt atcagaagtg gctacgaggt gatg          474

<210> SEQ ID NO 3
<211> LENGTH: 158
<212> TYPE: PRT
<213> ORGANISM: artificial sequence
<220> FEATURE:
<223> OTHER INFORMATION: Protein sequence of CD63delLEL
<220> FEATURE:
<221> NAME/KEY: MISC_FEATURE
<222> LOCATION: (1)..(110)
<223> OTHER INFORMATION: TM1-TM3
<220> FEATURE:
<221> NAME/KEY: MISC_FEATURE
<222> LOCATION: (111)..(120)
<223> OTHER INFORMATION: Minimal linker
<220> FEATURE:
<221> NAME/KEY: MISC_FEATURE
<222> LOCATION: (121)..(158)
<223> OTHER INFORMATION: TM4

<400> SEQUENCE: 3

Met Ala Val Glu Gly Gly Met Lys Cys Val Lys Phe Leu Leu Tyr Val
1               5                   10                  15

Leu Leu Leu Ala Phe Cys Ala Cys Ala Val Gly Leu Ile Ala Val Gly
                20                  25                  30

Val Gly Ala Gln Leu Val Leu Ser Gln Thr Ile Ile Gln Gly Ala Thr
            35                  40                  45

Pro Gly Ser Leu Leu Pro Val Val Ile Ile Ala Val Gly Val Phe Leu
        50                  55                  60

Phe Leu Val Ala Phe Val Gly Cys Cys Gly Ala Cys Lys Glu Asn Tyr
65                  70                  75                  80

Cys Leu Met Ile Thr Phe Ala Ile Phe Leu Ser Leu Ile Met Leu Val
                85                  90                  95

Glu Val Ala Ala Ala Ile Ala Gly Tyr Val Phe Arg Asp Lys Leu Gln
                100                 105                 110

Glu Phe Asp Ile Gly Gly Gly Lys Asn Val Leu Val Val Ala Ala
            115                 120                 125

Ala Ala Leu Gly Ile Ala Phe Val Glu Val Leu Gly Ile Val Phe Ala
        130                 135                 140

Cys Cys Leu Val Lys Ser Ile Arg Ser Gly Tyr Glu Val Met
145                 150                 155

<210> SEQ ID NO 4
```

-continued

<210> SEQ ID NO 4
<211> LENGTH: 30
<212> TYPE: DNA
<213> ORGANISM: artificial sequence
<220> FEATURE:
<223> OTHER INFORMATION: Primer PA1-01

<400> SEQUENCE: 4
tttttctcga gatggtgagc aagggcgagg                                    30

<210> SEQ ID NO 5
<211> LENGTH: 32
<212> TYPE: DNA
<213> ORGANISM: artificial sequence
<220> FEATURE:
<223> OTHER INFORMATION: Primer PA1-02

<400> SEQUENCE: 5
tttttgggcc catcttgtac agctcgtcca tg                                 32

<210> SEQ ID NO 6
<211> LENGTH: 33
<212> TYPE: DNA
<213> ORGANISM: artificial sequence
<220> FEATURE:
<223> OTHER INFORMATION: Primer PA1-03

<400> SEQUENCE: 6 tttttttggat ccatggcggt ggaaggagga atg                               33

<210> SEQ ID NO 7
<211> LENGTH: 27
<212> TYPE: DNA
<213> ORGANISM: artificial sequence
<220> FEATURE:
<223> OTHER INFORMATION: Primer PA1-04

<400> SEQUENCE: 7
tttttctgca gcttatctct aaacaca                                       27

<210> SEQ ID NO 8
<211> LENGTH: 36
<212> TYPE: DNA
<213> ORGANISM: artificial sequence
<220> FEATURE:
<223> OTHER INFORMATION: Primer PA1-05

<400> SEQUENCE: 8
tttttgatat cggaggagga ggaaaaaatg tgctgg                             36

<210> SEQ ID NO 9
<211> LENGTH: 33
<212> TYPE: DNA
<213> ORGANISM: artificial sequence
<220> FEATURE:
<223> OTHER INFORMATION: Primer PA1-06

<400> SEQUENCE: 9 tttttttaagc ttcatcacct cgtagccact tct                               33

<210> SEQ ID NO 10
<211> LENGTH: 31
<212> TYPE: DNA
<213> ORGANISM: artificial sequence
<220> FEATURE:
<223> OTHER INFORMATION: Primer PA1-07

<400> SEQUENCE: 10 ttttttgaatt catggtgagc aagggcgagg a                         31

<210> SEQ ID NO 11
<211> LENGTH: 31
<212> TYPE: DNA
<213> ORGANISM: artificial sequence
<220> FEATURE:
<223> OTHER INFORMATION: Primer PA1-08

<400> SEQUENCE: 11
tttttgatat cctttctgag tccggacttg t                         31

<210> SEQ ID NO 12
<211> LENGTH: 30
<212> TYPE: DNA
<213> ORGANISM: artificial sequence
<220> FEATURE:
<223> OTHER INFORMATION: Primer PA1-09

<400> SEQUENCE: 12
tttttgaatt cctgacggta caggccagac                           30

<210> SEQ ID NO 13
<211> LENGTH: 31
<212> TYPE: DNA
<213> ORGANISM: artificial sequence
<220> FEATURE:
<223> OTHER INFORMATION: Primer PA1-10

<400> SEQUENCE: 13
tttttgatat cgttaaacca attccacaaa c                         31

<210> SEQ ID NO 14
<211> LENGTH: 30
<212> TYPE: DNA
<213> ORGANISM: artificial sequence
<220> FEATURE:
<223> OTHER INFORMATION: Primer PA1-11

<400> SEQUENCE: 14
tttttgatat cctgcctaac tctattcact                           30

<210> SEQ ID NO 15
<211> LENGTH: 30
<212> TYPE: DNA
<213> ORGANISM: artificial sequence
<220> FEATURE:
<223> OTHER INFORMATION: Primer PA1-12

<400> SEQUENCE: 15
tttttgaatt cattgaagaa tcgcaaaacc                           30

<210> SEQ ID NO 16
<211> LENGTH: 31
<212> TYPE: DNA
<213> ORGANISM: artificial sequence
<220> FEATURE:
<223> OTHER INFORMATION: Primer PA1-13

<400> SEQUENCE: 16
tttttgatat cttttatata ccacagccaa t                         31

<210> SEQ ID NO 17
<211> LENGTH: 714
<212> TYPE: DNA

<213> ORGANISM: homo sapiens
<220> FEATURE:
<221> NAME/KEY: misc_feature
<222> LOCATION: (1)..(3)
<223> OTHER INFORMATION: start codon

<400> SEQUENCE: 17

```
atggcggtgg aaggaggaat gaaatgtgtg aagttcttgc tctacgtcct cctgctggcc    60
ttttgcgcct gtgcagtggg actgattgcc gtgggtgtcg gggcacagct tgtcctgagt   120
cagaccataa tccagggggc taccctggc tctctgttgc cagtggtcat catcgcagtg    180
ggtgtcttcc tcttcctggt ggcttttgtg ggctgctgcg gggcctgcaa ggagaactat   240
tgtcttatga tcacgtttgc catctttctg tctcttatca tgttggtgga ggtggccgca   300
gccattgctg ctatgtgtt tagagataag gtgatgtcag agtttaataa caacttccgg   360
cagcagatgg agaattaccc gaaaaacaac cacactgctt cgatcctgga caggatgcag   420
gcagatttta gtgctgtgg ggctgctaac tacacagatt gggagaaaat cccttccatg   480
tcgaagaacc gagtccccga ctcctgctgc attgatgtta ctgtgggctg tgggattaat   540
ttcaacgaga aggcgatcca taaggagggc tgtgtggaga agattggggg ctggctgagg   600
aaaaatgtgc tggtggtagc tgcagcagcc cttggaattc ttttgtcga ggttttggga   660
attgtctttg cctgctgcct cgtgaagagt atcagaagtg gctacgaggt gatg         714
```

<210> SEQ ID NO 18
<211> LENGTH: 238
<212> TYPE: PRT
<213> ORGANISM: homo sapiens
<220> FEATURE:
<221> NAME/KEY: MISC_FEATURE
<222> LOCATION: (1)..(238)
<223> OTHER INFORMATION: CD63; translated sequence to SEQ ID NO:17
      (Genbank Accession No: KF998086)

<400> SEQUENCE: 18

```
Met Ala Val Glu Gly Gly Met Lys Cys Val Lys Phe Leu Leu Tyr Val
1               5                   10                  15

Leu Leu Leu Ala Phe Cys Ala Cys Ala Val Gly Leu Ile Ala Val Gly
            20                  25                  30

Val Gly Ala Gln Leu Val Leu Ser Gln Thr Ile Ile Gln Gly Ala Thr
        35                  40                  45

Pro Gly Ser Leu Leu Pro Val Val Ile Ala Val Gly Val Phe Leu
    50                  55                  60

Phe Leu Val Ala Phe Val Gly Cys Cys Gly Ala Cys Lys Glu Asn Tyr
65                  70                  75                  80

Cys Leu Met Ile Thr Phe Ala Ile Phe Leu Ser Leu Ile Met Leu Val
                85                  90                  95

Glu Val Ala Ala Ala Ile Ala Gly Tyr Val Phe Arg Asp Lys Val Met
            100                 105                 110

Ser Glu Phe Asn Asn Phe Arg Gln Gln Met Glu Asn Tyr Pro Lys
        115                 120                 125

Asn Asn His Thr Ala Ser Ile Leu Asp Arg Met Gln Ala Asp Phe Lys
    130                 135                 140

Cys Cys Gly Ala Ala Asn Tyr Thr Asp Trp Glu Lys Ile Pro Ser Met
145                 150                 155                 160

Ser Lys Asn Arg Val Pro Asp Ser Cys Cys Ile Asp Val Thr Val Gly
                165                 170                 175

Cys Gly Ile Asn Phe Asn Glu Lys Ala Ile His Lys Glu Gly Cys Val
```

```
                    180                 185                 190
Glu Lys Ile Gly Gly Trp Leu Arg Lys Asn Val Leu Val Ala Ala
            195                 200                 205

Ala Ala Leu Gly Ile Ala Phe Val Glu Val Leu Gly Ile Val Phe Ala
        210                 215                 220

Cys Cys Leu Val Lys Ser Ile Arg Ser Gly Tyr Glu Val Met
225                 230                 235

<210> SEQ ID NO 19
<211> LENGTH: 771
<212> TYPE: DNA
<213> ORGANISM: homo sapiens
<220> FEATURE:
<221> NAME/KEY: misc_feature
<222> LOCATION: (18)..(21)
<223> OTHER INFORMATION: start codon

<400> SEQUENCE: 19
gctagcgcgg ccgccaccat ggattacaag gatgacgacg ataagagccc gggcggatcc      60
atgccggtca aggaggcac caagtgcatc aaatacctgc tgttcggatt taacttcatc     120
ttctggcttg ccgggattgc tgtccttgcc attggactat ggctccgatt cgactctcag     180
accaagagca tcttcgagca agaaactaat aataataatt ccagcttcta cacaggagtc     240
tatattctga tcggagccgg cgccctcatg atgctggtgg gcttcctggg ctgctgcggg     300
gctgtgcagg agtcccagtg catgctggga ctgttcttcg gcttcctctt ggtgatattc     360
gccattgaaa tagctgcggc catctgggga tattcccaca aggatgaggt gattaaggaa     420
gtccaggagt tttacaagga cacctacaac aagctgaaaa ccaaggatga gccccagcgg     480
gaaacgctga agccatcca ctatgcgttg aactgctgtg gtttggctgg gggcgtggaa     540
cagtttatct cagacatctg ccccaagaag gacgtactcg aaaccttcac cgtgaagtcc     600
tgtcctgatg ccatcaaaga ggtcttcgac aataaaattc cacatcatcg gcgcagtggc     660
atcggcattg ccgtggtcat gatatttggc atgatcttca gtatgatctt gtgctgtgct     720
atccgcagga accgcgagat ggtcaagctt atcgataccg tcgacctcga g             771

<210> SEQ ID NO 20
<211> LENGTH: 257
<212> TYPE: PRT
<213> ORGANISM: homo sapiens
<220> FEATURE:
<221> NAME/KEY: MISC_FEATURE
<222> LOCATION: (7)..(7)
<223> OTHER INFORMATION: starting methionine
<220> FEATURE:
<221> NAME/KEY: MISC_FEATURE
<222> LOCATION: (7)..(257)
<223> OTHER INFORMATION: CD9; translated sequence to SEQ ID NO:19
      (Genbank Accession No: NM_001769.3)

<400> SEQUENCE: 20

Ala Ser Ala Ala Ala Thr Met Asp Tyr Lys Asp Asp Asp Lys Ser
1               5                  10                  15

Pro Gly Gly Ser Met Pro Val Lys Gly Gly Thr Lys Cys Ile Lys Tyr
                20                  25                  30

Leu Leu Phe Gly Phe Asn Phe Ile Phe Trp Leu Ala Gly Ile Ala Val
            35                  40                  45

Leu Ala Ile Gly Leu Trp Leu Arg Phe Asp Ser Gln Thr Lys Ser Ile
        50                  55                  60

Phe Glu Gln Glu Thr Asn Asn Asn Asn Ser Ser Phe Tyr Thr Gly Val
```

```
            65                  70                  75                  80
Tyr Ile Leu Ile Gly Ala Gly Ala Leu Met Met Leu Val Gly Phe Leu
                    85                  90                  95

Gly Cys Cys Gly Ala Val Gln Glu Ser Gln Cys Met Leu Gly Leu Phe
                100                 105                 110

Phe Gly Phe Leu Leu Val Ile Phe Ala Ile Glu Ile Ala Ala Ala Ile
                115                 120                 125

Trp Gly Tyr Ser His Lys Asp Glu Val Ile Lys Glu Val Gln Glu Phe
                130                 135                 140

Tyr Lys Asp Thr Tyr Asn Lys Leu Lys Thr Lys Asp Glu Pro Gln Arg
145                 150                 155                 160

Glu Thr Leu Lys Ala Ile His Tyr Ala Leu Asn Cys Cys Gly Leu Ala
                    165                 170                 175

Gly Gly Val Glu Gln Phe Ile Ser Asp Ile Cys Pro Lys Lys Asp Val
                180                 185                 190

Leu Glu Thr Phe Thr Val Lys Ser Cys Pro Asp Ala Ile Lys Glu Val
                195                 200                 205

Phe Asp Asn Lys Phe His Ile Ile Gly Ala Val Gly Ile Gly Ile Ala
                210                 215                 220

Val Val Met Ile Phe Gly Met Ile Phe Ser Met Ile Leu Cys Cys Ala
225                 230                 235                 240

Ile Arg Arg Asn Arg Glu Met Val Lys Leu Ile Asp Thr Val Asp Leu
                    245                 250                 255

Glu

<210> SEQ ID NO 21
<211> LENGTH: 795
<212> TYPE: DNA
<213> ORGANISM: homo sapiens
<220> FEATURE:
<221> NAME/KEY: misc_feature
<222> LOCATION: (18)..(21)
<223> OTHER INFORMATION: start codon

<400> SEQUENCE: 21
gctagcgcgg ccgccaccat ggattacaag gatgacgacg ataagagccc gggcggatcc      60
atgggagtgg agggctgcac caagtgcatc aagtacctgc tcttcgtctt caatttcgtc     120
ttctggctgc tggaggcgt gatcctgggt gtggccctgt ggctccgcca tgacccgcag     180
accaccaacc tcctgtatct ggagctggga gacaagcccg cgcccaacac cttctatgta     240
ggcatctaca tcctcatcgc tgtgggcgct gtcatgatgt tcgttggctt cctgggctgc     300
tacggggcca tccaggaatc ccagtgcctg ctggggacgt tcttcacctg cctggtcatc     360
ctgtttgcct gtgaggtggc cgccggcatc tggggctttg tcaacaagga ccagatcgcc     420
aaggatgtga agcagttcta tgaccaggcc ctacagcagg ccgtggtgga tgatgacgcc     480
aacaacgcga aggctgtggt gaagaccttc acgagacgc ttgactgctg ggctccagc      540 acactgactg ctttgaccac ctcagtgctc aagaacaatt tgtgtccctc gggcagcaac     600
atcatcagca acctcttcaa ggaggactgc caccagaaga tcgacgacct cttctccggg     660
aagctgtacc tcatcggcat tgctgccatc gtggtcgctg tgatcatgat cttcgagatg     720
atcctgagca tggtgctgtg ctgtggcatc cggaacagct ccgtgtacaa gcttatcgat     780
accgtcgacc tcgag                                                     795

<210> SEQ ID NO 22
```

```
<211> LENGTH: 265
<212> TYPE: PRT
<213> ORGANISM: homo sapiens
<220> FEATURE:
<221> NAME/KEY: MISC_FEATURE
<222> LOCATION: (7)..(7)
<223> OTHER INFORMATION: starting methionine
<220> FEATURE:
<221> NAME/KEY: MISC_FEATURE
<222> LOCATION: (7)..(265)
<223> OTHER INFORMATION: CD81; translated sequence to SEQ ID NO: 21
      (Genbank Accession No: NM_004356.3)

<400> SEQUENCE: 22
```

Ala Ser Ala Ala Ala Thr Met Asp Tyr Lys Asp Asp Asp Lys Ser
1               5                   10                  15

Pro Gly Gly Ser Met Gly Val Glu Gly Cys Thr Lys Cys Ile Lys Tyr
                20                  25                  30

Leu Leu Phe Val Phe Asn Phe Val Phe Trp Leu Ala Gly Gly Val Ile
            35                  40                  45

Leu Gly Val Ala Leu Trp Leu Arg His Asp Pro Gln Thr Thr Asn Leu
50                  55                  60

Leu Tyr Leu Glu Leu Gly Asp Lys Pro Ala Pro Asn Thr Phe Tyr Val
65                  70                  75                  80

Gly Ile Tyr Ile Leu Ile Ala Val Gly Ala Val Met Met Phe Val Gly
                85                  90                  95

Phe Leu Gly Cys Tyr Gly Ala Ile Gln Glu Ser Gln Cys Leu Leu Gly
                100                 105                 110

Thr Phe Phe Thr Cys Leu Val Ile Leu Phe Ala Cys Glu Val Ala Ala
            115                 120                 125

Gly Ile Trp Gly Phe Val Asn Lys Asp Gln Ile Ala Lys Asp Val Lys
130                 135                 140

Gln Phe Tyr Asp Gln Ala Leu Gln Gln Ala Val Val Asp Asp Asp Ala
145                 150                 155                 160

Asn Asn Ala Lys Ala Val Val Lys Thr Phe His Glu Thr Leu Asp Cys
                165                 170                 175

Cys Gly Ser Ser Thr Leu Thr Ala Leu Thr Thr Ser Val Leu Lys Asn
                180                 185                 190

Asn Leu Cys Pro Ser Gly Ser Asn Ile Ile Ser Asn Leu Phe Lys Glu
            195                 200                 205

Asp Cys His Gln Lys Ile Asp Asp Leu Phe Ser Gly Lys Leu Tyr Leu
210                 215                 220

Ile Gly Ile Ala Ala Ile Val Val Ala Val Ile Met Ile Phe Glu Met
225                 230                 235                 240

Ile Leu Ser Met Val Leu Cys Cys Gly Ile Arg Asn Ser Ser Val Tyr
                245                 250                 255

Lys Leu Ile Asp Thr Val Asp Leu Glu
                260                 265

```
<210> SEQ ID NO 23
<211> LENGTH: 888
<212> TYPE: DNA
<213> ORGANISM: homo sapiens
<220> FEATURE:
<221> NAME/KEY: misc_feature
<222> LOCATION: (18)..(21)
<223> OTHER INFORMATION: start codon

<400> SEQUENCE: 23
```
gctagcgcgg ccgccaccat ggattacaag gatgacgacg ataagagccc gggcggatcc    60

-continued

```
atgggctcag cctgtatcaa agtcaccaaa tactttctct tcctcttcaa cttgatcttc    120
tttatcctgg gcgcagtgat cctgggcttc ggggtgtgga tcctggccga caagagcagt    180
ttcatctctg tcctgcaaac ctcctccagc tcgcttagga tgggggccta tgtcttcatc    240
ggcgtggggg cagtcactat gctcatgggc ttcctgggct gcatcggcgc cgtcaacgag    300
gtccgctgcc tgctggggct gtactttgct ttcctgctcc tgatcctcat tgcccaggtg    360
acggccgggg cactcttcta cttcaacatg ggcaagctga agcaggagat gggtggcatc    420
gtgactgagc tcattcgaga ctacaacagc agtcgcgagg acagcctgca ggatgcctgg    480
gactacgtgc aggctcaggt gaagtgctgc ggctgggtca gcttctacaa ctggacagac    540
aacgctgagc tcatgaatcg ccctgaggtc acctacccct gttcctgcga agtcaagggg    600
gaagaggaca acagcctttc tgtgaggaag ggcttctgcg aggcccccgg caacaggacc    660
cagagtggca accaccctga ggactggcct gtgtaccagg agggctgcat ggagaaggtg    720
caggcgtggc tgcaggagaa cctgggcatc atcctcggcg tgggcgtggg tgtggccatg    780
gtcgagctcc tggggatggt cctgtccatc tgcttgtgcc ggcacgtgca ttccgaagac    840
tacagcaagg tccccaagta caagcttatc gataccgtcg acctcgag                 888
```

```
<210> SEQ ID NO 24
<211> LENGTH: 296
<212> TYPE: PRT
<213> ORGANISM: homo sapiens
<220> FEATURE:
<221> NAME/KEY: MISC_FEATURE
<222> LOCATION: (7)..(7)
<223> OTHER INFORMATION: starting methionine
<220> FEATURE:
<221> NAME/KEY: MISC_FEATURE
<222> LOCATION: (7)..(296)
<223> OTHER INFORMATION: CD82; translated sequence to SEQ ID NO: 23
      (Genbank Accession No: NM_002231.3)

<400> SEQUENCE: 24
```

```
Ala Ser Ala Ala Ala Thr Met Asp Tyr Lys Asp Asp Asp Lys Ser
 1               5                  10                  15

Pro Gly Gly Ser Met Gly Ser Ala Cys Ile Lys Val Thr Lys Tyr Phe
            20                  25                  30

Leu Phe Leu Phe Asn Leu Ile Phe Phe Ile Leu Gly Ala Val Ile Leu
        35                  40                  45

Gly Phe Gly Val Trp Ile Leu Ala Asp Lys Ser Ser Phe Ile Ser Val
    50                  55                  60

Leu Gln Thr Ser Ser Ser Ser Leu Arg Met Gly Ala Tyr Val Phe Ile
65                  70                  75                  80

Gly Val Gly Ala Val Thr Met Leu Met Gly Phe Leu Gly Cys Ile Gly
                85                  90                  95

Ala Val Asn Glu Val Arg Cys Leu Leu Gly Leu Tyr Phe Ala Phe Leu
            100                 105                 110

Leu Leu Ile Leu Ile Ala Gln Val Thr Ala Gly Ala Leu Phe Tyr Phe
        115                 120                 125

Asn Met Gly Lys Leu Lys Gln Glu Met Gly Gly Ile Val Thr Glu Leu
    130                 135                 140

Ile Arg Asp Tyr Asn Ser Ser Arg Glu Asp Ser Leu Gln Asp Ala Trp
145                 150                 155                 160

Asp Tyr Val Gln Ala Gln Val Lys Cys Cys Gly Trp Val Ser Phe Tyr
                165                 170                 175
```

```
Asn Trp Thr Asp Asn Ala Glu Leu Met Asn Arg Pro Glu Val Thr Tyr
            180                 185                 190

Pro Cys Ser Cys Glu Val Lys Gly Glu Glu Asp Asn Ser Leu Ser Val
        195                 200                 205

Arg Lys Gly Phe Cys Glu Ala Pro Gly Asn Arg Thr Gln Ser Gly Asn
    210                 215                 220

His Pro Glu Asp Trp Pro Val Tyr Gln Glu Gly Cys Met Glu Lys Val
225                 230                 235                 240

Gln Ala Trp Leu Gln Glu Asn Leu Gly Ile Ile Leu Gly Val Gly Val
                245                 250                 255

Gly Val Ala Met Val Glu Leu Leu Gly Met Val Leu Ser Ile Cys Leu
        260                 265                 270

Cys Arg His Val His Ser Glu Asp Tyr Ser Lys Val Pro Lys Tyr Lys
    275                 280                 285

Leu Ile Asp Thr Val Asp Leu Glu
    290                 295
```

<210> SEQ ID NO 25
<211> LENGTH: 846
<212> TYPE: DNA
<213> ORGANISM: homo sapiens
<220> FEATURE:
<221> NAME/KEY: misc_feature
<222> LOCATION: (18)..(21)
<223> OTHER INFORMATION: start codon

<400> SEQUENCE: 25

```
gctagcgcgg ccgccaccat ggattacaag gatgacgacg ataagagccc gggcggatcc      60
atgggtgagt caacgagaa aagacaaca tgtggcaccg tttgcctcaa gtacctgctg        120
tttaccaca attgctgctt ctggctggct ggcctggctg tcatggcagt gggcatctgg       180
acgctggccc tcaagagtga ctacatcagc ctgctggcct caggcaccta cctggccaca     240
gcctacatcc tggtggtggc gggcactgtc gtcatggtga ctggggtctt gggctgctgc     300
gccaccttca aggagcgtcg gaacctgctg cgcctgtact tcatcctgct cctcatcatc     360
tttctgctgg agatcatcgc tggtatcctc gcctacgcct actaccagca gctgaacacg     420
gagctcaagg agaacctgaa ggacaccatg accaagcgct accaccagcc gggccatgag     480
gctgtgacca cgctgtgga ccagctgcag caggagttcc actgctgtgg cagcaacaac     540
tcacaggact ggcgagacag tgagtggatc cgctcacagg aggccggtgg ccgtgtggtc     600
ccagacagct gctgcaagac ggtggtggct ctttgtggac agcgagacca tgcctccaac    660
atctacaagg tggagggcgg ctgcatcacc aagttggaga ccttcatcca ggagcacctg    720
agggtcattg ggctgtgggg atcggcatt gcctgtgtgc aggtctttgg catgatcttc      780
acgtgctgcc tgtacaggag tctcaagctg gagcactaca gcttatcga taccgtcgac    840
ctcgag                                                                846
```

<210> SEQ ID NO 26
<211> LENGTH: 282
<212> TYPE: PRT
<213> ORGANISM: homo sapiens
<220> FEATURE:
<221> NAME/KEY: MISC_FEATURE
<222> LOCATION: (7)..(7)
<223> OTHER INFORMATION: start codon
<220> FEATURE:
<221> NAME/KEY: MISC_FEATURE
<222> LOCATION: (7)..(7)
<223> OTHER INFORMATION: starting methionine
<220> FEATURE:
<221> NAME/KEY: MISC_FEATURE
<222> LOCATION: (8)..(282)
<223> OTHER INFORMATION: CD151; translated sequence to SEQ ID No: 25
      (Genbank Accession No: BT007397.1)

<400> SEQUENCE: 26

Ala Ser Ala Ala Ala Thr Met Asp Tyr Lys Asp Asp Asp Lys Ser
1               5                   10                  15

Pro Gly Gly Ser Met Gly Glu Phe Asn Glu Lys Lys Thr Thr Cys Gly
            20                  25                  30

Thr Val Cys Leu Lys Tyr Leu Leu Phe Thr Tyr Asn Cys Cys Phe Trp
        35                  40                  45

Leu Ala Gly Leu Ala Val Met Ala Val Gly Ile Trp Thr Leu Ala Leu
    50                  55                  60

Lys Ser Asp Tyr Ile Ser Leu Leu Ala Ser Gly Thr Tyr Leu Ala Thr
65                  70                  75                  80

Ala Tyr Ile Leu Val Val Ala Gly Thr Val Val Met Val Thr Gly Val
                85                  90                  95

Leu Gly Cys Cys Ala Thr Phe Lys Glu Arg Arg Asn Leu Leu Arg Leu
            100                 105                 110

Tyr Phe Ile Leu Leu Leu Ile Ile Phe Leu Leu Glu Ile Ile Ala Gly
        115                 120                 125

Ile Leu Ala Tyr Ala Tyr Tyr Gln Gln Leu Asn Thr Glu Leu Lys Glu
    130                 135                 140

Asn Leu Lys Asp Thr Met Thr Lys Arg Tyr His Gln Pro Gly His Glu
145                 150                 155                 160

Ala Val Thr Ser Ala Val Asp Gln Leu Gln Gln Glu Phe His Cys Cys
                165                 170                 175

Gly Ser Asn Asn Ser Gln Asp Trp Arg Asp Ser Glu Trp Ile Arg Ser
            180                 185                 190

Gln Glu Ala Gly Gly Arg Val Val Pro Asp Ser Cys Cys Lys Thr Val
        195                 200                 205

Val Ala Leu Cys Gly Gln Arg Asp His Ala Ser Asn Ile Tyr Lys Val
    210                 215                 220

Glu Gly Gly Cys Ile Thr Lys Leu Glu Thr Phe Ile Gln Glu His Leu
225                 230                 235                 240

Arg Val Ile Gly Ala Val Gly Ile Gly Ile Ala Cys Val Gln Val Phe
                245                 250                 255

Gly Met Ile Phe Thr Cys Cys Leu Tyr Arg Ser Leu Lys Leu Glu His
            260                 265                 270

Tyr Lys Leu Ile Asp Thr Val Asp Leu Glu
        275                 280

<210> SEQ ID NO 27
<211> LENGTH: 648
<212> TYPE: DNA
<213> ORGANISM: artificial sequence
<220> FEATURE:
<223> OTHER INFORMATION: DNA sequence of CD9delLEL-V5-6xHis;
      based on Genbank Accession No.: NM_001769.3
<220> FEATURE:
<221> NAME/KEY: misc_feature
<222> LOCATION: (18)..(405)
<223> OTHER INFORMATION: TM1-TM3
<220> FEATURE:
<221> NAME/KEY: misc_feature
<222> LOCATION: (18)..(21)
<223> OTHER INFORMATION: start codon
<220> FEATURE:

```
<221> NAME/KEY: misc_feature
<222> LOCATION: (406)..(507)
<223> OTHER INFORMATION: V5-6xHis-Linker
<220> FEATURE:
<221> NAME/KEY: misc_feature
<222> LOCATION: (508)..(648)
<223> OTHER INFORMATION: TM4

<400> SEQUENCE: 27
gctagcgcgg ccgccaccat ggattacaag gatgacgacg ataagagccc gggcggatcc      60
atgccggtca aaggaggcac caagtgcatc aaatacctgc tgttcggatt taacttcatc     120
ttctggcttg ccgggattgc tgtccttgcc attggactat ggctccgatt cgactctcag     180
accaagagca tcttcgagca agaaactaat aataataatt ccagcttcta cacaggagtc     240
tatattctga tcggagccgg cgccctcatg atgctggtgg gcttcctggg ctgctgcggg     300
gctgtgcagg agtcccagtg catgctggga ctgttcttcg gcttcctctt ggtgatattc     360
gccattgaaa tagctgcggc catctgggga tattcccaca aggatgaatt cggaaagggc     420
ccgcggttcg aaggtaagcc tatccctaac cctctcctcg gtctcgattc tacgcgtacc     480
ggtcatcatc accatcacca tgatatcgga ggaggaggaa tcatcggcgc agtgggcatc     540
ggcattgccg tggtcatgat atttggcatg atcttcagta tgatcttgtg ctgtgctatc     600
cgcaggaacc gcgagatggt caagcttatc gataccgtcg acctcgag                  648

<210> SEQ ID NO 28
<211> LENGTH: 216
<212> TYPE: PRT
<213> ORGANISM: artificial sequence
<220> FEATURE:
<223> OTHER INFORMATION: Protein sequence of CD9delLEL-V5-6xHis;
      translated sequence
<220> FEATURE:
<221> NAME/KEY: MISC_FEATURE
<222> LOCATION: (7)..(7)
<223> OTHER INFORMATION: starting methionine
<220> FEATURE:
<221> NAME/KEY: MISC_FEATURE
<222> LOCATION: (7)..(135)
<223> OTHER INFORMATION: TM1-TM3
<220> FEATURE:
<221> NAME/KEY: MISC_FEATURE
<222> LOCATION: (7)..(216)
<223> OTHER INFORMATION: CD9delLEL-V5-6xHis
<220> FEATURE:
<221> NAME/KEY: MISC_FEATURE
<222> LOCATION: (136)..(169)
<223> OTHER INFORMATION: V5-6xHis-Linker
<220> FEATURE:
<221> NAME/KEY: MISC_FEATURE
<222> LOCATION: (170)..(216)
<223> OTHER INFORMATION: TM4

<400> SEQUENCE: 28

Ala Ser Ala Ala Ala Thr Met Asp Tyr Lys Asp Asp Asp Lys Ser
1               5                   10                  15

Pro Gly Gly Ser Met Pro Val Lys Gly Gly Thr Lys Cys Ile Lys Tyr
                20                  25                  30

Leu Leu Phe Gly Phe Asn Phe Ile Phe Trp Leu Ala Gly Ile Ala Val
            35                  40                  45

Leu Ala Ile Gly Leu Trp Leu Arg Phe Asp Ser Gln Thr Lys Ser Ile
        50                  55                  60

Phe Glu Gln Glu Thr Asn Asn Asn Asn Ser Ser Phe Tyr Thr Gly Val
65                  70                  75                  80

Tyr Ile Leu Ile Gly Ala Gly Ala Leu Met Met Leu Val Gly Phe Leu
```

```
            85                  90                  95
Gly Cys Cys Gly Ala Val Gln Glu Ser Gln Cys Met Leu Gly Leu Phe
            100                 105                 110

Phe Gly Phe Leu Leu Val Ile Phe Ala Ile Glu Ile Ala Ala Ala Ile
            115                 120                 125

Trp Gly Tyr Ser His Lys Asp Glu Phe Gly Lys Gly Pro Arg Phe Glu
    130                 135                 140

Gly Lys Pro Ile Pro Asn Pro Leu Leu Gly Leu Asp Ser Thr Arg Thr
145                 150                 155                 160

Gly His His His His His Asp Ile Gly Gly Gly Ile Ile Gly
                165                 170                 175

Ala Val Gly Ile Gly Ile Ala Val Val Met Ile Phe Gly Met Ile Phe
            180                 185                 190

Ser Met Ile Leu Cys Cys Ala Ile Arg Arg Asn Arg Glu Met Val Lys
            195                 200                 205

Leu Ile Asp Thr Val Asp Leu Glu
    210                 215

<210> SEQ ID NO 29
<211> LENGTH: 663
<212> TYPE: DNA
<213> ORGANISM: artificial sequence
<220> FEATURE:
<223> OTHER INFORMATION: DNA sequence of CD81delLEL-V5-6xHis; based on
      Genbank Accession No.: NM_004356.3
<220> FEATURE:
<221> NAME/KEY: misc_feature
<222> LOCATION: (18)..(413)
<223> OTHER INFORMATION: TM1-TM3
<220> FEATURE:
<221> NAME/KEY: misc_feature
<222> LOCATION: (18)..(21)
<223> OTHER INFORMATION: start codon
<220> FEATURE:
<221> NAME/KEY: misc_feature
<222> LOCATION: (414)..(516)
<223> OTHER INFORMATION: V5-6xHis-Linker
<220> FEATURE:
<221> NAME/KEY: misc_feature
<222> LOCATION: (517)..(663)
<223> OTHER INFORMATION: TM4

<400> SEQUENCE: 29
gctagcgcgg ccgccaccat ggattacaag gatgacgacg ataagagccc gggcggatcc     60
atgggagtgg agggctgcac caagtgcatc aagtacctgc tcttcgtctt caatttcgtc    120
ttctggctgg ctggaggcgt gatcctgggt gtggccctgt ggctccgcca tgacccgcag    180
accaccaacc tcctgtatct ggagctggga gacaagcccg cgcccaacac cttctatgta    240
ggcatctaca tcctcatcgc tgtgggcgct gtcatgatgt tcgttggctt cctgggctgc    300
tacggggcca tccaggaatc ccagtgcctg ctggggacgt tcttcacctg cctggtcatc    360
ctgtttgcct gtgaggtggc cgccggcatc tgggctttg tcaacaagga ccaggaattc    420
ggaaagggcc gcgcggttcga aggtaagcct atccctaacc ctctcctcgg tctcgattct    480
acgcgtaccg gtcatcatca ccatcaccat gatatcggag gaggaggaaa gctgtacctc    540
atcggcattg ctgccatcgt ggtcgctgtg atcatgatct tcgagatgat cctgagcatg    600
gtgctgtgct gtggcatccg gaacagctcc gtgtacaagc ttatcgatac cgtcgacctc    660
gag                                                                  663

<210> SEQ ID NO 30
```

<211> LENGTH: 221
<212> TYPE: PRT
<213> ORGANISM: artificial sequence
<220> FEATURE:
<223> OTHER INFORMATION: Protein sequence of CD81delLEL-V5-6xHis;
      translated sequence
<220> FEATURE:
<221> NAME/KEY: MISC_FEATURE
<222> LOCATION: (7)..(7)
<223> OTHER INFORMATION: start codon
<220> FEATURE:
<221> NAME/KEY: MISC_FEATURE
<222> LOCATION: (7)..(7)
<223> OTHER INFORMATION: starting methionine
<220> FEATURE:
<221> NAME/KEY: MISC_FEATURE
<222> LOCATION: (7)..(138)
<223> OTHER INFORMATION: TM1-TM3
<220> FEATURE:
<221> NAME/KEY: MISC_FEATURE
<222> LOCATION: (7)..(221)
<223> OTHER INFORMATION: CD81delLEL-V5-6xHis
<220> FEATURE:
<221> NAME/KEY: MISC_FEATURE
<222> LOCATION: (139)..(172)
<223> OTHER INFORMATION: V5-6xHis-Linker
<220> FEATURE:
<221> NAME/KEY: MISC_FEATURE
<222> LOCATION: (173)..(221)
<223> OTHER INFORMATION: TM4

<400> SEQUENCE: 30

Ala Ser Ala Ala Ala Thr Met Asp Tyr Lys Asp Asp Asp Lys Ser
1               5                   10                  15

Pro Gly Gly Ser Met Gly Val Glu Gly Cys Thr Lys Cys Ile Lys Tyr
                20                  25                  30

Leu Leu Phe Val Phe Asn Phe Val Phe Trp Leu Ala Gly Gly Val Ile
            35                  40                  45

Leu Gly Val Ala Leu Trp Leu Arg His Asp Pro Gln Thr Thr Asn Leu
50                  55                  60

Leu Tyr Leu Glu Leu Gly Asp Lys Pro Ala Pro Asn Thr Phe Tyr Val
65                  70                  75                  80

Gly Ile Tyr Ile Leu Ile Ala Val Gly Ala Val Met Met Phe Val Gly
                85                  90                  95

Phe Leu Gly Cys Tyr Gly Ala Ile Gln Glu Ser Gln Cys Leu Leu Gly
            100                 105                 110

Thr Phe Phe Thr Cys Leu Val Ile Leu Phe Ala Cys Glu Val Ala Ala
        115                 120                 125

Gly Ile Trp Gly Phe Val Asn Lys Asp Gln Glu Phe Gly Lys Gly Pro
130                 135                 140

Arg Phe Glu Gly Lys Pro Ile Pro Asn Pro Leu Leu Gly Leu Asp Ser
145                 150                 155                 160

Thr Arg Thr Gly His His His His His His Asp Ile Gly Gly Gly
                165                 170                 175

Lys Leu Tyr Leu Ile Gly Ile Ala Ala Ile Val Val Ala Val Ile Met
            180                 185                 190

Ile Phe Glu Met Ile Leu Ser Met Val Leu Cys Cys Gly Ile Arg Asn
        195                 200                 205

Ser Ser Val Tyr Lys Leu Ile Asp Thr Val Asp Leu Glu
    210                 215                 220

<210> SEQ ID NO 31
<211> LENGTH: 690
<212> TYPE: DNA

```
<213> ORGANISM: artificial sequence
<220> FEATURE:
<223> OTHER INFORMATION: DNA sequence of CD82delLEL-V5-6xHis; based on
      Genbank Accession No.: NM_002231.3
<220> FEATURE:
<221> NAME/KEY: misc_feature
<222> LOCATION: (18)..(21)
<223> OTHER INFORMATION: start codon
<220> FEATURE:
<221> NAME/KEY: misc_feature
<222> LOCATION: (18)..(405)
<223> OTHER INFORMATION: TM1-TM3
<220> FEATURE:
<221> NAME/KEY: misc_feature
<222> LOCATION: (406)..(507)
<223> OTHER INFORMATION: V5-6xHis-Linker
<220> FEATURE:
<221> NAME/KEY: misc_feature
<222> LOCATION: (508)..(690)
<223> OTHER INFORMATION: TM4

<400> SEQUENCE: 31
gctagcgcgg ccgccaccat ggattacaag gatgacgacg ataagagccc gggcggatcc      60
atgggctcag cctgtatcaa agtcaccaaa tactttctct tcctcttcaa cttgatcttc     120
tttatcctgg gcgcagtgat cctgggcttc ggggtgtgga tcctggccga caagagcagt     180
ttcatctctg tcctgcaaac ctcctccagc tcgcttagga tggggggccta tgtcttcatc     240 ggcgtggggg cagtcactat gctcatgggc ttcctgggct gcatcggcgc cgtcaacgag     300
gtccgctgcc tgctggggct gtactttgct ttcctgctcc tgatcctcat tgcccaggtg     360
acggccgggg cactcttcta cttcaacatg ggcaagctga agcaggaatt cggaaagggc     420
ccgcggttcg aaggtaagcc tatccctaac cctctcctcg gtctcgattc tacgcgtacc     480
ggtcatcatc accatcacca tgatatcgga ggaggaggag tgcaggcgtg gctgcaggag     540
aacctgggca tcatcctcgg cgtgggcgtg ggtgtggcca tggtcgagct cctggggatg     600
gtcctgtcca tctgcttgtg ccggcacgtg cattccgaag actacagcaa ggtccccaag     660
tacaagctta tcgataccgt cgacctcgag                                      690

<210> SEQ ID NO 32
<211> LENGTH: 230
<212> TYPE: PRT
<213> ORGANISM: artificial sequence
<220> FEATURE:
<223> OTHER INFORMATION: Protein sequence of CD82delLEL-V5-6xHis;
      translated sequence
<220> FEATURE:
<221> NAME/KEY: MISC_FEATURE
<222> LOCATION: (7)..(7)
<223> OTHER INFORMATION: starting methionine
<220> FEATURE:
<221> NAME/KEY: MISC_FEATURE
<222> LOCATION: (7)..(135)
<223> OTHER INFORMATION: TM1-TM3
<220> FEATURE:
<221> NAME/KEY: MISC_FEATURE
<222> LOCATION: (7)..(230)
<223> OTHER INFORMATION: CD82delLEL-V5-6xHis
<220> FEATURE:
<221> NAME/KEY: MISC_FEATURE
<222> LOCATION: (136)..(169)
<223> OTHER INFORMATION: V5-6xHis-Linker
<220> FEATURE:
<221> NAME/KEY: MISC_FEATURE
<222> LOCATION: (170)..(230)
<223> OTHER INFORMATION: TM4

<400> SEQUENCE: 32

Ala Ser Ala Ala Ala Thr Met Asp Tyr Lys Asp Asp Asp Lys Ser
```

```
            1               5                  10                 15
         Pro Gly Gly Ser Met Gly Ser Ala Cys Ile Lys Val Thr Lys Tyr Phe
                         20                  25                  30
         Leu Phe Leu Phe Asn Leu Ile Phe Phe Ile Leu Gly Ala Val Ile Leu
                         35                  40                  45
         Gly Phe Gly Val Trp Ile Leu Ala Asp Lys Ser Ser Phe Ile Ser Val
                     50                  55                  60
         Leu Gln Thr Ser Ser Ser Leu Arg Met Gly Ala Tyr Val Phe Ile
         65                  70                  75                  80
         Gly Val Gly Ala Val Thr Met Leu Met Gly Phe Leu Gly Cys Ile Gly
                             85                  90                  95
         Ala Val Asn Glu Val Arg Cys Leu Leu Gly Leu Tyr Phe Ala Phe Leu
                         100                 105                 110
         Leu Leu Ile Leu Ile Ala Gln Val Thr Ala Gly Ala Leu Phe Tyr Phe
                         115                 120                 125
         Asn Met Gly Lys Leu Lys Gln Glu Phe Gly Lys Gly Pro Arg Phe Glu
                         130                 135                 140
         Gly Lys Pro Ile Pro Asn Pro Leu Leu Gly Leu Asp Ser Thr Arg Thr
         145                 150                 155                 160
         Gly His His His His His His Asp Ile Gly Gly Gly Val Gln Ala
                             165                 170                 175
         Trp Leu Gln Glu Asn Leu Gly Ile Ile Leu Gly Val Gly Val Gly Val
                         180                 185                 190
         Ala Met Val Glu Leu Leu Gly Met Val Leu Ser Ile Cys Leu Cys Arg
                         195                 200                 205
         His Val His Ser Glu Asp Tyr Ser Lys Val Pro Lys Tyr Lys Leu Ile
                         210                 215                 220
         Asp Thr Val Asp Leu Glu
         225                 230
```

<210> SEQ ID NO 33
<211> LENGTH: 663
<212> TYPE: DNA
<213> ORGANISM: artificial sequence
<220> FEATURE:
<223> OTHER INFORMATION: DNA sequence of CD151delLEL-V5-6xHis; based on Genbank Accession No.: BT001769.3
<220> FEATURE:
<221> NAME/KEY: misc_feature
<222> LOCATION: (18)..(21)
<223> OTHER INFORMATION: start codon
<220> FEATURE:
<221> NAME/KEY: misc_feature
<222> LOCATION: (18)..(420)
<223> OTHER INFORMATION: TM1-TM3
<220> FEATURE:
<221> NAME/KEY: misc_feature
<222> LOCATION: (421)..(522)
<223> OTHER INFORMATION: V5-6xHis-Linker
<220> FEATURE:
<221> NAME/KEY: misc_feature
<222> LOCATION: (523)..(663)
<223> OTHER INFORMATION: TM4

<400> SEQUENCE: 33

```
gctagcgcgg ccgccaccat ggattacaag gatgacgacg ataagagccc gggcggatcc    60
atgggtgagt caacgagaa aagacaaca tgtggcaccg tttgcctcaa gtacctgctg    120
tttacctaca attgctgctt ctggctggct ggcctggctg tcatggcagt gggcatctgg    180
acgctggccc tcaagagtga ctacatcagc ctgctggcct caggcaccta cctggccaca    240
```

```
gcctacatcc tggtggtggc gggcactgtc gtcatggtga ctggggtctt gggctgctgc    300
gccaccttca aggagcgtcg gaacctgctg cgcctgtact tcatcctgct cctcatcatc    360
tttctgctgg agatcatcgc tggtatcctc gcctacgcct actaccagca gctgaacacg    420
gaattcggaa agggcccgcg gttcgaaggt aagcctatcc ctaaccctct cctcggtctc    480
gattctacgc gtaccggtca tcatcaccat caccatgata tcggaggagg aggactgagg    540
gtcattgggg ctgtggggat cggcattgcc tgtgtgcagg tctttggcat gatcttcacg    600
tgctgcctgt acaggagtct caagctggag cactacaagc ttatcgatac cgtcgacctc    660
gag                                                                  663
```

<210> SEQ ID NO 34
<211> LENGTH: 221
<212> TYPE: PRT
<213> ORGANISM: artificial sequence
<220> FEATURE:
<223> OTHER INFORMATION: Protein sequence of CD151delLEL-V5-6xHis;
      translated sequence
<220> FEATURE:
<221> NAME/KEY: MISC_FEATURE
<222> LOCATION: (7)..(7)
<223> OTHER INFORMATION: starting methionine
<220> FEATURE:
<221> NAME/KEY: MISC_FEATURE
<222> LOCATION: (7)..(140)
<223> OTHER INFORMATION: TM1-TM3
<220> FEATURE:
<221> NAME/KEY: MISC_FEATURE
<222> LOCATION: (7)..(221)
<223> OTHER INFORMATION: CD151delLEL-V5-6xHis
<220> FEATURE:
<221> NAME/KEY: MISC_FEATURE
<222> LOCATION: (141)..(174)
<223> OTHER INFORMATION: V5-6xHis-Linker
<220> FEATURE:
<221> NAME/KEY: MISC_FEATURE
<222> LOCATION: (175)..(221)
<223> OTHER INFORMATION: TM4

<400> SEQUENCE: 34

Ala Ser Ala Ala Ala Thr Met Asp Tyr Lys Asp Asp Asp Lys Ser
1               5                   10                  15

Pro Gly Gly Ser Met Gly Glu Phe Asn Glu Lys Lys Thr Thr Cys Gly
                20                  25                  30

Thr Val Cys Leu Lys Tyr Leu Leu Phe Thr Tyr Asn Cys Cys Phe Trp
            35                  40                  45

Leu Ala Gly Leu Ala Val Met Ala Val Gly Ile Trp Thr Leu Ala Leu
        50                  55                  60

Lys Ser Asp Tyr Ile Ser Leu Leu Ala Ser Gly Thr Tyr Leu Ala Thr
65                  70                  75                  80

Ala Tyr Ile Leu Val Val Ala Gly Thr Val Met Val Thr Gly Val
                85                  90                  95

Leu Gly Cys Cys Ala Thr Phe Lys Glu Arg Arg Asn Leu Leu Arg Leu
            100                 105                 110

Tyr Phe Ile Leu Leu Leu Ile Ile Phe Leu Leu Glu Ile Ile Ala Gly
        115                 120                 125

Ile Leu Ala Tyr Ala Tyr Tyr Gln Gln Leu Asn Thr Glu Phe Gly Lys
    130                 135                 140

Gly Pro Arg Phe Glu Gly Lys Pro Ile Pro Asn Pro Leu Leu Gly Leu
145                 150                 155                 160

Asp Ser Thr Arg Thr Gly His His His His His His Asp Ile Gly Gly
                165                 170                 175

```
Gly Gly Leu Arg Val Ile Gly Ala Val Gly Ile Gly Ile Ala Cys Val
            180                 185                 190

Gln Val Phe Gly Met Ile Phe Thr Cys Cys Leu Tyr Arg Ser Leu Lys
        195                 200                 205

Leu Glu His Tyr Lys Leu Ile Asp Thr Val Asp Leu Glu
    210                 215                 220
```

<210> SEQ ID NO 35
<211> LENGTH: 102
<212> TYPE: DNA
<213> ORGANISM: artificial sequence
<220> FEATURE:
<223> OTHER INFORMATION: DNA sequence of the V5-6xHis linker in
      Tetraspanin delLEL-V5-6xHis constructs
<220> FEATURE:
<221> NAME/KEY: misc_feature
<222> LOCATION: (1)..(6)
<223> OTHER INFORMATION: EcoRI site
<220> FEATURE:
<221> NAME/KEY: misc_feature
<222> LOCATION: (97)..(102)
<223> OTHER INFORMATION: EcoRV site

<400> SEQUENCE: 35
gaattcggaa agggcccgcg gttcgaaggt aagcctatcc ctaaccctct cctcggtctc     60
gattctacgc gtaccggtca tcatcaccat caccatgata tc                      102

<210> SEQ ID NO 36
<211> LENGTH: 34
<212> TYPE: PRT
<213> ORGANISM: artificial sequence
<220> FEATURE:
<223> OTHER INFORMATION: Protein sequence of the V5-6xHis linker in
      Tetraspanin delLEL-V5-6xHis constructs; translated sequence
<220> FEATURE:
<221> NAME/KEY: MISC_FEATURE
<222> LOCATION: (3)..(23)
<223> OTHER INFORMATION: V5-Epitop
<220> FEATURE:
<221> NAME/KEY: MISC_FEATURE
<222> LOCATION: (27)..(32)
<223> OTHER INFORMATION: 6xHis-Epitop

<400> SEQUENCE: 36

```
Glu Phe Gly Lys Gly Pro Arg Phe Glu Gly Lys Pro Ile Pro Asn Pro
1               5                   10                  15

Leu Leu Gly Leu Asp Ser Thr Arg Thr Gly His His His His His His
            20                  25                  30

Asp Ile
```

<210> SEQ ID NO 37
<211> LENGTH: 126
<212> TYPE: DNA
<213> ORGANISM: artificial sequence
<220> FEATURE:
<223> OTHER INFORMATION: DNA sequence of the 2F5-4E10 linker
<220> FEATURE:
<221> NAME/KEY: misc_feature
<222> LOCATION: (1)..(6)
<223> OTHER INFORMATION: EcoRI site
<220> FEATURE:
<221> NAME/KEY: misc_feature
<222> LOCATION: (121)..(126)
<223> OTHER INFORMATION: EcoRV site

<400> SEQUENCE: 37
gaattcattg aagaatcgca aaaccagcaa gaaaagaatg aacaagaatt attggaatta     60
gataaatggg caagtttgtg gaattggttt aacataacaa attggctgtg gtatataaaa    120
gatatc    126

<210> SEQ ID NO 38
<211> LENGTH: 42
<212> TYPE: PRT
<213> ORGANISM: artificial sequence
<220> FEATURE:
<223> OTHER INFORMATION: Protein sequence of the 2F5-4E10 linker;
      translated sequence
<220> FEATURE:
<221> NAME/KEY: MISC_FEATURE
<222> LOCATION: (19)..(24)
<223> OTHER INFORMATION: 2F5-Epitop
<220> FEATURE:
<221> NAME/KEY: MISC_FEATURE
<222> LOCATION: (28)..(33)
<223> OTHER INFORMATION: 4E10-Epitop

<400> SEQUENCE: 38

Glu Phe Ile Glu Glu Ser Gln Asn Gln Gln Glu Lys Asn Glu Gln Glu
1               5                   10                  15

Leu Leu Leu Glu Asp Lys Trp Ala Ser Leu Trp Asn Trp Phe Asn Ile
            20                  25                  30

Thr Asn Trp Leu Trp Tyr Ile Lys Asp Ile
        35                  40

<210> SEQ ID NO 39
<211> LENGTH: 120
<212> TYPE: DNA
<213> ORGANISM: Artificial Sequence
<220> FEATURE:
<223> OTHER INFORMATION: DNA sequence of the linker version (8)
<220> FEATURE:
<221> NAME/KEY: misc_feature
<222> LOCATION: (1)..(6)
<223> OTHER INFORMATION: EcoRI site
<220> FEATURE:
<221> NAME/KEY: misc_feature
<222> LOCATION: (7)..(26)
<223> OTHER INFORMATION: TEV-Proteolyse-I
<220> FEATURE:
<221> NAME/KEY: misc_feature
<222> LOCATION: (27)..(33)
<223> OTHER INFORMATION: HindIII site
<220> FEATURE:
<221> NAME/KEY: misc_feature
<222> LOCATION: (34)..(39)
<223> OTHER INFORMATION: BamHI site
<220> FEATURE:
<221> NAME/KEY: misc_feature
<222> LOCATION: (40)..(46)
<223> OTHER INFORMATION: PstI site
<220> FEATURE:
<221> NAME/KEY: misc_feature
<222> LOCATION: (46)..(63)
<223> OTHER INFORMATION: His6-Tag
<220> FEATURE:
<221> NAME/KEY: misc_feature
<222> LOCATION: (64)..(84)
<223> OTHER INFORMATION: TEV-Proteolyse-II
<220> FEATURE:
<221> NAME/KEY: misc_feature
<222> LOCATION: (85)..(97)
<223> OTHER INFORMATION: c-Myc-Epitope1
<220> FEATURE:
<221> NAME/KEY: misc_feature
<222> LOCATION: (103)..(114)
<223> OTHER INFORMATION: c-Myc-Epitope2
<220> FEATURE:
<221> NAME/KEY: misc_feature
<222> LOCATION: (115)..(120)

<223> OTHER INFORMATION: EcoRV site

<400> SEQUENCE: 39
gaattcgaga atctgtactt tcagtcgaag cttggatccc tgcagcatca ccatcaccat  60
cacgaaaacc tctatttcca gagcgaacag aaactgatat ccgaagaaga tctggatatc  120

<210> SEQ ID NO 40
<211> LENGTH: 40
<212> TYPE: PRT
<213> ORGANISM: Artificial Sequence
<220> FEATURE:
<223> OTHER INFORMATION: Protein sequence of the linker version (8);
      translated sequence
<220> FEATURE:
<221> NAME/KEY: MISC_FEATURE
<222> LOCATION: (3)..(8)
<223> OTHER INFORMATION: TEV-Proteolysis-I
<220> FEATURE:
<221> NAME/KEY: MISC_FEATURE
<222> LOCATION: (16)..(21)
<223> OTHER INFORMATION: His6-Tag
<220> FEATURE:
<221> NAME/KEY: MISC_FEATURE
<222> LOCATION: (22)..(28)
<223> OTHER INFORMATION: TEV-Proteolysis-I
<220> FEATURE:
<221> NAME/KEY: MISC_FEATURE
<222> LOCATION: (29)..(33)
<223> OTHER INFORMATION: c-Myc-Epitope1
<220> FEATURE:
<221> NAME/KEY: MISC_FEATURE
<222> LOCATION: (34)..(38)
<223> OTHER INFORMATION: c-Myc-Epitope2

<400> SEQUENCE: 40

Glu Phe Glu Asn Leu Tyr Phe Gln Ser Lys Leu Gly Ser Leu Gln His
1               5                   10                  15

His His His His His Glu Asn Leu Tyr Phe Gln Ser Glu Gln Lys Leu
            20                  25                  30

Ile Ser Glu Glu Asp Leu Asp Ile
        35                  40

<210> SEQ ID NO 41
<211> LENGTH: 27
<212> TYPE: DNA
<213> ORGANISM: artificial sequence
<220> FEATURE:
<223> OTHER INFORMATION: DNA sequence of the linker in the vector
      pCMV-CD63delLEL-mCherry (minimal linker (9))
<220> FEATURE:
<221> NAME/KEY: misc_feature
<222> LOCATION: (1)..(6)
<223> OTHER INFORMATION: PstI site
<220> FEATURE:
<221> NAME/KEY: misc_feature
<222> LOCATION: (7)..(12)
<223> OTHER INFORMATION: EcoRI site
<220> FEATURE:
<221> NAME/KEY: misc_feature
<222> LOCATION: (13)..(18)
<223> OTHER INFORMATION: EcoRV site
<220> FEATURE:
<221> NAME/KEY: misc_feature
<222> LOCATION: (19)..(27)
<223> OTHER INFORMATION: 4x Glycin

<400> SEQUENCE: 41
ctgcaggaat tcgatatcgg aggagga  27

<210> SEQ ID NO 42

```
<211> LENGTH: 10
<212> TYPE: PRT
<213> ORGANISM: artificial sequence
<220> FEATURE:
<223> OTHER INFORMATION: Protein sequence of the linker in the vector
      pCMV-CD63delLEL-mCherry; translated sequence (minimal linker (9))

<400> SEQUENCE: 42

Leu Gln Glu Phe Asp Ile Gly Gly Gly Gly
1               5                   10

<210> SEQ ID NO 43
<211> LENGTH: 41
<212> TYPE: DNA
<213> ORGANISM: artificial sequence
<220> FEATURE:
<223> OTHER INFORMATION: DNA sequence of the linker in the vector
      pCMV-CD63delLEL-V2-mCherry
<220> FEATURE:
<221> NAME/KEY: misc_feature
<222> LOCATION: (3)..(8)
<223> OTHER INFORMATION: BamHI site
<220> FEATURE:
<221> NAME/KEY: misc_feature
<222> LOCATION: (18)..(23)
<223> OTHER INFORMATION: BglIII site
<220> FEATURE:
<221> NAME/KEY: misc_feature
<222> LOCATION: (24)..(29)
<223> OTHER INFORMATION: PstI site

<400> SEQUENCE: 43
ttggatccag cggccgcaga tctctgcagg gaggcggagg c                         41

<210> SEQ ID NO 44
<211> LENGTH: 13
<212> TYPE: PRT
<213> ORGANISM: artificial sequence
<220> FEATURE:
<223> OTHER INFORMATION: Protein sequence of the linker in the vector
      pCMV-CD63delLEL-V2-mCherry; translated sequence (linker)

<400> SEQUENCE: 44

Gly Ser Ser Gly Arg Arg Ser Leu Gln Gly Gly Gly Gly
1               5                   10

<210> SEQ ID NO 45
<211> LENGTH: 30
<212> TYPE: DNA
<213> ORGANISM: Artificial Sequence
<220> FEATURE:
<223> OTHER INFORMATION: DNA sequence of the linker between CD63delLEL
      and the fluorescent protein

<400> SEQUENCE: 45
aagcttatcg ataccgtcga cctcgagaaa                                      30

<210> SEQ ID NO 46
<211> LENGTH: 10
<212> TYPE: PRT
<213> ORGANISM: Artificial Sequence
<220> FEATURE:
<223> OTHER INFORMATION: Protein sequence of the linker between
      CD63delLEL and the fluorescent protein; translated sequence

<400> SEQUENCE: 46

Lys Leu Ile Asp Thr Val Asp Leu Glu Lys
1               5                   10
```